US007776352B2

(12) United States Patent
Ruberti et al.

(10) Patent No.: US 7,776,352 B2
(45) Date of Patent: Aug. 17, 2010

(54) SYSTEMS AND METHODS FOR CONTROLLING AND FORMING POLYMER HYDROGELS

(75) Inventors: Jeffrey W. Ruberti, Lexington, MA (US); Gavin J. C. Braithwaite, Cambridge, MA (US)

(73) Assignee: Cambridge Polymer Group, Inc., Boston, MA (US)

( * ) Notice: Subject to any disclaimer, the term of this patent is extended or adjusted under 35 U.S.C. 154(b) by 582 days.

(21) Appl. No.: 11/462,813

(22) Filed: Aug. 7, 2006

(65) Prior Publication Data
US 2007/0054990 A1 Mar. 8, 2007

Related U.S. Application Data

(62) Division of application No. 10/771,852, filed on Feb. 4, 2004, now Pat. No. 7,485,670, and a division of application No. 10/631,491, filed on Jul. 13, 2003, now Pat. No. 7,745,532.

(60) Provisional application No. 60/400,899, filed on Aug. 2, 2002.

(51) Int. Cl.
*A61M 5/19* (2006.01)
*A61J 1/10* (2006.01)
(52) U.S. Cl. .................. 424/423; 424/486; 516/902; 524/916
(58) Field of Classification Search ................ 424/423, 424/486; 516/902; 524/916
See application file for complete search history.

(56) References Cited

U.S. PATENT DOCUMENTS 3,875,302 A 4/1975 Inoue (Continued)

FOREIGN PATENT DOCUMENTS

EP 1229873 8/2002

(Continued)

OTHER PUBLICATIONS

AAOS, Musculoskeletal Conditions in the U.S., Feb. 1992-1988, 1992, AAOS.

(Continued)

*Primary Examiner*—Kelechi C Egwim
(74) *Attorney, Agent, or Firm*—Perkins Coie LLP

(57) ABSTRACT

In preferred embodiments, the present invention provides methods of controllably making a vinyl polymer hydrogel having desired physical properties without chemical cross links or radiation. The gelation process is modulated by controlling, for example, the temperature of a resultant vinyl polymer mixture having a gellant or using active ingredients provided in an inactive gellant complex. In accordance with a preferred embodiment, the method of manufacturing a vinyl polymer hydrogel includes the steps of providing a vinyl polymer solution comprising a vinyl polymer dissolved in a first solvent; heating the vinyl polymer solution to a temperature elevated above the melting point of the physical associations of the vinyl polymer, mixing the vinyl polymer solution with a gellant, wherein the resulting mixture has a higher Flory interaction parameter than the vinyl polymer solution; inducing gelation of the mixture of vinyl polymer solution and gellant; and controlling the gelation rate to form a viscoelastic solution, wherein workability is maintained for a predetermined period, thereby making a vinyl polymer hydrogel having the desired physical property. In further preferred embodiments, the present invention provides physically crosslinked hydrogels produced by controlled gelation of viscoelastic solution wherein workability is maintained for a predetermined period. In another aspect, the present invention provides kits for use in repairing intervertebral disks or articulated joints including components that form the vinyl polymer hydrogel and a dispenser.

27 Claims, 31 Drawing Sheets

U.S. PATENT DOCUMENTS

| | | | |
|---|---|---|---|
| 4,472,542 A | 9/1984 | Nambu | |
| 4,663,358 A | 5/1987 | Hyon | |
| 4,772,287 A | 9/1988 | Ray | |
| 4,904,260 A | 2/1990 | Ray et al. | |
| 5,047,055 A | 9/1991 | Bao | |
| 5,071,437 A | 12/1991 | Steffee | |
| 5,260,066 A | 11/1993 | Wood | |
| 5,288,503 A | 2/1994 | Wood | |
| 5,385,606 A | 1/1995 | Kowanko | 106/124 |
| 5,534,028 A | 7/1996 | Bao | |
| 5,705,296 A | 1/1998 | Kamauchi | |
| 5,731,005 A | 3/1998 | Ottoboni | |
| 5,880,216 A | 3/1999 | Tanihara | |
| 5,976,186 A | 11/1999 | Bao | |
| 5,981,826 A | 11/1999 | Ku | |
| 6,165,201 A * | 12/2000 | Sawhney et al. | 606/214 |
| 6,231,605 B1 | 5/2001 | Ku | |
| 6,264,695 B1 | 7/2001 | Stoy | |
| 6,268,405 B1 | 7/2001 | Yao | |
| 6,423,333 B1 | 7/2002 | Stedronsky et al. | 424/423 |
| 6,520,992 B1 | 2/2003 | Zollner et al. | 623/17.16 |
| 7,001,431 B2 | 2/2006 | Bao et al. | 623/17.12 |
| 7,098,194 B2 | 8/2006 | Chenite et al. | 514/55 |
| 7,214,245 B1 | 5/2007 | Marcolongo et al. | 623/17.16 |
| 2004/0092653 A1 | 5/2004 | Ruberti | |
| 2004/0171740 A1 | 9/2004 | Ruberti | |
| 2005/0112186 A1 | 5/2005 | Devore et al. | |
| 2005/0288789 A1 | 12/2005 | Chaouk et al. | |
| 2006/0270781 A1 | 11/2006 | Ruberti et al. | |
| 2007/0100349 A1 | 5/2007 | O'Neil et al. | |
| 2007/0167541 A1 | 7/2007 | Ruberti et al. | |

FOREIGN PATENT DOCUMENTS

| | | |
|---|---|---|
| JP | 03215417 A | 9/1991 |
| JP | 04 338326 A | 11/1992 |
| WO | WO 01/12107 A1 | 2/2001 |
| WO | WO 02/054978 A2 | 7/2002 |

OTHER PUBLICATIONS

Bao, Q.B., & Yuan, H. A., "Nucleus Replacement," Spine, vol. 27, No. 11, 2002, 1245-1247.

Bao, Q. & Yuan, H.A, "Prosthetic Disc Replacement: The Future?," Clinical Orthopaedics and Related Research, No. 394, pp. 139-145, 2002.

Zeegers, W. S., et al, "Artificial disc replacement with the modular type SB Charit III: 2-year results in 50 prospectively studied patients," Eur Spine J, 8:210-217, 1999.

Wiesel, S.W. et al, "Industrial Low-Back Pain-A Prospective Evaluation of a Standardized Diagnositc and Treatment Protocol," Spine, vol. 9, No. 2, 199-203, 1984.

Bao, Q. et al, "The artificial disc: theory, design and materials," Biomaterials vol. 17, No. 12, (1996) 1157-1167.

Urushizaki, F. et al, "Swelling and mechanical properties of poly(vinyl alcohol) hydrogels," International Journal of Pharmaceutics, 58 135-142, 1990.

UPMC Surgeons Implanting Metal Cages into the Spine to Treat Chronic Low Back Pain, Neurosurgery News, 1999, University of Pittsburgh.

Takeshita, H. et al, "Gelation Process and Phase Separation of PVA Solutions as Studied by a Light Scattering Technique," Macromolecules 32, 7815-7819, 1999.

Oka, M. et al, "Development of artificial articular cartilage," Proc Instn Mech Engrs vol. 214 Part H, 59-68, 2000.

Onuki, A. & Puri, S., "Spinodal decomposition in gels," Physical Review E, vol. 59, No. 2, Feb. 1999, R1331-R1334.

Mike, C., "FDA Approves Bone Graft," 2002, http://www.news.wisc.edu/view.html?get=7640.

Takeshita, H. et al, "Small-angle neutron scattering studies on network structure of transparent and opaque PVA gels," Physica B 311 (2002) 78-83.

Lozinsky, V. I. et al, Swelling behavior of poly(vinyl alcohol) cryogels employed as matrices for cell immobilization), Enzyme Microb. Technol, vol. 18, 561-569, 1996.

Kawanishi K. et al, "Thermodynamic consideration of the sol-gel transition in polymer solutions," 35th Annual Meeting of the Society of Polymer Science, Japan, 1986.

"New Implants Offer Relief of Spine" 2001, Medical Device and Diagnostic Industry.

Takeshita, H., et al, "Spinodal Decomposition and Syneresis of PVA Gel," Macromolecules 2001, 34, 7894-7898.

Diwan, A. D. et al, "Current Concepts in Intervertebral Disk Restoration," Tissue Engineering in Orthopedic Surgery, vol. 31, No. 3, pp. 453-464, Jul. 2000.

Peppas, N. A. et al, "Physicochemical Foundations and Structural Design of Hydrogels in Medicine and Biology," Annu. Rev. Biomed. Eng., 02:9-20, 2000.

Willcox, P. J., et al, "Microstructure of Poly(vinyl alcohol) Hydrogels Produced by Freeze/Thaw Cycling," Journal of Polymer Science: Part B: Polymer Physics, vol. 37, 3438-3454 (1999).

Bray, J.C. & Merrill, E. W., "Poly(vinyl alcohol) Hydrogels for Synthetic Articular Cartilage Material," Biomed. Mater. Res., vol. 7, pp. 431-443 1973.

Stammen, J. A., et al., "Mechanical properties of a novel PVA hydrogel in shear and unconfined compression," Biomaterials, Apr. 22, 2001 (8), 799-806, abstract only.

Bray, J.C. & Merrill, E. W., "Poly(vinyl Alcohol) Hydrogels. Formation by Electron Beam Irradiation of Aqueous Solutions and Subsequent Crystallization," Journal of Applied Polymer Science, vol. 17, pp. 3779-3794, 1973.

Hong, P, et al, "Solvent Effect on Structural Change of Poly(vinyl alcohol) Physical Gels," Journal of Applied Polymer Science, vol. 69, 2477-2486 (1998).

Hong, P. et al, "Effects of Mixed Solvent on Gelation of Poly(vinyl alcohol) Solutions," Journal of Applied Polymer Science, vol. 79, Issue: 6, Date: Feb. 7, 2001, pp. 1113-1120.

Hassan C. M. & Peppas N. A., "Structure and Morphology of Freeze/Thawed PVA Hydrogels," Macromolecule, vol. 33, No. 7, 2472-2479, 2000.

Griffith, S. L. et al, "A Multicenter Retrospective Study of the Clinical Results of the LINK® SB Charite Intervertebral Prosthesis," Spine, vol. 19, No. 16, 1842-1849, 1994.

Flory, P.J., "Principles of Polymer Chemistry," 1953, Ithaca and London: Cornell University Press.

de Gennes, P.G., "Scaling Concepts in Polymer Physics," First ed. 1979: Cornell University Press, 72, 113-114.

Choi, J. H., et al., "Rheological Properties of Syndiotacricity-Rich Ultrahigh Molecular Weight Poly(vinyl alcohol) Dilute Solution," Journal of Applied Polymer Science, vol. 82, 569-576 (2001).

Doehring, T.C. et al, "Cyclic Load-Displacement Characteristics of Lumber Functional Spinal Units," 46th Annual Meeting, Orthopaedic Research Society, Mar. 12-15, 2000.

Damshkaln, L. G., et al, Study of Cryostructurarion of Polymer Systems. XV. Freeze-Thaw-Induced Formation of Cryoprecipitate Matter from Low-Concentrated Aquenous Solutions of Poly(vinyl alcohol), Journal of Applied Polymer Science, vol. 74, 1978-1986 (1999).

Darwis, D., et al, "Characterization of poly(vinyl alcohol) hydrogel for prosthetic intervetebral disc nucleus," Radiation Physics and Chemistry 63 (2002) 539-542.

Gomes, K. et al, "The Effect of Dehydration History on Associating Hydrogels for Nucleus Pulposus Replacement," Society for Biomaterials, 28th Annual Meeting Transactions, 2002.

Hassan C., M. et al, "Diffusional characteristics of freeze/thawed poly(vinyl alcohol) hydrogels: Applications to protein controlled release from multilaminate devices," European Journal of Pharmaceutics and Biopharmaceutics 49 (2000) 161-165.

Elias, H.G., "Theta Solvents," Brandrup, J. and E. H. Immergut, Polymer Handbook 3rd Ed., John Wiley & Sons, NY 1989.

Hassan, C., M., & Peppas, N.A., "Cellular PVA Hydrogels Produced by Freeze/Thawing," Journal of Applied Polymer Science, vol. 76, 2075-2078 (2000).

Lozinsky, V. I., et al, "Study of Cryostructuration of Polymer Systems, XIV. Poly(vinyl alcohol) Cryogels: Apparent Yield of the Freeze-Thaw-Induced Gelation of Concentrated Aqueous Solutions of the Polymer," Journal of Applied Polymer Science, vol. 77, 1822-1831 (2000).

Nakane, K., et al., "Properties and Structure of Poly(vinyl alcohol)/Silica Composites," Journal of Applied Polymer Science, vol. 74, 133-138 (1999).

Hassan, C., M. et al., "Modeling of crystal dissolution of poly(vinyl alcohol) gels produced by freezing/thawing process," Polymer 41 (2000) 6729-6739.

Hickey, A. S. & Peppas N.A., "Solute diffusion in poly(vinyl alcohol)/poly(acrylic acid) composite membranes prepared by freezing/thawing techniques," Polymer, vol. 38 No. 24 1997 5931-5936.

Li, J. K., et al, "Poly(vinyl alcohol) nanoparticles prepared by freezing-thawing process for protein/peptide drug delivery," Journal of Controlled Release 56 (1998) 117-126.

Lozinskii V. I. & Savina I. N., "Study of Cryostructuring of Polymer Systems: 22. Composite Poly(vinyl alcohol) Cryogels Filled with Dispersed Particles of Various Degrees of Hydrophilicity/Hydrophobicity," Colloid Journal, vol. 64, No. 3, 2002, 336-343.

Lozinsky, V. I. & Damshkaln L. G., "Study of Cryostructuration of Polymer Systems. XVII. Poly(vinyl alcohol) Cryogels: Dynamics of the Cryotropic Gel Formation," Journal of Applied Polymer Science, vol. 77, 2017-2023 (2000).

Marolongo, M., et al, "Novel Hydrogel Copolymers for Intervertebral Disc Replacement," Sixth World Biomaterials Congress Transactions, 2000.

Mongia, N.K., et al, "Mucoadhesive poly(vinyl alcohol) hydrogels produced by freezing/thawing processes: Applications in the development of wound healing systems," J. Biomater. Sci, Polymer Edn, vol. 7, No. 12, pp. 1055-1064 (1996).

Narasimhan, B. & Peppas, N.A., "Molecular Analysis of Drug Delivery Systems Controlled by Dissolution of the Polymer Carrier," Journal of Pharmaceutical Sciences, vol. 86, No. 3, Mar. 1997.

Norton, B. K, et al, "Mechanical Evaluation of a Structural Hydrogel for Use as a Spinal Disc Nucleus," Sixth World Biomaterials Congress Transactions, 2000.

Ogata, N., et al., "Poly(vinyl alcohol)-clay and Poly (ethylene oxide)-clay Blends Prepared Using Water as Solvent," Journal of Applied Polymer Science, vol. 66, 573-581 (1997).

Peppas, N.A. & Stauffer, S. R., "Reinforced uncrosslinked poly (vinyl alcohol) gels produced by cyclic freezing-thawing processes: a short review," Journal of Controlled Release, 16 (1991) 305-310.

Strawhecker, K.E. & Manias E., "AFM of Poly(vinyl alcohol) Crystals Next to an Inorganic Surface," Macromolecules, 2001, 34, 8475-8482.

Strawhecker, K.E. & Manias, E., "Structure and Properties of Poly(vinyl alcohol)INA+Montmorillonite Nanocomposites," Chem. Mater, 2000, 12, 2943-2949.

Takahashi, N., et al, "Effects of cononsolvency on gelation of poly(vinyl alcohol) in mixed solvents of dimethyl sulfoxide and water," Polymer 44 (2003) 4075-4078.

Wilke, H-J, et al, "Prosthetic Disc Nucleus Restores the Flexibility and Disc Height of a Disc After Nucleotomy," Sixth World Biomaterials Congress Transactions, 2000.

Yamaura K., et al, "Gels of Syndiotacticity-Rich Poly(vinyl Alcohol)-Water/Dimethyl Sulfoxide or—Water/Ethylene Glycol Solutions," Journal of Applied Polymer Science, vol. 34, 2347-2354 (1987).

Yamaura, K. et al., "Properties of Gels Obtained by Freezing/Thawing of Poly(vinyl Alcohol)/Water/Dimethyl Sulfoxide Solutions," Journal of Applied Polymer Science, vol. 37, 2709-2718 (1989).

Yokoyama, F., et al, "Morphology and structure of highly elastic poly (vinyl alcohol) hydrogel prepared by repeated freezing-and-melting," Colloid & Polymer Sci 264: 595-601 (1986).

Yu, Y, et al, "Preparation and properties of poly (vinyl alcohol) clay nanocomposite materials," Polymer 44 (2003) 3553-3560.

Bodugoz-Senturk et al., Biomaterials 29: 141-149 (2008).

Choi et al., Biomaterials 28: 772-780 (2007).

\* cited by examiner

SYSTEMS AND METHODS FOR CONTROLLING AND FORMING POLYMER HYDROGELS

CROSS REFERENCES TO RELATED APPLICATIONS

The present application is a divisional of U.S. patent application Ser. No. 10/771,852 filed Feb. 2, 2004, which issued as U.S. Pat. No. 7,485,670. U.S. patent application Ser. No. 10/631,491, filed Jul. 31, 2003 and U.S. Provisional Application No. 60/400,899, filed Aug. 2, 2002 are incorporated by reference.

BACKGROUND OF THE INVENTION

Lower back pain affects over 65 million people in the United States with an estimated 12 million of these cases arising from degenerative disk disease. The back is particularly susceptible to damage and disease due to its complex structure. The spine is a complex structure of articulated bone and cartilage comprised of a column of vertebrae separated by vertebral disks (FIG. 1). These vertebral disks act as an intervening cushion to mitigate and distribute loads transferred along the spinal column.

The anisotropic structure of the intervertebral disk efficiently achieves the appropriate mechanical properties required to cushion complex spinal loads. The inner viscoelastic material, termed the nucleus pulposus, occupies 20-40% of the total disk cross-sectional area. The nucleus usually contains between 70-90% water by weight. The nucleus is composed of hydrophilic proteoglycans that attract water into the nucleus and thus generate an osmotic swelling pressure ranging between 0.1-0.3 MPa, which supports the compressive load on the spine. The nucleus is constrained laterally by a highly structured outer collagen layer, termed the annulus fibrosus (FIG. 1). The nucleus pulposus is always in compression, while the annulus fibrosus is always in tension. Although it comprises only one third of the total area of the disk cross-section, the nucleus supports 70% of the total load exerted on the disk. The intervertebral disk becomes less elastic with age, reaching the elasticity of hard rubber in most middle-aged adults as the nucleus loses water content. This water loss will also cause the disk to shrink in size and will compromise its properties.

In degenerative disk disease, the nucleus pulposus can become distorted under stress, resulting in the extrusion of part of the pulposus out through the annulus fibrosus, causing pressure against the surrounding nerves. This process is called herniation. The damage to the disk can often be irreversible if part of the pulposus is lost. The majority of disk injuries occur in the lumbar region, and the most common area of disease occurs at L4/L5 and L5/S1.

A laminectomy (surgical removal of part of a herniated disk—typically the nucleus pulposus) may be performed to relieve pressure on local neural tissue. This approach is clearly a short-term solution, given that the load bearing ability of the nucleus would be reduced with loss of material. Despite this, over 200,000 laminectomies are performed each year, with a success rate of 70-80%.

Arthrodesis or fusion is a more permanent method for surgically treating degenerative disk disease. Fusion is accomplished with or without internal fixation. While internal fixation has become increasingly popular, this technique has its share of complications. Fracture, neurological damage, and osteoporosis have been observed in patients who have undergone internal fixation fusions. The ability of the bone to fuse will vary from patient to patient, with the average likelihood of success ranging from 75-80%. Spinal fusion will cause stiffness and decreased motion of the spine. Additionally, fusion can also put stress on adjacent vertebrae in the spine, which can accelerate disease in adjacent disks and lead to additional back surgery.

A successfully designed artificial disk would replace a worn out disk while protecting patients from incurring problems at an adjacent level of the spine. Several artificial disk prostheses have been proposed in the prior art. Many of these prosthesis attempt complete replacement of the disk, including the nucleus and the annulus fibrosus. Given that the intervertebral disk is a complex joint with multi-directional loading, the design of a prosthesis that mimics the articulation and mechanical behavior of a natural disk is extraordinarily difficult. For example, when the body is supine, compressive loading on the third lumbar disk is 300 N, rising to 700 N in an upright stance, then to 1200 N when bending forward by 20°. Additionally, moments of 6 N-m are often achieved during flexion and extension, with up to 5° of rotation. For adequate safety, a preferred compressive strength of the entire disk is 4 $MN/m^2$.

The most extensive experience to date with a complete disk replacement is that obtained with the SB Charité III prosthesis. This prosthesis has been used extensively in Europe since 1987, and has been implanted into over 3,000 patients. The SB III is designed with a polyethylene spacer placed between two cobalt chromium endplates. Two year follow-up studies have shown good clinical success in patients. Another study concerned a complete disk prosthesis consisting of a polyolefin core reinforced with carbon black, which is attached to two titanium plates. Preliminary results are not promising, since the core fractured in 2 of the implants.

Both of the examples presented above serve to indicate that there is considerable commercial effort being expended in the development of artificial disks. However in both cases the mechanical equivalence of these components to the human intervertebral disks is somewhat doubtful and the long-term clinical prognosis is still unclear.

As an alternative to the complete replacement of intervertebral disks, the nucleus pulposus alone can be replaced, leaving the annulus fibrosus intact. This approach is advantageous if the fibrosis is intact, in that it is less invasive, and the annulus can be restored to its natural fiber length and fiber tension. In replacing the nucleus, it is desirable to find a material that is similar in properties to the natural nucleus. The prior art describes bladders filled with air, saline, or a thixotropic gel. To prevent leakage, the membrane material comprising the bladder must be impermeable, which inhibits the natural diffusion of body fluid into the disk cavity, preventing access to necessary nutrients.

To generate a more natural disk replacement material, several research groups have investigated polymeric hydrogels as a possible replacement for the nucleus pulposus. Hydrogels are good analogs for the nucleus pulposus, in that they typically possess good viscoelastic properties and can offer good mechanical behavior. Additionally, they contain a large amount of free water, which permits a prosthesis made from a hydrogel to creep under compression and handle the cyclical loading without loss of elasticity, similar to a natural nucleus pulposus. The water permeability of these materials also allows diffusion of body fluid and nutrients into the disk space. Control of this pore structure, and the consequent control of the nutrient access to all parts of the implant, may be critical for future prosthetic implants.

Others have investigated the use of polyacrylonitrile-polyacrylamide multiblock copolymers encased in a jacket made from ultra high molecular weight polyethylene fibers. These systems absorb up to 80% of their weight in water. Polyvinyl alcohol (PVA) and copolymers of PVA and poly vinyl pyrrolidone (PVP) have produced prostheses with mechanical properties similar to natural disks. These materials have the additional advantage of having clinical success in other medical devices. Gels formed from PVA are usually prepared via a freeze-thaw process or via external crosslinking agents. In addition, hydrogel-based nuclei can contain therapeutic drugs which slowly diffuse out after implantation. Although no clinical data is currently available for these materials, biomechanical testing on cadaver joints has shown similar mechanical properties to natural disks

SUMMARY OF THE INVENTION

In preferred embodiments, the present invention provides methods of controlling the gelation kinetics of vinyl polymers. These methods include, in preferred embodiments, controllably making a vinyl polymer hydrogel having desired physical properties without chemical cross links or radiation. The gelation process is modulated by controlling, for example, the temperature of a resultant vinyl polymer mixture having a gellant (also spelled as gelant) or using active ingredients provided in an inactive gellant complex.

Preferred embodiments include an injectable hydrogel such as for example, for nucleus pulposus augmentation using minimally-invasive surgical implantation of prosthetics fabricated in situ. The hydrogel in accordance with preferred embodiments of the present invention conform to the region of interest, for example, vertebral surfaces in a joint space. The load bearing hydrogels formed by in situ gelation methods of the present invention minimizes damage to, for example, the annulus fibrosus. In accordance with a preferred embodiment, the method of manufacturing a vinyl polymer hydrogel includes the steps of providing a vinyl polymer solution comprising a vinyl polymer dissolved in a first solvent; heating the vinyl polymer solution to a temperature elevated above the melting point of the physical associations of the vinyl polymer, mixing the vinyl polymer solution with a gellant, wherein the resulting mixture has a higher Flory interaction parameter than the vinyl polymer solution; inducing gelation of the mixture of vinyl polymer solution and gellant; and controlling the gelation rate to form a viscoelastic solution, wherein workability is maintained for a predetermined period, thereby making a vinyl polymer hydrogel having the desired physical property. In further preferred embodiments, the present invention provides physically crosslinked hydrogels produced by controlled gelation of viscoelastic solution wherein workability is maintained for a predetermined period. In another aspect, the present invention provides kits for use in repairing intervertebral disks or articulated joints including components that form the vinyl polymer hydrogel and a dispenser.

In certain preferred embodiments, the step of providing a vinyl polymer solution typically includes the step of dissolving the vinyl polymer in the first solvent. The step of mixing the vinyl polymer solution with a gellant may precede or follow the step of heating the vinyl polymer solution to a temperature elevated above the melting point of physical associations of the vinyl polymer.

The desired physical property typically includes at least one of light transmission, gravimetric swell ratio, shear modulus, load modulus, loss modulus, storage modulus, dynamic modulus, compressive modulus, cross-linking and pore size. In preferred embodiments, the desired physical property is physical cross-linking.

In preferred embodiments, the vinyl polymer is selected from the group consisting of polyvinyl alcohol, polyvinyl acetate, polyvinyl pyrrolidone and mixtures thereof. Preferably the vinyl polymer is highly hydrolyzed polyvinyl alcohol of about 50 kg/mol to about 300 kg/mot molecular weight. In preferred embodiments, the vinyl polymer is highly hydrolyzed polyvinyl alcohol of about 100 kg/mol molecular weight. Typically the vinyl polymer solution is about 1 weight percent to about 50 weight percent solution of polyvinyl alcohol based on the weight of the solution. In preferred embodiments, the vinyl polymer solution is about 10 weight percent to about 20 weight percent solution of polyvinyl alcohol based on the weight of the solution.

In certain preferred embodiments, the method includes the step of further contacting the viscoelastic solution with a gellant, typically to modify the physical or chemical properties of the resulting gel. This method is suitable for producing a local modification in the physical properties of the gel, such as to maintain the gel in place within a body cavity, such as a space within an intervertebral disk.

In preferred embodiments, the first solvent is selected from the group consisting of deionized water, dimethyl sulfoxide, an aqueous solution of a $C_1$ to $C_6$ alcohol and mixtures thereof. Preferably the gellant is more soluble than the vinyl polymer. In certain preferred embodiments, the vinyl polymer is introduced into an aqueous solution of a gellant.

Typically, the Flory interaction parameter of the mixture of vinyl polymer solution and gellant ranges from 0.25 to 1.0. In preferred embodiments, the Flory interaction parameter of the mixture is at least 0.5, more preferably about 0.25 to about 0.5.

Typically the gellant is selected from the group consisting of salts, alcohols, polyols, amino acids, sugars, proteins, polysaccharides, aqueous solutions thereof, and mixtures thereof. In preferred embodiments, the gellant is selected from the group consisting of chondroitin sulfate, dermatan sulfate, hyaluronic acid, heparin sulfate and mixtures thereof. In other preferred embodiments, the gellant is selected from the group consisting of biglycan, syndecan, keratocan, decorin, aggrecan and mixtures thereof. In further preferred embodiments, the gellant is an alkali metal salt, most preferably sodium chloride.

The gellant may be added as a dry solid or in solution. For example, solid NaCl can be added to an aqueous solution of vinyl polymer, or added as an aqueous solution of sodium chloride from about 1.5 molar to about 6.0 molar, more preferably about 2.0 molar to about 6.0 molar. In further preferred embodiments, the gellant is an aqueous solution of an alcohol chosen from the groups consisting of methanol, ethanol, i-propanol, t-propanol, t-butanol and mixtures thereof.

The gellant may be in an active form or an inactive form when it is mixed with the vinyl polymer solution. In preferred embodiments, the step of inducing gelation of the viscoelastic solution includes the step of activating the gellant. Preferably, the inactive gellant is activated by a controllable trigger event.

In certain preferred embodiments, the inactive gellant is a macromolecule and the active gellant comprises fragments of a macromolecule that are released by cleavage of the macromolecule. In some embodiments, the cleavage of the macromolecule is enzymatic cleavage; a preferred macromolecule is a physiological substrate of the selected enzyme. In preferred embodiments, the macromolecule is selected from the group consisting of chondroitin sulfate, dermatan sulfate, keratan sulfate, hyaluronic acid, heparin, heparin sulfate and mixtures thereof and the enzyme is selected from the group consisting of chondroitinase ABC, chondroitinase AC, chondroitinase B, testicular hyaluronidase, hyaluron lyase, heparinase I/III and mixtures thereof. In other preferred embodiments, the macromolecule is selected from the group consisting of biglycan, syndecan, keratocan, decorin, aggrecan, perlecan, fibromodulin, versican, neurocan, brevican and mixtures thereof and the enzyme is selected from the group including, for example, without limitation, aggrecanase and mixtures thereof.

In other embodiments, macromolecule can be thermally denaturable; in such embodiments, a preferred macromolecule is collagen. Alternatively, cleavage of the macromolecule is by irradiation with electromagnetic radiation or particulate radiation.

In further preferred embodiments, the inactive gellant is a bad solvent sequestered in a vesicle, a liposome, a micelle or a gel particle. In some preferred embodiments, the liposome is a phototriggerable diplasmalogen liposome. In alternate preferred embodiments, the liposome undergoes a phase transition at about the body temperature of a mammal. Preferably, the liposome includes, without limitations a mixture of dipalmitoylphosphatidylcholine and dimyristoylphosphatidylcholine.

In further preferred embodiments, the inactive gellant is associated with a gel particle that is in an active form up on undergoing a phase transition at about the body temperature of a mammal. In such embodiments, the gel particle suitably comprises a polymer selected from the group consisting of poly(N-isopropyl acrylamide-co-acrylic acid), N-isopropylacrylamide, hyaluronic acid, pluronic and mixtures thereof. In other preferred embodiments, the gel particle releases its contents upon undergoing degradation.

Typically, the rate of gelation is controlled to provided an adequate period of workability needed for further processing of the viscoelastic solution, including injecting, molding or calendaring. In preferred embodiments, the viscoelastic solution is injected into an actual or potential space in the body of a mammal. In particularly preferred embodiments, the viscoelastic solution is injected into an intervertebral disk or an articulated joint, such as a hip or knee. The hydrogel can be retained within the body space by virtue of general physical properties or by its local physical properties at the injection site. In preferred embodiments, desired local physical properties can be adjusted by a further addition of gellant near the injection site. In other preferred to embodiments, the hydrogel can be retained within the body space by the use of known medical devices to seal, reinforce or close the injection site or other defect of the body cavity. Suitable such devices are disclosed in published International Patent Applications WO 01/12107 and WO 02/054978, which are hereby incorporated by reference in their entirety.

In other preferred embodiments, the step of processing includes covering a burn or a wound.

The preferred embodiments of the present invention provide methods of making a gel and controlling a property of the gel. In accordance with a preferred embodiment of the present inventions, a method for making a gel includes comprising dissolving a vinyl polymer in a first solvent to form a vinyl polymer solution and introducing the vinyl polymer solution in a volume of a second solvent to cause gelation, the second solvent having a higher Flory interaction parameter at a process temperature than the first solvent. The Flory interaction parameter ($\chi$) is dimensionless and depends on, for example, temperature, concentration and pressure. Solvents can be characterized as having a low $\chi$ value or solvents having a higher $\chi$ value wherein $\chi=0$ corresponds to a solvent which is similar to a monomer. A solvent having a higher $\chi$ value is characterized as a solvent that causes a gelation process at a temperature. A thetagel, in accordance with the present invention, is formed by using a second solvent having a Flory interaction parameter that is sufficient to cause gelation.

Preferably the second solvent used in the preferred embodiment has a Flory interaction parameter in the range of 0.25 to 1.0. Typically, first and second solvent characteristics are chosen to allow use of the method of the preferred embodiment at room temperature or at body temperature of a mammal. The gel produced by the method of the invention has physical cross-linking, and is substantially free of chemical crosslinking agents. In a preferred embodiment, the vinyl polymer is polyvinyl alcohol.

In some embodiments, a plurality of cycles of contacting the vinyl in an immersion solvent (second solvent) and contacting with the first solvent are performed. Alternatively, the method may include subjecting the gel to at least one freeze-thaw cycle. The polyvinyl alcohol (PVA) hydrogels thus may be both a thetagel and a cryogel. Partial gelling can be accomplished with either method and then completed using the other, or even alternating between the two methods.

While the examples and discussion herein are directed towards vinyl polymers and in particular PVA hydrogels, thetagels can be made in a similar manner using any polymer that possesses the appropriate kind of phase diagram as described hereinafter with respect to the Flory interaction parameter. A mechanical force can be applied to the gel during the gelling process, changing the manner in which it gels and alternatively producing oriented gelation.

In several embodiments, the vinyl polymer is highly hydrolyzed polyvinyl alcohol of about 50 kg/mol to about 300 kg/mol molecular weight. In other embodiments, the vinyl polymer is highly hydrolyzed polyvinyl alcohol of about 100 kg/mol molecular weight. The vinyl polymer solution is about 1 weight percent to about 50 weight percent solution of polyvinyl alcohol based on the weight of the solution. Preferably, the vinyl polymer solution is about 10 weight percent to about 20 weight percent solution of polyvinyl alcohol based on the weight of the solution.

The first solvent is selected from the group of solvents having a low $\chi$ value that is not sufficient to enable gelation, i.e., solvents in which the energy of interaction between a polymer element and a solvent molecule adjacent to it exceeds the mean of the energies of interaction between the polymer-polymer and the solvent-solvent pairs, as discussed below. In several embodiments, the first solvent is selected, without limitation, from the group consisting of deionized water, dimethyl sulfoxide, an aqueous solution of a $C_1$ to $C_6$ alcohol and mixtures thereof.

In general, the immersion solution comprises a solvent having a high or sufficient $\chi$ value that enables gelation. In some preferred embodiments, the immersion solution is an aqueous solution of a salt of an alkali metal, typically sodium chloride. In other embodiments, the immersion solution is an aqueous solution of a $C_1$ to $C_6$ alcohol, typically an aqueous solution of an alcohol chosen from the groups consisting of methanol, ethanol, i-propanol, t-propanol, t-butanol and mixtures thereof. In certain embodiments, the immersion solution is an aqueous solution of methanol.

In general, the vinyl polymer gels of the present invention can be made in-situ for applications such as filters, microfluidic devices or drug release structures in situations in which freeze-thaw gelation may be difficult or impossible to execute.

In one embodiment, the vinyl polymer solution is placed in a chamber having at least two sides and a membrane. The membrane has properties that contain the vinyl polymer while providing access to small molecules and solvents.

In some embodiments, the vinyl polymer solution is separated by the membrane from at least two different immersion solvents, typically a first immersion solvent and a second immersion solvent. In some embodiments, the first immersion solvent is an aqueous solution of sodium chloride from about 1.5 molar to about 6.0 molar. In some embodiments, the second immersion solvent is an aqueous solution of sodium chloride from about 2.0 molar to about 6.0 molar. In other embodiments, the first immersion solvent is a 1.5 molar aqueous solution of sodium chloride and the second immersion solvent is an aqueous solution of sodium chloride from about 2.0 molar to about 6.0 molar. In such embodiments, a gradient in chemical potential is formed across the vinyl polymer solution between at least two different immersion solvents. In one embodiment, a gradient in chemical potential is formed across the vinyl polymer solution of about 4 $mol \cdot cm^{-1}$.

In general, a gradient of a property is formed across the vinyl polymer gel that corresponds to the gradient in chemical potential formed across the vinyl polymer solution. Typically, the property is at least one of light transmission, swell ratio, shear modulus, load modulus, loss modulus, storage modulus, dynamic modulus, compressive modulus, cross-linking and pore size.

In some embodiments, one or both immersion solvents are changed in a temporal pattern to modulate the spatial gradient of a physical property. Such temporal cycling is done on a time scale shorter than the diffusion time to make an inhomogeneous gel. In this way, gels can be produced with a similar set of properties on the edges or peripheral region and another set of properties in the central region, such as greater cross-linking in the peripheral region as compared with the central region. Temporal cycling of immersion solvents can also be used to modify the structure of the gel, for example, pore size, for production of filters. In such filters, small, locally varying pore size may be useful for some forms of chromatography (through size exclusion) or any other filtering application that requires pore size control.

Additional compounds can be combined in the physically cross-linked gel, including but not limited to, ionic or non-ionic species such as hyaluronic acid, polyacrylic acid and therapeutic agents.

In one embodiment, the invention provides a physically cross-linked hydrogel comprising at least about 10 weight percent poly(vinyl alcohol) solution gelled by immersion in about 2 to about 3 molar sodium chloride wherein the hydrogel is about 14 percent to about 21 percent physically cross-linked. In such an embodiment the final gel comprises about 12 to about 29 percent poly(vinyl alcohol).

The preferred embodiments of the present invention also provide articles of manufacture comprising a vinyl polymer gel having at least one gradient of mechanical properties, PVA thetagels may be used as a biocompatible load bearing or non-load bearing material for replacement, repair or enhancement of tissue. In general, PVA thetagels can replace PVA cryogels in applications where PVA cryogels are used.

In one embodiment, a one-piece prosthetic intervertebral disk is made comprising a polyvinyl polymer hydrogel wherein the distribution of mechanical properties of the one-piece prosthetic intervertebral disk approximates the spatial distribution of the mechanical properties of the combination of the nucleus pulposus and the annulus fibrosis of the natural intervertebral disk.

High compression PVA thetagels can be made by placing PVA in a reverse osmosis membrane with NaCl and then making the outside concentration of NaCl quite high to compress PVA/NaCl. The NaCl concentration will climb as water leaves the reverse osmosis membrane gelling the PVA at high pressure. The concentration of PVA can be modified by the ratio of NaCl to PVA inside the reverse osmosis membrane.

In a preferred embodiment, gel microparticles can be made through gelation during agitation or by dropping blobs of fluid into a crosslinking solvent, such as the immersion solution.

In a preferred embodiment, gels can be embedded with particles that degrade (or do not adsorb) to "imprint" a pattern ("empty spaces") on the gel or as the drug release centers. Embedding neutrally charged polymers of varying molecular weights can be used to "space fill" the gel. These polymers are removable after the process, leaving a controlled pore structure. Materials that are sensitive to freeze-thaw cycles can be encapsulated. The gels can be embedded with particles or polymers that are electrostatically charged to provide extra repulsion at high compressions but are collapsed in high salt. Such embedded particles can be those that are active in some manner (e.g. for catalyses). Hydroxyapatite particles or other osteoinductive particles, agents, and similar moieties can be embedded to encourage bony ingrowth for possible cartilage replacement.

In a preferred embodiment, poly(vinyl alcohol) gels can be used to contain and release bio-active compounds such as growth factors, fibronectin, collagen, vinculin, chemokines and cartilage including therapeutic agents. The teachings with respect to incorporation of therapeutic agents of U.S. Pat. Nos. 5,260,066 and 5,288,503 are herein incorporated in their entirety. Contained compounds such as therapeutic agents or drugs can be released over time to modulate the local growl of normal tissues such as bone, blood vessels and nerves or tumors.

Temporal modulation of immersion solvents can produce thetagels in accordance with the preferred embodiment with appropriate structure and physical properties for containing and releasing drugs and other bioactive molecules. In one embodiment, an outer skin is formed that is highly crosslinked and an inner layer containing the drug/active agent is only weakly crosslinked. In such an embodiment, the outer skin is the rate limiting component and has a constant release rate. Thus, drug release in accordance with a preferred embodiment includes the release profile that is tunable by controlling the spatial gradient in PVA crosslinking.

In one embodiment, the present invention provides a method of controllably modulating the mechanical properties and structure of hydrogels. In a preferred embodiment, the present invention provides articles of manufacture with one or more gradients of mechanical properties that more closely match the existing gradients of such properties in natural structures. In one embodiment the invention provides prosthetic hydrogel articles of manufacture that mimic the mechanical behavior of natural structures. In a preferred embodiment, the invention provides polyvinyl alcohol prosthetic intervertebral disks that mimic gradients of mechanical properties found in the natural intervertebral disks. In another preferred embodiment, the invention provides a one-piece prosthetic intervertebral disk that mimics the spatial distribution of the mechanical properties of the nucleus pulposus plus annulus fibrosis of the natural intervertebral disk.

In a preferred embodiment, particulates may also be added to the gel. As described hereinbefore, particulates can be added to create a controlled pore structure. Further, in accordance with another preferred embodiment, particulates can be added to provide a particular nanostructured gel. The particles can be either charged or uncharged and allow PVA crystals to nucleate at the surface of the particles. Particles that can be added include, but are not limited to, inorganic or organic colloidal species such as, for example, silica, clay, hydroxyapatite, titanium dioxide or polyhedral oligomeric silsesquioxane (POSS).

In accordance with another preferred embodiment, particles are added to provide a charge effect to change the compressive modulus of the gel, and preferably increase the compressive modulus. This embodiment can use a thetagel having added particles. Upon compressing the gel in a salt solution, a structure having particles with close packing while shielding their charges results. Upon rehydrating with, for example, deionized (DI) water, the charge fields expand and results in a gel in tension. This allows the gel to approximate physical properties of cartilage, for example, at high charged particulate loads.

In accordance with another preferred embodiment, particulates are added to the gel structure to provide mechanical properties such as, for example, wear resistance. The addition of hardened glass (silica) or different clays can provide wear resistance to the gels.

In accordance with another preferred embodiment of the present invention, a method for making a gel and controlling a property of the gel includes forming a thetagel as described hereinbefore by using a first solvent to form a vinyl polymer solution and subsequently introducing a volume of a second solvent to cause gelation, followed by promoting dehydration to controllably structure the gel. This method results in uniformly structuring the gel and homogenizing the physical crosslinking of the PVA thetagel. This structure can be achieved by immersing the contained PVA solution into a solvent which has a Flory interaction parameter that is higher than the theta point for the PVA solvent pair, and subsequently immersing the contained PVA in another solvent having a Flory interaction parameter lower than the theta point for the PVA solvent pair. The process can continue with successive decreases in the Flory interaction parameter until the desired interaction parameter value for the gel is reached.

In another method in accordance with a preferred embodiment of the present invention, the PVA solution can be subjected to a gradually changing solvent quality through a similar range of electrolyte concentrations by the gradual addition of a concentrated NaCl solution to deionized water such that the change of the salt concentration is slower, or equal, to the diffusion process of the gel.

In accordance with another preferred embodiment of the present invention, the PVA solution may be subjected to at least one freeze-thaw cycle to fix the gel into a particular shape and then be immersed in a series of solutions with successively higher Flory interaction parameters until the final desired Flory parameter is reached. Alternatively, the PVA solution is subjected to the one or more freeze-thaw cycles after being immersed in a solution of 2 M NaCl.

In one preferred embodiment, nanoparticles are dispersed into solutions of PVA. The solvent may be water, dimethyl sulfoxide (DMSO), methanol or any other solution that exhibits a Flory interaction parameter that is lower than the theta point for the PVA solvent pair during solution preparation. The PVA/nanoparticle mixture is then subjected to at least one freeze-thaw cycle. Subsequent to the freeze-thaw cycling, the gelled PVA is immersed in a solvent that has a Flory interaction parameter near or higher than the theta point for the PVA/solvent pair to induce further physical crosslinking of the PVA/nanoparticle mixture.

Another aspect of the embodiments of the present invention further provide methods of controlling the rate of gelation of polymer gels by changing in the manner in which the polymer molecules interact. By controlling the rate of gelation, a "window" of time that allows the relatively slowly gelling PVA solution to be manipulated or worked, for example, by injection, molding or any other processing step that may be dependent on the flow of the gelling PVA solution. In preferred embodiments, the gelling PVA solution is injected into a region of interest such as a body cavity and gels in situ to form a PVA product. Preferred body cavities include the nucleus pulposus and a normal or pathological void within a joint.

In preferred embodiments, the rate of gelation can be controlled by holding the polymer, preferably PVA, above its crystallization temperature, thus preventing gelation even if the solvent quality is poor. In other preferred embodiments, the rate of gelation can be controlled by using a second solvent that can be triggered to change from good to bad. In some preferred embodiments, the quality of the solvent can be changed by disruption of micelles. In other preferred embodiments, the quality of the solvent can be changed scission of high molecular weight molecules. In further preferred embodiments, a poor solvent is used in combination with process temperatures that accelerate the gelation process.

The foregoing and other features and advantages of the systems and methods for controlling and forming polymer gels will be apparent from the following more particular description of preferred embodiments of the system and method as illustrated in the accompanying drawings in which like reference characters refer to the same parts throughout the different views. The drawings are not necessarily to scale, emphasis instead being placed upon illustrating the principles of the invention.

BRIEF DESCRIPTION OF THE DRAWINGS

FIG. 22A, zero minutes; FIG. 22B, 15 minutes, FIG. 22C, 2 hours, under a mineral oil protective layer; and FIG. 22D, one day, out of a jar.

FIG. 23A, zero minutes; FIG. 23B, 20 minutes; FIG. 23C, 1 hour; FIG. 23D, 2 hours; and FIG. 23E, 17 hours.

FIG. 24E, one hour) or on shaved ice (FIG. 24D, 15 minutes; FIG. 24F, one hour).

FIG. 25A, cooled one hour at room temperature and stored 12 hours at room temperature; FIG. 25B, cooled one hour on ice and stored 12 hours at room temperature; FIG. 25C, cooled one hour at room temperature and stored one month at room temperature; FIG. 25D, cooled one hour on ice and stored one month at room temperature; FIG. 25E, the PVA gel of FIG. 25C, oriented to show water released due to syneresis; and FIG. 25F, the PVA gel of FIG. 25D, oriented to show water released due to syneresis.

FIGS. 26A-26D illustrate a PVA hydrogel prepared by adding NaCl to aqueous 10 wt % PVA solution at 95 degrees Celsius while mixing to make a final concentration of 2.1 M NaCl, in accordance with a preferred embodiment of the present invention, wherein FIG. 26A shows a mold formed by a chilled polyethylene liner and the matching ball from a total hip replacement joint, FIG. 26B shows the mold after filling the chilled polyethylene liner with the PVA solution and putting the matching ball in place, FIG. 26C shows the molded PVA in the polyethylene liner after one hour in air at room temperature followed by one hour in deionized water at room temperature; and FIG. 26D shows the molded PVA product removed from the polyethylene liner.

FIG. 27A shows a PVA hydrogel formed by adding warm CS solution at about 80 degrees Celsius to a aqueous 10 wt % PVA solution at about 60 degrees Celsius to produce a 5 wt % PVA, 7 wt % CS mixture and FIG. 27B shows a PVA hydrogel formed by adding 600 mg CS directly to 10 ml aqueous 10 wt % PVA solution.

DETAILED DESCRIPTION OF PREFERRED EMBODIMENTS

Figure 1A:
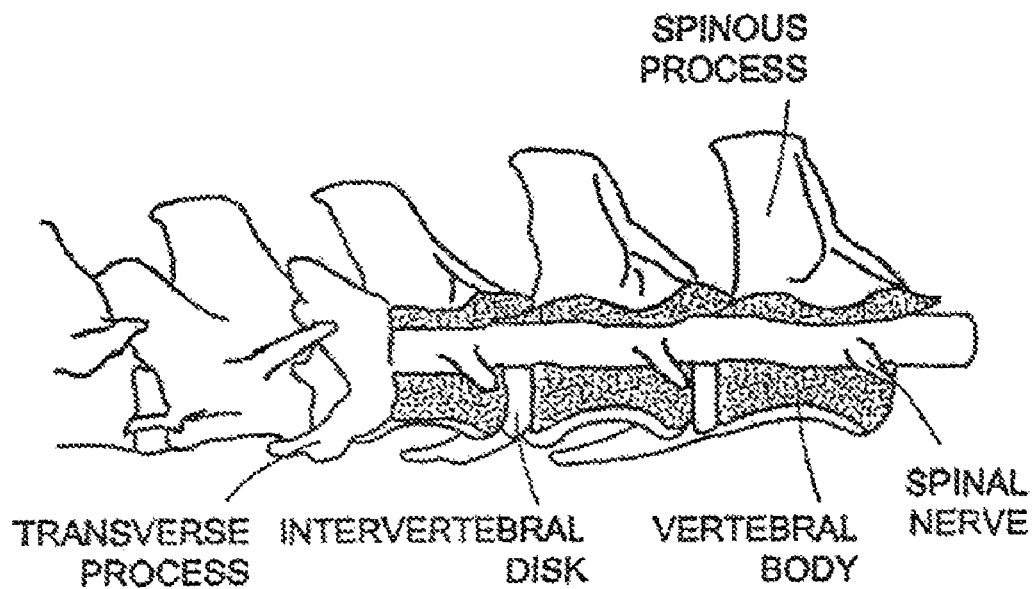
FIGS. 1A and 1B are a diagrammatic representation of spinal anatomy showing transverse process, spinous process and vertebral body of the vertebral bones, the spinal cord and spinal nerves, and the nucleus pulposus of the intervertebral disks. The annulus fibrosis of the intervertebral disk surrounds the nucleus pulposus on lateral, anterior and posterior sides.

The preferred embodiments of the present invention are directed at the generation of uniform PVA hydrogels without chemical crosslinks or irradiation to produce a biocompatible material suitable for use as, for example, an intervertebral disk prosthesis. Further, a preferred embodiment of the present invention includes a method used to create the PVA gels that result in a new class of PVA hydrogels which can be designed for specific applications to have a potentially large range of mechanical properties, being controllable, and which can be engineered with gradients in structure and physical properties.

As used herein, "theta solvent" refers to a solvent that yields, at the theta temperature, solutions of a polymer in the theta state. Theta solvents may be composed of a single solvent or mixture of two solvents, a mixture of a solvent and a nonsolvent, or even a mixture of two nonsolvents in the case of co-solvency as described by Elias, H. G., "Theta Solvents," in Brandrup, J, and E. H. Immergut, Polymer Handbook $3^{rd}$ Ed., John Wiley and Sons, New York, 1989, the teachings of which are herein incorporated by reference in their entirety.

As used herein, "gelation" refers to the formation of permanent physical crosslinks due to the crystallization of the PVA. This is in contrast to some of the literature in which gelation refers to the point at which the polymer associates, and need not be followed by the crystallization that forms a permanent link.

As used herein, "associate" refers to a thermodynamically, or solvent, driven process whereby the polymer (or other species) "prefers" to be in an environment similar to itself, rather than in close proximity to another species. This association of the polymer locally then necessarily leads to a "phase separation" that may or may not lead to an inhomogeneous solution.

While not being held to a particular theory, it is thought that forcing poly(vinyl alcohol) polymer chains in solution into close proximity using a theta solvent through a spinodal decomposition mechanism results in the formation of a physical association that is resistant to dissolution. As used herein, spinodal decomposition refers to a clustering reaction in a homogeneous, supersaturated solution (solid or liquid) that is unstable against infinitesimal fluctuations in density or composition. The solution therefore separates spontaneously into two phases, starting with small fluctuations and proceeding with a decrease in the Gibbs energy without a nucleation barrier.

The methodology used in the present invention generates a PVA hydrogel employing the controlled use of solvents having a $\chi$ value sufficient to cause gelation to force the PVA chains to physically associate. To prevent random "crashing out" of the PVA, it is critical that the solvent quality is controlled carefully, and, in particular for larger components, that the solvent "front" enters the PVA solution in a controlled manner. For example, NaCl/deionized (DI) water and methanol/deionized water solutions at temperatures and concentrations in the neighborhood of their "theta" value for PVA were used to force the physical association and subsequent gelling of the PVA. Gels formed in this way are called "thetagels" herein.

In general, by controlling solvent quality one can create a "window" of time that allows the relatively slowly gelling PVA solution to be manipulated or worked. This manipulation includes, without limitation, injection or molding or any other conceivable processing step.

The methods are applicable to the creation of materials for use in medical, biological and industrial areas including the controlled delivery of agents (which may include proteins, peptides, polysaccharides, genes, DNA, antisense to DNA, ribozymes, hormones, growth factors, a wide range of drugs, imaging agents for CAT, SPECT, x-ray, fluoroscopy, PET, MRI and; ultrasound), generation of load bearing implants for hip, spine, knee, elbow, shoulder, wrist, hand, ankle, foot and jaw, generation of a variety of other medical implants and devices (which may include active bandages, trans-epithelial drug delivery devices, sponges, anti-adhesion materials, artificial vitreous humor, contact lens, breast implants, stents and artificial cartilage that is not load bearing (i.e., ear and nose)), any application where gradients (single or multiple) in mechanical properties or structure are required.

The mechanism of gel formation includes a phase separation usually considered to be a spinodal decomposition process followed by a crystallization mediated by hydrogen bonding in the PVA rich regions of the solution. The choice of the solvent is known to influence the freeze-thaw process. It is also known that some solvents can be used to gel PVA without dropping the temperature of the solution below the freezing point of the solvent. Solvents such as DMSO, ethylene glycol (EG), N-methyl-2-pyrrolidone (NMP), and gelatin have been used to gel PVA in ambient temperatures. The preferred embodiments of the present invention include the use of salt as a means of gelling a PVA solution, and the utility of manipulating and controlling the solvent quality during the gelation process.

An ideal polymer chain in a good solvent has no association behavior that leads to precipitation. As the solvent quality drops below the theta condition, the chains begin to prefer to associate until eventually the polymer phase separates. In an ideal polymer, there are no further interaction forces in the polymer chains, other than that provided through thermodynamic (solvent) forces, and the normal, reversible phase diagram thus applies. However, in PVA, there is a strong binding force driven by hydrogen bonding that results in a local crystallization of the chain. This crystallization can occur even when the solvent is "good." Although the chemical potential in a good solvent does not encourage association, random thermal motions do allow the chains to briefly contact and occasionally overcome this "solvation force". At this point, if the conditions are correct, as is the case for PVA, the chains will start to crystallize. This rate of initial contact to initiate crystallization depends on the solvent quality. Therefore, as the solvent quality is decreased, the probability of the PVA chain associating increases since this is driven by the affinity of the chain for itself, which is described by the solvent quality. As a result, rate of change of solvent quality is important, as has been observed by manipulation of temperature. Since this process is related to the solvent quality, it depends on temperature, concentration and pressure. Therefore, the gelling of the PVA must depend on time, and more importantly, a competition between the association "time" and the phase separation "time". This competition has been observed experimentally, resulting in different initial get structures depending on cooling rates and solvents, and in the aging of PVA gels.

Therefore controlling solvent quality by controlled solvent addition, or by temperature, pressure or any other relevant parameter allows one to control the rate of this association. Consequently, one desires to control the solvent quality of the system such that it is poor enough to accelerate the association rate by promoting the proximity of the chains while ensuring that the solvent is not so bad that the polymer falls out of solution before crystallization can occur. The optimal conditions for gel formation are likely to be in the range of $\chi=0.25$ to $0.5$, but even outside these values it is possible to produce gels. By balancing these competing effects, a polymer/solvent solution can be obtained that is still fluid but gels rapidly.

For a single solvent with its solvent quality varied by temperature, or pressure, control, the spinodal decomposition phase transition is accelerated by the decrease in solvent quality. For a ternary blend, the phase separation can be understood as either the PVA is poorly solvated by the (continuous) water/solvent B blend and thus phase separates under the identical mechanism as the single solvent system; or both the PVA and solvent B are solvated by water, but have varying miscibility with each other. These materials therefore behave like a binary blend and, therefore, phase separate. Although conceptually slightly different, the results are almost identical. The behavior of two good solvents that result in a poor solvent is known as co-nonsolvency. This approach provides the ability to mix the components externally and then inject the PVA solution into a region of interest such as a cavity wherein it subsequently gels. This ability to inject PVA and induce gelation in situ is especially suitable for nucleus replacement or augmentation of intervertebral disks (IVD), since the second solvent can be anything that has the required thermodynamic properties. This second solvent can be a long chain polymer, protein or other complex molecule, or an aqueous solution thereof, such as polyethylene oxide (PEO), a glycosaminoglycan (GAG) or gelatin or simpler molecules such as simply ionic species like salts, for example, NaCl or short chain molecules like poly(ethylene glycol), for example PEG 400, glycerin or amino acids like serine or glycine. Although higher molecular weight species are not commonly characterized as solvents, the underlying theory, as described by Flory, makes no distinction as to the length of the solvent molecule, although the final interaction parameter for the solvent/polymer pair is affected by the solvent size.

PVA is known to associate at room temperature in deionized (DI) water over long times. This is well below the theta transition of PVA in pure water of 97° C. The crystallites generated in both the freeze-thaw process, and the thetagel process as used herein have a melt peak near 60° C. In addition, most studies involving PVA require elevated temperatures of at least 80° C. to ensure that the PVA is fully "dissolved". These observations suggest that above this temperature the PVA no longer possesses the ability to crystallize, and hence behaves like an ideal polymer with respect to solvent quality. Consequently, it is recognized herein that if one can dissolve the PVA in a solution above this critical melt temperature there can be no crystallization, and hence no gelation, although there may be precipitation, or phase separation, due to simple association. If the solvent used is poor then there is some association through thermodynamic effects (and thus inhomogeneous precipitation may occur), but there can be no irreversible gelation that characterizes the PVA hydrogels. However, as soon as the temperature is lowered, crystallization can occur and the system can begin to gel. This gelation crystallization is still however rate limited, thus allowing the solution to be workable, even whilst below this temperature, and in a poor solvent. Mixing may influence this gelation rate by encouraging collision of the polymer chains.

In general, a physically cross-linked poly(vinyl alcohol) gel is prepared from an aqueous poly(vinyl alcohol) solution (from 1% to 50% PVA by weight of the solution) that is gelled by contacting with a solvent having a $\chi$ value sufficient for gelation, hereinafter called the second solvent at a concentration approximating the "theta" concentration for the poly (vinyl alcohol) solution.

The present invention provides methods of producing poly (vinyl alcohol) hydrogels that do not use chemical crosslinkers, irradiation or thermal cycling. In preferred embodiments, the solvent quality is controlled, preferably by controlling the diffusion of the second solvent (NaCl or methanol) into a PVA solution to produce a homogenous, physically crosslinked structure.

The present method uses a controlled change in solvents differing in solvent quality, conveniently expressed by the Flory interaction parameter to force the PVA to associate. Because no chemical cross-linkers are used, the gel is substantially free of chemical crosslinkers and thus likely to be as biocompatible as thermally-cycled PVA cryogels. Any residue of NaCl in the gel following equilibration in deionized water is likely to be benign, as its concentration will certainly be below physiologically relevant values.

Figure 2:
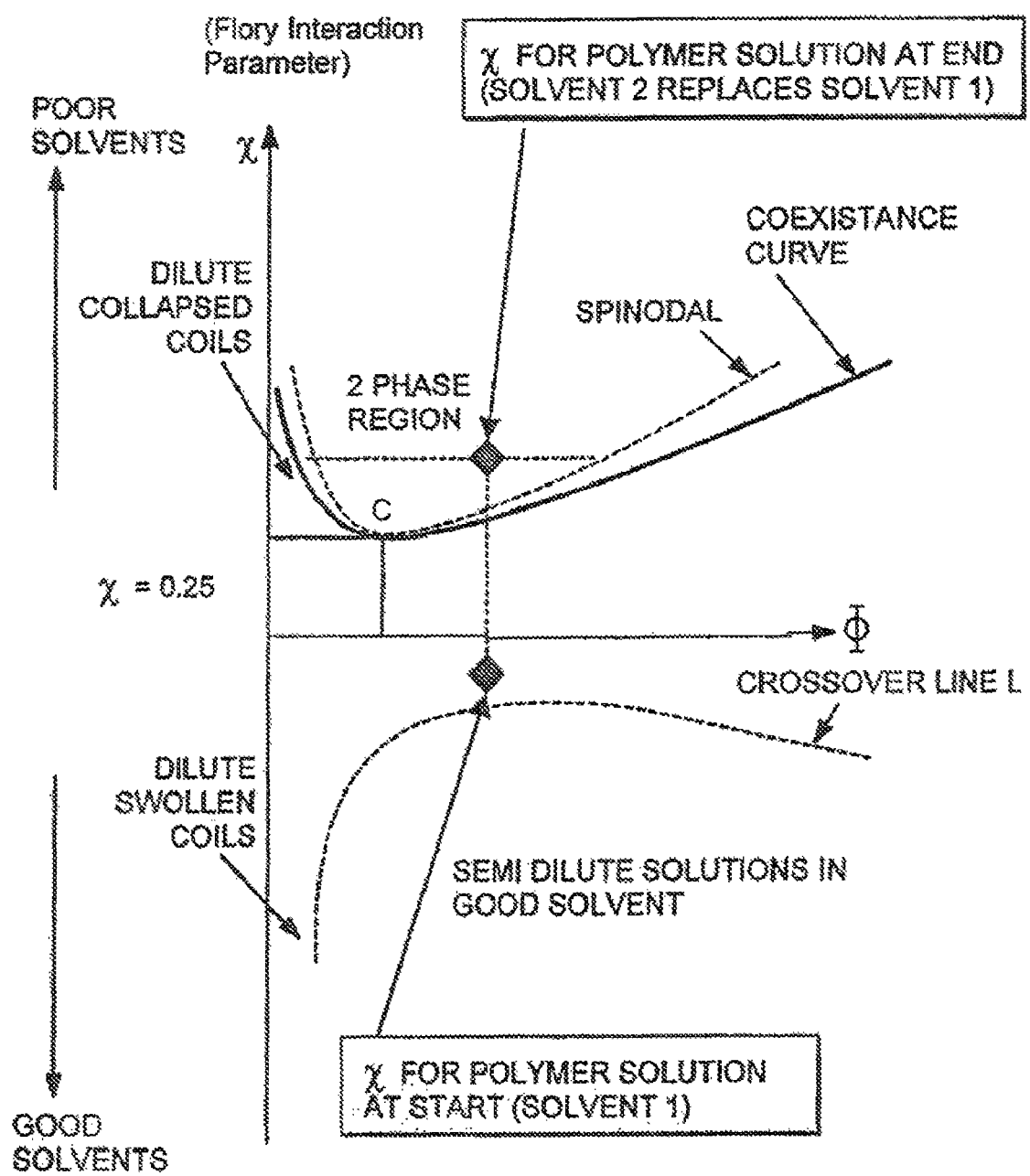
FIG. 2 is a graphical representation of the relationship of the Flory interaction parameter, $\chi$, to the concentration ($\Phi$) of a polymer at a given temperature in accordance with preferred embodiments of the present invention. The abscissa, at $\chi=0.25$, separates polymer solutions in first solvents (below) and polymer solutions in second solvents (above). The arrows and diamonds indicate the effect on $\chi$ produced by replacing solvent 1 with solvent 2.

FIG. 2 illustrates the relationship between the first solvent and the second solvent in terms of the Flory interaction parameter, $\chi$. FIG. 2 is a graphical representation of the relationship of the Flory interaction parameter $\chi$, to the concentration ($\Phi$) of a polymer at a given temperature. The abscissa, at $\chi=0.25$, separates polymer solutions in first solvents (below) and polymer solutions in second solvents (above) sufficient to cause gelation. The arrows and diamonds indicate the effect on $\chi$ produced by replacing solvent 1 with solvent 2.

By implication any solvent can be "good" or "bad" as defined using the Flory interaction parameter, $\chi$. In terms of $\chi$, these solvency properties are roughly $\chi<0.5$ for good solvents and $\chi>0.5$ for bad solvents, with the condition of $\chi=0.5$ defining a "theta" solvent. The good-bad solvent transition is not a step change, but is instead a gradual variation in the solubility of the polymer in the chosen solvent. Consequently, changing the solvent quality changes the affinity of the polymer with itself, either through intra-chain interactions if the solution is sufficiently dilute, or through inter-chain interactions. The effects of changing solvent quality on polymer solubility can be seen in experimental data, or theoretically as shown in equation 1:

$$v=(1-2\chi)a^d \qquad (1)$$

where $\Box$ is excluded volume of a single chain, $\chi$ is the Flory interaction parameter and $a^d$ is the monomer volume. The theta point, where the chain is unperturbed, is therefore where $v=0$ or $\chi=0.5$. For $v<0$, phase separation occurs and there is an equilibrium between nearly pure solvent and a polymer-rich phase. However, due to the large size of the polymer molecules discussed herein, there is always some polymer in the solvent phase, and similarly there is always an appreciable amount of solvent in the polymer rich phase. The solvent can be a single chemical species, or a mixture of species that is not necessarily limited to low molecular weight compounds.

It is usually considered that PVA phase separates through a spinodal decomposition process. Note that there is no rate dependent effect in this equation, although the spinodal decomposition process does have a characteristic rate, and it is a balance of rate effects that is exploited in the embodiments of the present invention. For PVA in water, the Flory interaction parameter is weakly dependent on concentration but $\Box>0.5$ for polymer volume fractions greater than about 5%. The PVA gel has a higher interaction parameter than the solvent but there is no dependence of $\chi$ on molecular weight or crosslink density of the gel.

In preferred embodiments, $\chi$ of the second solvent must be more positive than the $\chi$ of the first solvent (dissolved PVA solvent) and is preferably be in the range of 0.25 to 2.0. Preferably $\chi$ of the first solvent is in the range of 0.0 to 0.5. In general, the temperature during processing may vary from just above the freezing point of the PVA solution to the melting point of the physical crosslinks formed in the process. The preferable range is from about 0 degrees Celsius to about 40 degrees Celsius. Note that $\chi$ is coupled to temperature and concentration. In preferred embodiments the temporal and spatial change in $\chi$ of the PVA solution (the first solvent) is controlled by contact with another miscible solution (comprising the second solvent), wherein the second solvent modifies the first.

The removal of the need for chemical crosslinkers and radiation processing allows a greater variety of embedded components. For instance many bioactive materials are highly intolerant of chemical crosslinkers and radiation. In addition although in general the freeze-thaw process is gentle on bioactive components there can certainly be envisaged polymers, biopolymers or cells that either cannot be frozen, or act as antifreeze hence preventing the freezing.

The method used to create these thetagels is likely to produce a wider range of material properties and greater control over the physical structure of the final gel than is possible with competing cryogels. The advantage of thetagels over thermally cycled PVA gels for certain applications is outlined below.

Cryogels have a fairly low resolution with regard to their final properties because each thermal cycle produces a dramatic change in the material properties of the gel. The thetagels produced demonstrate that the concentration of the solvent produces a monotonic decrease in swelling ratio once the theta value is passed (See FIG. 7). It is desirable that the ultimate crosslink density is adjustable in proportion to the resolution achievable in the solvent concentration. For example, for the 10% PVA solution immersed in NaCl the weight percentage of PVA in the final gel varies at a rate of about 7%/mole NaCl.

The preferred embodiments of the present invention provide gels having a starting weight (based on the weight of the solution) from about 1 weight % to about 50 weight % PVA. In preferred embodiments, the weight percent ranges from about 12% to about 29% PVA in the final gel where the immersion solution used was about 2.0 about 3.0 M NaCl (aq). This range of final PVA weight percentages is comparable to that which can be achieved by thermally cycled PVA. With higher NaCl solutions (in excess of 6.0 M) percent PVA of the final gel increases monotonically with NaCl concentration. It has been found that PVA thetagels can be made that exhibit a smooth gradient in spatial properties. In contrast, gradients of properties cannot easily be manufactured in cryogels. Instead, the usual approach is to generate an array of stacked lamellae independently that must be joined in dissolved PVA and then cycled again. Sharp differences in modulus in such an array would create a material with undesirable mechanical properties and with inhomogeneous interfaces. In preferred embodiments, PVA thetagels having a smooth gradient in mechanical properties, can be used to make a prosthetic intervertebral disk a central lower modulus "pulposus" having adequate compressive strength and a higher modulus peripheral "annulus" that minimizes creep and undesirable distortion.

Modulus enhancement can be accomplished by incorporation of ionic species. For thetagels produced in NaCl, it is possible to include natural (hyaluronic acid) or synthetic (PAA) polymers to create gels with strain variable compressive moduli. Gelling a PVA/PAA solution in strong NaCl shield the ionizable charges in the PAA while the PVA is crosslinked around the collapsed PAA. Re-equilibration in deionized water will allow expansion of the PAA and pre-stress the PVA matrix. The resulting construct should have a very different mechanical compressive modulus due to the repulsion of the fixed charges on the incorporated PAA.

It is known in the art that PVA elicits little or no host biological response when implanted in animals. For this reason, PVAs are used in a variety of biomedical applications including drug delivery, cell encapsulation, artificial tears, artificial vitreous humor, contact lenses, and more recently as nerve cuffs. However, PVA has generally not been considered for use as a load bearing biomaterial primarily because of its low modulus and poor wear characteristics. The loads that any vertebral implant must withstand will be reasonably high (on the order of 4 MPa in compression) requiring a high compressive modulus. In vivo, the compressive axial load on the intervertebral disk is transferred by the nucleus pulposus to a tensile circumferential load in the annulus fibrosis. Any biomaterial intended to replace the function of an intervertebral disk in its entirety must incorporate similar anisotropic properties.

To improve overall strength, PVA modulus and wear characteristics can be enhanced by the formation of either chemical or physical cross-links. Cross-linking PVA by the addition of chemical agents (such as polyaldehydes), through irradiation, or by freeze-thaw cycling, has been shown to improve the durability of PVA gels. However, chemical additives can leave unwanted residual reactive species behind that make the final product unsuitable for transplant, while irradiation may adversely affect any bioactive material encapsulated in the matrix. Thus, the generation of extensive physical cross-links through freeze-thaw cycling has substantially improved the durability of PVA without the negative side effects produced by chemical or irradiation induced crosslinking. Recent investigations suggest that the physical crosslinks produced by freeze-thaw cycling might generate biomaterials with moduli suitable for use as biocompatible replacements for load bearing structures such as articular cartilage or intervertebral disk.

Solvation of Polymers and the "Theta" Point

Polymers in solution are complex molecules in perpetual dynamic motion. The configuration of an ideal polymer chain is usually described as a "random walk", where the molecule is assumed for simplicity to be freely jointed and free to move where it will. This behavior results in the polymer assuming a spherical shape with a Gaussian distribution. In reality the chain has a number of forces acting on it to define its shape and behavior. In free solution the chain is subject to random motion from Brownian fluctuations arising out of the temperature of the system. At the same time there is a force arising out of how the chain interacts with itself (since it is a long, extended molecule) and its surroundings.

If the polymer is easily solvated by the solution (i.e., it is in a first solvent not having a $\chi$ value sufficient for gelation) it swells as it tries to maximize the amount of polymer chain that is exposed to the solvent. In the first solvent, the energy of interaction between a polymer element and a solvent molecule adjacent to it exceeds the mean of the energies of interaction between the polymer-polymer and solvent-solvent pairs as described by Flory, P. J. in, Principles of Polymer Chemistry, page 424, Cornell University Press, 1953, the teaching of which are herein incorporated by reference in their entirety. The chain is now in a perturbed state and resists contact with neighboring chains and equally resists mechanical compression and deformation. As the solvency changes, this swollen configuration collapses as the quality of the solvent falls.

At the theta point, the solvent quality is such that the random Brownian motions are enough to keep the chain in an ideal, Gaussian distribution. Below this critical threshold the chain segments prefer to be next to each rather than to a solvent molecule, and the chain shrinks (i.e. a second solvent having a $\chi$ value sufficient for gelation). The Flory interaction parameter, $\chi$ is dimensionless, and depends on temperature, pressure etc. The first solvents have a low $\chi$, while the second solvents have a high $\chi$, with a transition at about $\chi$=0.5. The case $\chi$=0 corresponds to a solvent which is very similar to a monomer. In a lattice model this is the case where the free energy comes entirely from the entropy associated with various chain patterns on the lattice. In such a case, temperature has no effect on structure, and the solvent is said to be "athermal." Athermal solvents are a particularly simple example of good solvents. In most cases the parameter $\chi$ is positive as described by de Gennes, P. G. in, Scaling Concepts in Polymer Physics, First ed. p. 72: Cornell University Press (1979). If the solvent quality is poor enough, the chain will completely precipitate out of solution. This effect can also be obtained by manipulation of the temperature of the solution.

Once the concentration of the polymer solution is high enough, adjustment of the solvent quality can be achieved by replacing at least part of a first solvent with a second solvent that forces inter-chain interaction as well as intra-chain interaction. Once the physical crosslinking has occurred, the later presence of a good solvent, which naturally swells the free polymer, is balanced by the physical crosslinking. With inter-chain associations the polymer chains are now constrained at certain pinning-points. Consequently as the polymer is solvated, and stretches, it becomes more deformed and is forced into tension. It is the competition between the solvation of the polymer chains and this tension in the deformed chains that give gels their interesting mechanical behaviors. In addition, under certain conditions the polymer chains can be ionized, consequently generating a charge. Adjacent like charges will result in further swelling due to electrostatic repulsion. This is part of the mechanism that gives natural cartilage (collagen and glycosaminoglycans) its high modulus, and high hygroscopic properties.

Gelation Mechanism in PVA

Freeze-thaw cycling of solutions of PVA polymer results in the formation of physical cross-links (i.e. weak bonding through an "association" of the polymer chains). PVA hydrogels formed in this manner are termed "cryogels" and are described, for example, in U.S. Pat. Nos. 6,231,605 and 6,268,405, the teachings of which are incorporated herein by reference in their entirety. Importantly, the techniques utilized to create PVA cryogels do not require the introduction of chemical crosslinking agents or radiation. Cryogels are therefore easily produced with low impact on incorporated bioactive molecules. However, incorporated molecules are limited to those that can tolerate the freeze-thaw cycles required to make the gel. Thus the resulting material can contain bioactive components that will function separately following implantation. PVA cryogels are also highly biocompatible (as will be the proposed PVA "thetagels" to be presented later). They exhibit very low toxicity (at least partially due to their low surface energy), contain few impurities and their water content can be made commensurate to tissue at 80 to 90 wt %.

There is still some debate over the exact mechanism that drives the gelation of PVA through a freeze-thaw cycle. However, three models have been proposed to explain the physical crosslinking that occurs during the freeze-thaw cycle: 1) direct hydrogen bonding; 2) direct crystallite formation; and 3) liquid-liquid phase separation followed by a gelation mechanism. The first two steps suggest that the gel forms through a nucleation and growth (NG) phase separation, whereas the third option pictures the process as a spinodal decomposition (SD) phase separation. Hydrogen bonding will form nodes and crystallite formation will form larger polymer crystals. However both of these mechanisms will form closely connected crosslinks, with relatively small crosslinking nodes. This observation is supported by studies on the gelation mechanism of PVA. Spinodal decomposition on the other hand causes redistribution of the polymer into polymer rich and polymer poor regions followed by a gelation process which results in more distantly spaced crosslinks. It is thought that phase separation through spinodal decomposition is likely to be responsible for the improved mechanical properties of PVA after crosslinking and occurs due to a quenching of the polymer solution. During the freezing process, the system undergoes a spinodal decomposition whereby polymer rich and poor phases appear spontaneously in the homogeneous solution. This process occurs because the phase diagram of quenched PVA (and polymers in general) at certain temperatures can have two coexisting concentration phases. The polymer rich phases are therefore highly concentrated which enhances the natural (weak) gelation of the PVA.

For cryogels, the physical characteristics depend on the molecular weight of the uncrosslinked polymer, the concentration of the aqueous solution, temperature and time of freezing and the number of freeze-thaw cycles. Thus the properties of a cryogel can be modulated. However, since the material's properties change dramatically at every freeze-thaw step, control over the properties of the finished gel is somewhat limited. The thetagels described broaden the range of functionality currently provided by PVA cryogels.

In general, the modulus of the PVA cryogel increases with the number of freeze-thaw cycles. In one experimental series, thermally cycled PVA cryogels had compressive moduli in the range of 1-18 MPa and shear moduli in the range of 0.1-0.4 MPa. Stammen, J. A., Mechanical properties of a novel PVA hydrogel in shear and unconfined compression Biomaterials, 2001 22: p. 799-806.

As cryogels are crosslinked by physical and not chemical means, there is some concern about their structural stability. The modulus of PVA, in aqueous solution increases with soak time in distilled water at constant temperature. In one experiment, conducted over 40 days, the modulus increased by 50%. Putatively, during aqueous aging, the increase in strength, with the concomitant loss of soluble PVA, is the result of an increase in the order of the supramolecular packing of the polymer chains. There are significant implications in this data for the long-term storage effects of the freeze-thaw gelled PVA.

It is also important to understand the effects of loss of polymer over time and how that impacts the local host biological environment. It should be noted that in this example, the cryogel was only freeze-thaw cycled once, although others have shown PVA dissolution following multiple freeze-thaw cycles. In general, there is very little information about the stability of PVA cryogel modulus under repeated load cycling (fatigue).

As might be expected, the swelling of PVA cryogels at any time point decreases with increasing number of freeze-thaw cycles, indicating a densification of the PVA gel, most likely due to a higher crosslink density. In the long term, following gelation and under static conditions, the ultimate swelling ratio decreases while the modulus increases with time.

In freeze-thaw processing, temperature is used to force a phase separation of the PVA solutions, thus enhancing the gelation mechanism in the PVA (it should be noted that even at room temperature a solution of PVA begins to gel weakly over time).

Solvent quality is related to both temperature and the chemical interaction of the solvent to the polymer, and is conveniently described by the Flory interaction parameter $\chi$. In a preferred embodiment, the manipulation of the solvents quality through some process other than temperature allows much greater control over the gelation process while permitting the method to be practiced at approximately room temperature. In particular, by using aqueous based solvents for PVA, the system can be chosen to minimize impact on materials embedded in the PVA, and can allow fine spatial and temporal control over the final structure of the gel. In a particular solvent, the critical parameter defining the transition from the first to second solvent (and hence driving the phase separation) is known as the theta temperature. An example list is presented in Table 1 below.

TABLE 1

Theta temperatures for PVA in various solvents
(Brandrup, J. & Immergut E. H., Polymer Handbook, 3Ed.
1989, NY, John Wiley & Sons).

| Solvent | Volume Ratio | Theta Temperature [° C.] |
| --- | --- | --- |
| t-Butanol/Water | 32:68 | 25 |
| Ethanol/Water | 41.5:58.5 | 25 |
| Methanol/Water | 41.7:58.5 | 25 |
| i-Propanol/Water | 39.4:69.6 | 25 |
| n-Propanol/Water | 35.1:64.9 | 25 |
| NaCl/Water | 2 Moles/L | 25 |
| Water | — | 97 |

Physically cross-linked PVA gels may also be produced through thermal cycling (not necessarily with freezing) combined with dehydration. Such gels are potentially suitable for use in load bearing applications (i.e. artificial articular cartilage). Examination of the material properties of this thermally cycled PVA found that the material distributes stress more homogeneously than stiff single-phase biomaterials (ultra-high molecular weight polyethylene (UHMWPE)) and preserves the lubrication film gap readily in simulated articular cartilage loading. The material sustained and distributed pressure in the thin film of between 1 and 1.5 MPa. In transient load tests, the PVA withstood and distributed loads of nearly 5 MPa.

Studies have been conducted that further examined the wear properties of their thermally cycled, dehydrated PVA under a variety of conditions. The wear rate found in unidirectional pin-on-disk (against alumina) experiments was comparable to that of UHMWPE (although this test is probably not the most suitable to perform for biological implants). However, in reciprocating tests, the wear rate was up to 18 times larger. To improve the wear properties, PVA of higher molecular weight and additionally cross-linked by gamma-radiation (doses over 50 kGy) was tested. Such treatment reduced the wear rate considerably (to about 7 times that of UHMWPE). However, in both radiation and thermally crosslinked PVA the wear rate does not appear adequate for applications where the opposing surface has high hardness. Additionally, irradiation would adversely affect bioactive materials loaded into the gel.

Methods in accordance with a preferred embodiment include the following:

PVA solutions. To make the 10% solution, 20 grams of PVA (100 kg/mole; 99.3+% hydrolyzed; JT Baker) was dissolved in 180 grams of deionized water at 90° C. for one to two hours. To make the 20% solution, 30 grams of PVA was dissolved in 180 grams of deionized water, the solution was stirred continuously until 60 grams of water evaporated to generate a final solution of 20% PVA.

PVA gelation. 4-5 ml of PVA solution of 10 or 20 weight percent were injected into pre-wetted Slide-A-Lyzer Dialysis cassettes (Pierce, Rockford, Ill.) with a molecular weight cutoff of 3500 Daltons. The 10% PVA solutions were then immersed in NaCl aqueous solutions of 1.5 M, 2.0 M 2.5 M or 3 M. The 20% PVA solution was immersed in 3.0 M NaCl. To demonstrate that the gelation effect was not NaCl/aqueous solvent-dependent, a 10% PVA solution in a dialyzer cassette was immersed in a 50/50 methanol/water solution. After 3 days, all of the cassettes containing 10% PVA solution were removed from their respective solvents. The gels were then removed from the cassettes and placed in DI water for at least 5 days to allow initial PVA crystal dissolution the cassette containing the 20% PVA solution was removed after 3 days. The PVA gel was removed from the cassette and a portion was stored in DI water. The remaining PVA gel was returned to the 3M NaCl solution. At 6 and 12 days, portions of the 20% PVA gel were removed and placed into DI water for at least five days before further testing.

Quantitative Characterization

To quantify the effect on the structure of the gels of immersion solution molarity and time immersed, differential scanning calorimetry (DSC), gravimetric swell ratio analysis and dynamic mechanical analysis (DMA) were performed on the samples.

Differential Scanning Calorimetry. DSC thermograms were obtained using an instrument, for example, a TA Instruments Q1000 (TA Instruments, New Castle, Del.). Selected wet PVA gel samples between 5 and 15 mg were removed from deionized water storage after 5 days, blotted dry and crimped into anodized-aluminum hermetic pans. Scans were performed at 5° C./min from 5° C. to 120° C. The total enthalpy change for the melting of the gel physical crosslinks was estimated using a linear integration from the departure from baseline (typically near 40° C.) to return to baseline (typically near 90° C.). Following DSC analysis, the hermetic pans were punctured, weighed and placed in a vacuum oven for dehydration. After two days of dehydration the pans were reweighed to determine the percent PVA in the original sample.

Gravimetric swell ratio. Samples of PVA gel from each sample were removed from deionized water storage after 5 days, blotted with a tissue and dehydrated in a vacuum oven for 2 days. The gravimetric swell ratio was calculated as the ratio of the mass of water in the gel to the mass of PVA in the gel.

Dynamic Mechanical Analysis. To examine the effect of curing solvent quality, dynamic mechanical analysis was performed using a Perkin-Elmer TMA 7 (Perkin Elmer, NJ) on the 10% PVA 3 M NaCl and 2 M NaCl samples. To examine the effect of aging in the curing solvent, DMA was also performed on the 20% 3 M NaCl 3 day and 12 day samples. Samples were cut into rectangles and tested in unconfined compression with a static load of 250 mN (10% samples) or 1000 mN (20% samples). The storage (and loss moduli for the 10% samples) were determined for a frequency sweep from 1 to 2 Hz at room temperature.

In a preferred embodiment, forcing poly(vinyl alcohol) polymer chains in solution into close proximity (through a spinodal decomposition mechanism) results in the formation of a physical association that is resistant to dissolution. This methodology generates a PVA hydrogel employs the controlled use of the second solvents having a $\chi$ value sufficient to cause gelation to force the PVA chains to physically associate. It is critical that the solvent quality is controlled carefully, and in particular for larger components, that the solvent "front" enters the PVA solution in a controlled manner. NaCl/deionized water and methanol/deionized water solutions at concentrations in the neighborhood of their "theta" value for PVA were used to force the physical association and subsequent gelling of the PVA. Gels formed in this way are termed "thetagels".

Figure 3A:
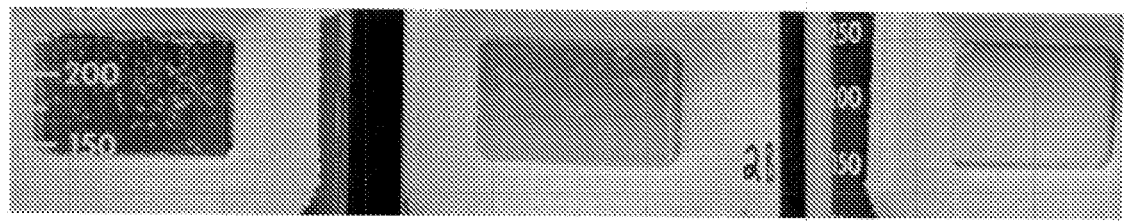
FIGS. 3A and 3B show 10% PVA solution in dialyzer cassettes after 1 day (top, 3A) and 3 days (bottom, 3B) of immersion in curing solution in accordance with a preferred embodiment of the present invention. From left to right: 1.5 M NaCl, 2.0 M NaCl and 3.0 M NaCl. The 1.5 M solution does not gel the PVA, the 2.0 M solution and 3.0 M solution do gel the PVA. Note the progressive opacification of the 2.0 M gel and the shrinkage of the 3 M gel from the edges of the cassette as the sample compacts with time (indicated with arrow).
Figure 3B:
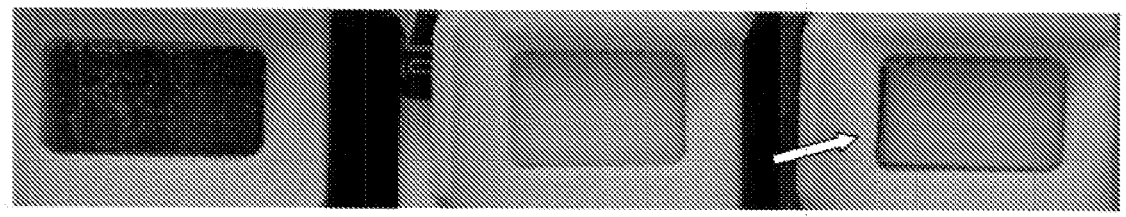

The physical appearance of the hydrogel depends on the molarity of the solution into which the PVA solution is immersed. FIGS. 3A and 3B demonstrate the progression of the gelation of the PVA hydrogel during exposure to NaCl solutions near the "theta" concentration. As exposure time increases, the PVA solution becomes stiff and opaque for the solutions at or above the theta concentration and temperature. For solutions appreciably below the theta concentration, little or no gelling is apparent. Immersion of the PVA solution into the 50/50 water/methanol solution also resulted in the generation of a uniform PVA hydrogel.

FIGS. 3A and 3B show 10% PVA solution in dialyzer cassettes after 1 day (top, 3A) and 3 days (bottom, 3B) of immersion in curing solution. From left to right: 1.5 M NaCl, 2.0 M NaCl and 3.0 M NaCl. The 1.5 M solution does not gel the PVA, but the 2.0 M solution and 3.0 M solution do gel the PVA. Note the progressive opacification of the 2.0 M gel and the shrinkage of the 3 M gel from the edges of the cassette as the sample compacts with time (indicated with arrow).

Figure 4:
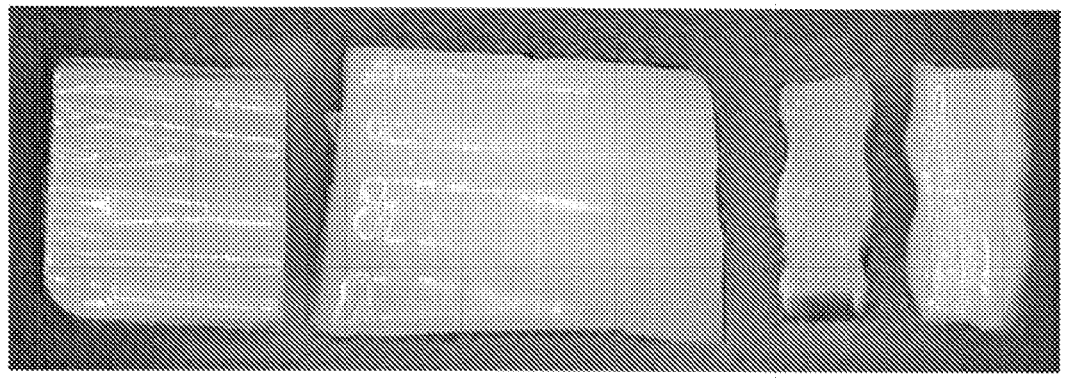
FIG. 4 shows a uniform thetagel in accordance with a preferred embodiment of the present invention. PVA gels generated by immersion in 3.0 M (left image of each pair) and 2.0 M (right image) NaCl curing solution. Note that the gels are uniform and opaque. The gel exposed to 3.0 M NaCl swells less and is more compact following equilibration in deionized water.

FIG. 4 demonstrates the difference between 10% PVA exposed to 3.0 M and 2.0 M solutions for 3 days (after photographed subsequent equilibration in deionized water). PVA gels were generated by immersion in 3.0 M (left image of each pair) and 2.0 M (right image) NaCl immersion solution. Note that the gels are uniform and opaque. The gel exposed to 3.0 M NaCl swells less and is more compact following equilibration in deionized water. The hydrogels that result are uniform and opaque. The PVA exposed to 2.0 M NaCl is more highly hydrated than that exposed to the 3.0 M NaCl. The increased swelling is an indication that the density of physical crosslinks is lower in the gel exposed to the 2 M NaCl solution. Thus, gels formed in this way are "tunable" with respect to mechanical properties. Further, gradient gels can be made using the method through manipulation of the spatial NaCl concentration.

Figure 5:
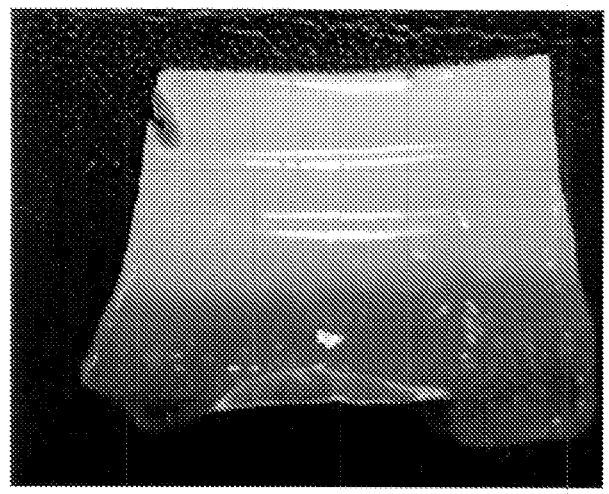
FIG. 5 shows an example of a gradient gel in accordance with a preferred embodiment of the present invention using a 10% PVA solution exposed to spatially varying NaCl concentration. Note the variation in both the translucency of the gel and in the swelling ratio.

FIG. 5 shows a hydrogel formed from a 10% PVA solution that was exposed to a spatially varying NaCl concentration. Note, the variation in both the translucency of the gel and in the swelling ratio. The opaque part of the gel was exposed to 3.0 M NaCl while the clear part was exposed to a concentration below the theta concentration (2.0 M at room temperature). The ability to generate a gradient is relevant to the generation of a total disk replacement nucleoplasty, with a rigid outer layer (annulus fibrosis) and a softer center (nucleus pulposus).

Differential Scanning Calorimetry

Figure 6:
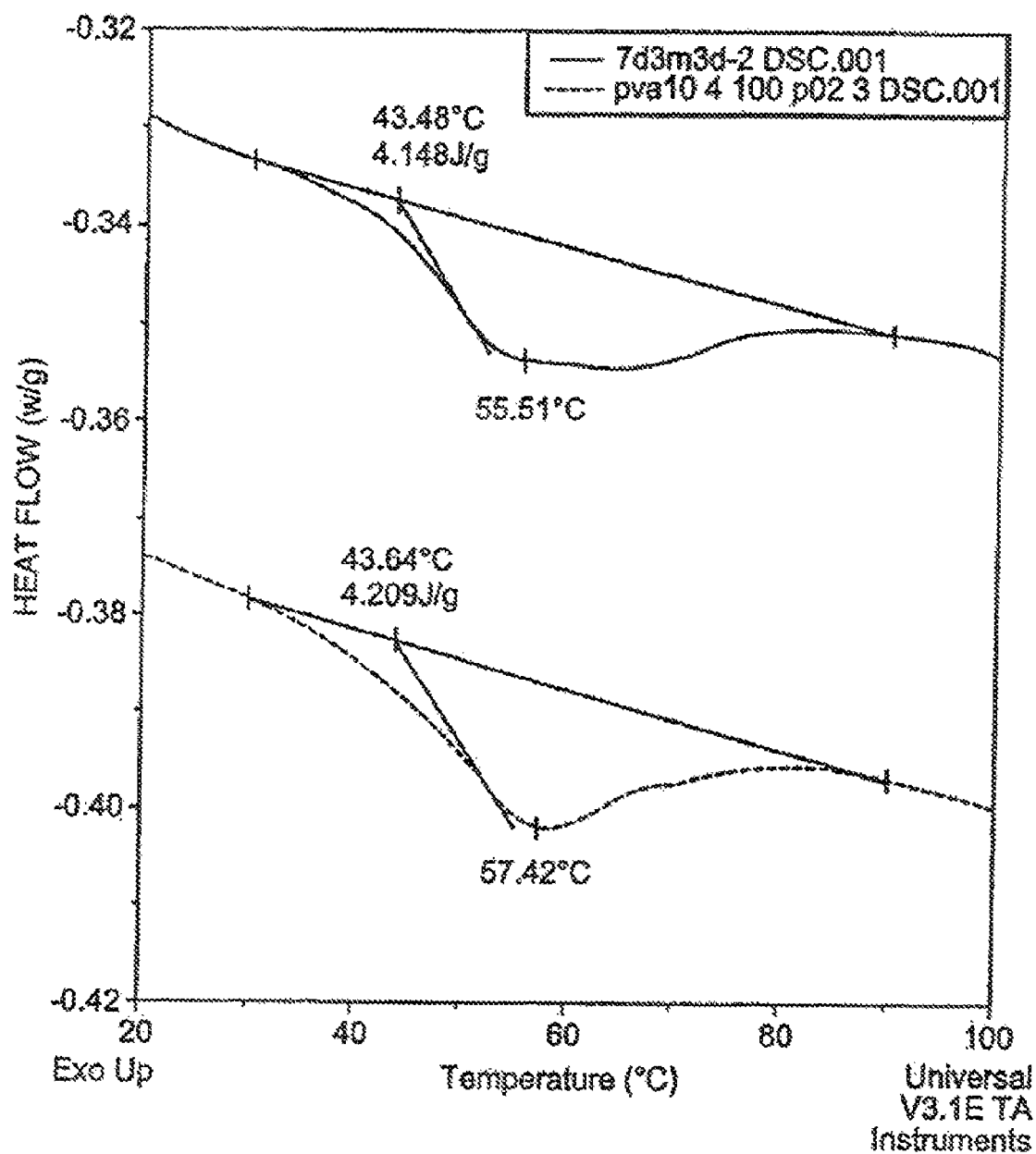
FIG. 6 shows a differential scanning calorimetry (DSC) thermogram comparing the results obtained with a thermally cycled PVA cryogel and the "thetagel" in accordance with a preferred embodiment of the present invention. The solid line is indicative of 10% PVA immersed in 3.0 M NaCl for 3 days; the dashed line is indicative of 10% PVA thermally cycled 4 times from 10 degrees Celsius to −20 degrees Celsius with a warming rate of 0.02 degrees Celsius/min.

For thermally cycled PVA gels, an endotherm between 30 degrees Celsius and 90 degrees Celsius represents the energy required to disrupt the physical crosslinks formed during the thermal processing. For PVA thetagels in accordance with a preferred embodiment, a similar endotherm was present, FIG. 6 compares the DSC thermogram of a thermally cycled PVA cryogel and a PVA hydrogel formed in 3.0M NaCl. The transitions have similar melting endotherms and occur at virtually the same temperature.

The enthalpy change of this endothermic transition gives a good indication of the amount of crosslinking in the gel as a result of the solution conditions. For a 10% PVA solution for example the enthalpy change obtained after immersion for 3 days in a 2.0M solution of NaCl was 16.9 J/g. In contrast the same initial PVA solution yielded an enthalpy change of 19.9 J/g after 3 days in a 3M solution. This result indicates that solution concentration and soak time both positively impact the amount of physical crosslinking in the gel.

Gravimetric Swell Ratio

Figure 7:
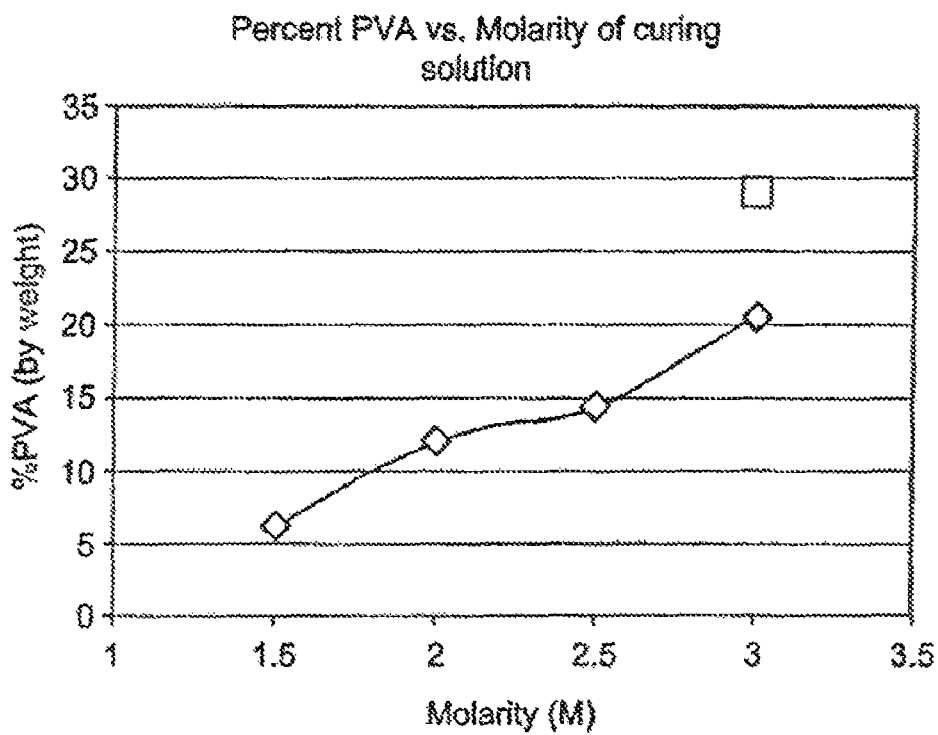
FIG. 7 graphically illustrates the relationship between the percentage of PVA in PVA hydrogels that were fully equilibrated in deionized water after being gelled in immersion solutions of different molarities in accordance with a preferred embodiment of the present invention. The connected points represent measurements of 10% PVA immersed for 3 days, the single point represents an initial solution of 20% PVA solution immersed in 3 M NaCl for 12 days. For the 20% PVA solution, the 3 day value of swelling ratio and percentage of PVA matched that of the 10% PVA solution (not shown). After 12 days of immersion in 3 M NaCl (and 5 days of equilibration in deionized water), the 20% PVA solution formed a gel that was 29% PVA.
Figure 8:
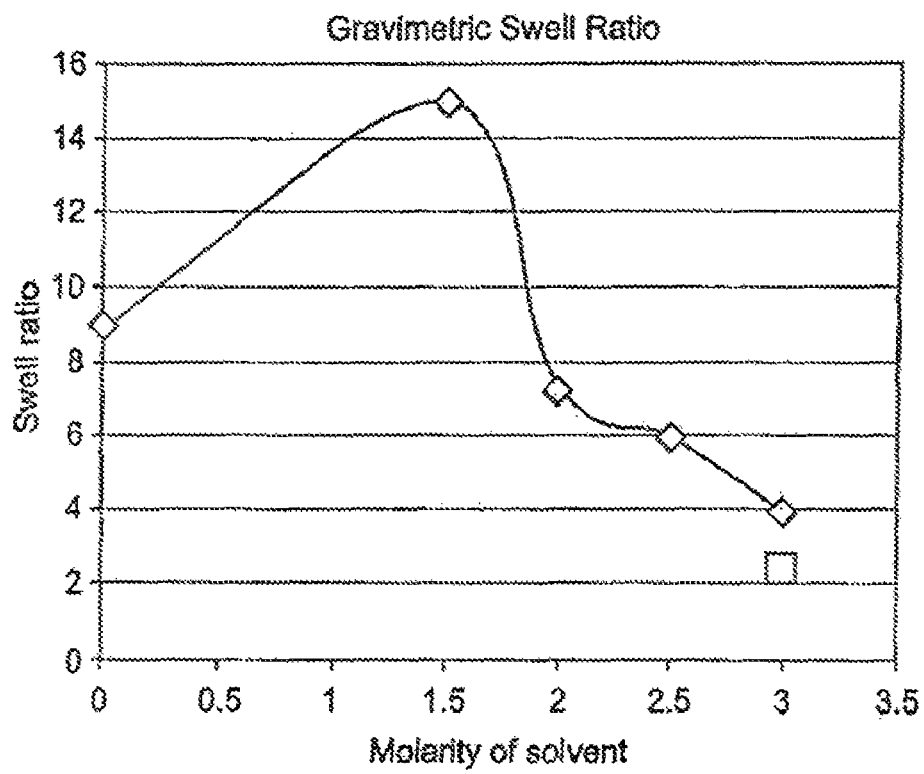
FIG. 8 graphically illustrates the gravimetric swelling ratio for PVA hydrogels that were fully equilibrated in deionized water after being gelled in immersion solutions of different molarities in accordance with a preferred embodiment of the present invention. The connected points represent measurements of 10% PVA immersed for 3 days, the single point represents an initial solution of 20% PVA solution immersed in 3 M NaCl for 12 days. For the 20% PVA solution, the 3 day value of swelling ratio and percentage of PVA matched that of the 10% PVA solution (not shown).

In a preferred embodiment, increasing the molarity of NaCl in the solvent increases the amount of PVA present in the hydrogel per unit mass. FIG. 7 shows the relationship between the percentage of PVA in the gels (fully equilibrated in deionized water) and the molarity of the solution in which they were cured. Because the PVA is not rigidly held in the dialysis cassette, it is free to expand or contract under the influence of the local forces on the PVA during the gelation process. It is therefore possible for the final PVA concentration to exceed that of the initial PVA solution if the PVA gel has collapsed. FIG. 8 shows the gravimetric swelling ratio for PVA cured in solutions of varying NaCl molarity. For the 20% PVA solution, the 3 day value of swelling ratio and percentage of PVA matched that of the 10% PVA solution (not shown). After 12 days of immersion in 3 M NaCl (and 5 days of equilibration in deionized water), the 20% PVA solution formed a get that was 29% PVA.

Dynamic Mechanical Analysis

Figure 9:
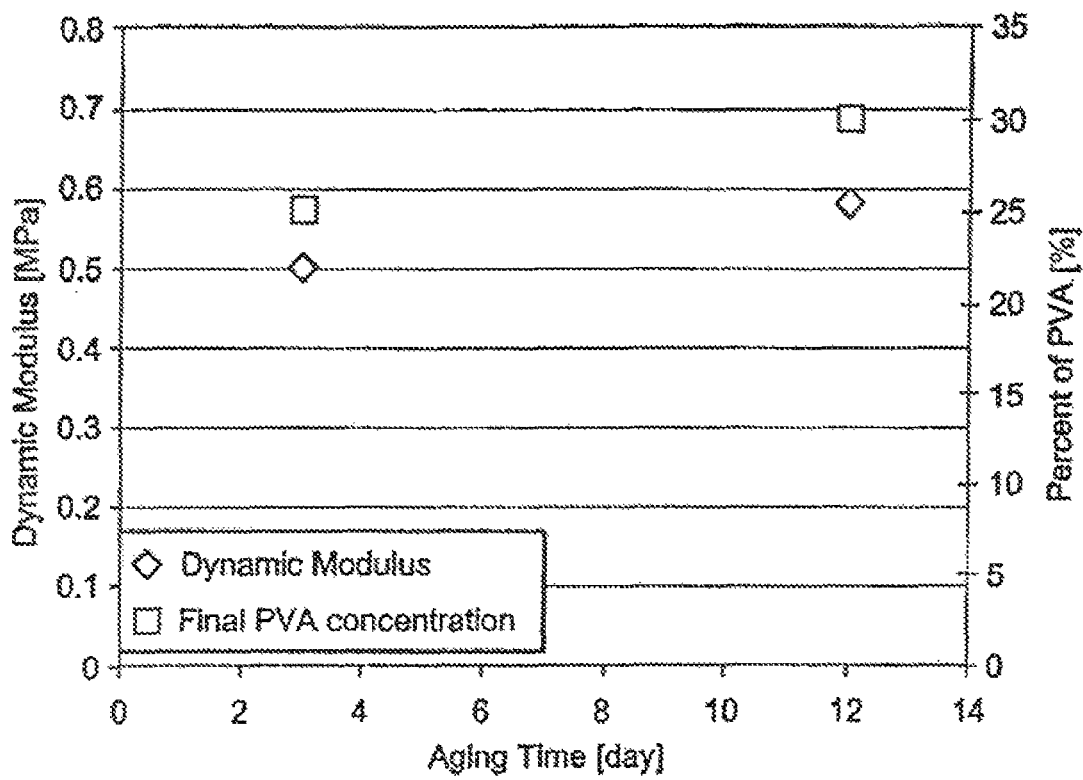
FIG. 9 shows the dynamic modulus of PVA thetagel at 3 M NaCl, 20% initial PVA concentration and 1 N static load versus aging time in days in accordance with a preferred embodiment of the present invention.
Figure 10:
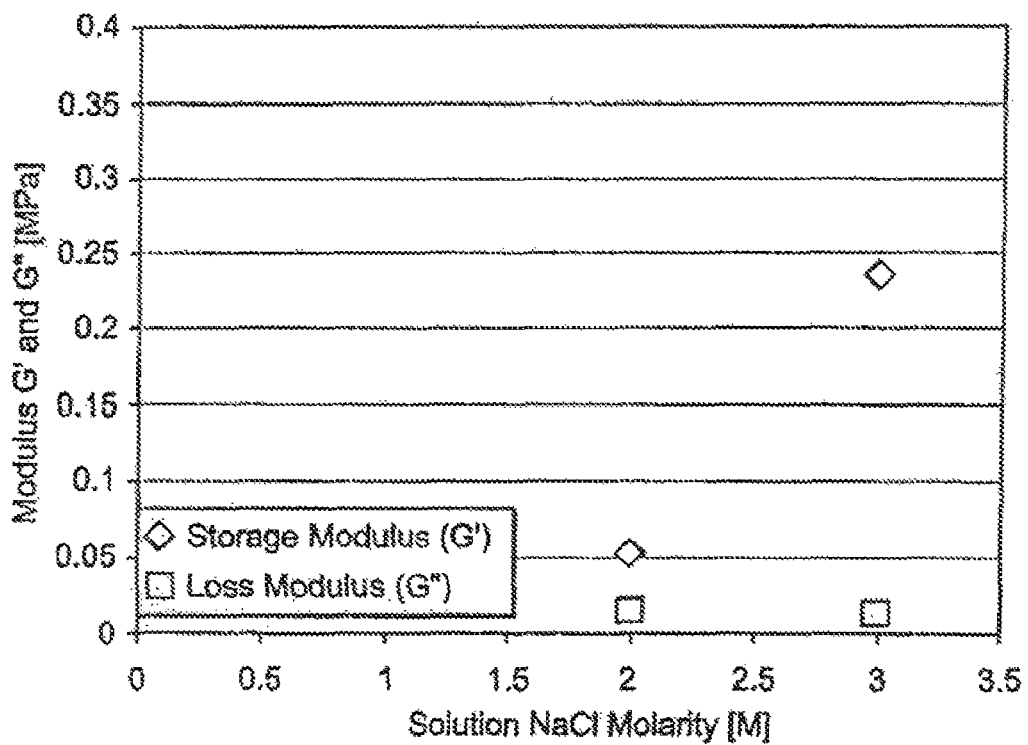
FIG. 10 shows the complex modulus (Storage (G') and Loss (G") Modulus) of PVA thetagel at 20% initial PVA concentration and 0.25 N static load against solution molarity (2M and 3M NaCl) in accordance with a preferred embodiment of the present invention.
Figure 11:
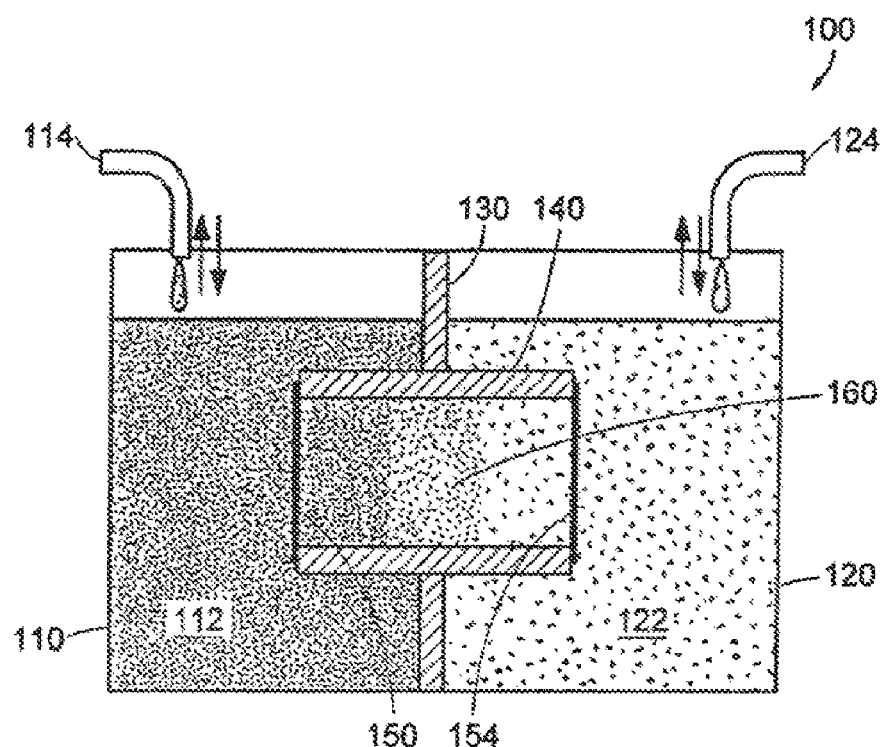
FIG. 11 is a schematic diagram of an "Ussing" type chamber used to create a gradient gel 160 in accordance with a preferred embodiment of the present invention.

In a preferred embodiment, the solution conditions and time of aging have a marked effect on the visible structure of the gels, and on their thermal properties. Both effects suggest that there is likely to be an influence on the mechanical properties as well. This supposition is born out by qualitative examination of the samples, but for more rigorous analysis mechanical testing was performed on the samples using DMA. FIGS. 9 and 10 present data taken from three of the samples. FIG. 9 shows that the complex modulus of the sample increases with aging (keeping all other solution conditions constant). In fact, this increase in the modulus is also paralleled by a densification of the final PVA gel. FIG. 10 examines the change in modulus corresponding to the change in solution molarity (once again keeping all other parameters constant). In this FIG. 10, there is a clear indication that the storage (i.e., elastic component) modulus rises sharply as the solution molarity is increased (remember at room temperature 2 M NaCl is approximately a theta solvent) whereas the loss (i.e., damping) modulus is barely affected.

Cryogels have a fairly low resolution with regard to their final properties because each thermal cycle produces a dramatic change in the material properties of the gel. The thetagels produced demonstrate that the concentration of the solvent produces a monotonic decrease in swelling ratio once the "theta" value is passed (See FIG. 7). Thus, the ultimate crosslink density can be fine tuned in proportion to the resolution achievable in the solvent concentration. For example, for the 10% PVA solution immersed in NaCl, the weight percentage of PVA in the final gel varies at a rate of about 7% per mole NaCl.

In preferred embodiments, the PVA thetagels can be made that exhibit a smooth gradient in spatial properties. Gradient properties cannot easily be manufactured in cryogels. Instead, the usual approach is to generate an array of stacked lamellae independently that must be joined in dissolved PVA and then cycled again. Sharp differences in modulus in such an array create a material with undesirable mechanical properties and with inhomogeneous interfaces. A preferred embodiment includes a composite annulus fibrosus/nucleus pulposus implant, that benefit from technology enabling a smooth gradient in mechanical properties, wherein a central lower modulus "pulposus" provides adequate compressive strength and a higher modulus peripheral "annulus" minimizes creep and undesirable distortion.

Modulus Enhancement: Incorporation of Ionic Species

For thetagels produced in NaCl, it is possible to include natural (hyaluronic acid) or synthetic (PAA) polymers to create gels with strain variable compressive moduli. Gelling a PVA/PAA solution in strong NaCl will shield the ionizable charges in the PAA while the PVA is crosslinked around the collapsed PAA. Re-equilibration in deionized water will allow expansion of the PAA and pre-stress the PVA matrix. The resulting construct has a very different mechanical compressive modulus due to the repulsion of the fixed charges on the incorporated PAA.

Generating Gradient Thetagel

In another preferred embodiment, to make the gradient thetagel: 10%, 20% and 30% solutions of 100 kg/mole PVA are made as described hereinbefore. A dialyzer cassette is split in half and each half bonded to one side of a 1×1×1 cm plexiglass box that is filled with the 10% PVA solution. The sealed box is placed into a temperature controlled "Ussing" style chamber where it is subjected to a constant 4 molar NaCl concentration difference (see FIG. 10). After the number of days where further changes in the gel are insignificant, the gradient gel is removed from the chamber and placed in deionized water for five days prior to further testing. Resulting gels are tested as described hereinbefore.

In another embodiment, spatial gradient can be generated using temporal oscillations in concentration. The concentration in the chamber can be modulated temporally to provide a gel, having a softer interior region than the peripheral region where a higher crosslinking occurs.

The chamber 100 includes a cartridge 140 containing a gel 160. The chamber can be divided into sub-chambers or regions including two immersion solvents 112 and 122. In a preferred embodiment, the solvents have the same concentration. In another preferred embodiment, the immersion solvents have different concentrations that cause a spatial gradient in the gel. Membranes 150, 154 are permeable membranes that allow the immersion solvents to selectively flow into the vinyl polymer solution. Membrane 130 provides an impermeable barrier to the flow of any solvent.

Dehydration

Preferred embodiments of the present invention are directed at controllably structuring gels. In a particular embodiment, in order to promote smooth dehydration and to homogenize the physical crosslinking of the PVA thetagel, the gel or solution of PVA may be immersed in a series of solutions, or in a bath of smoothly changing solvent quality, each with a higher Flory interaction parameter than the previous solution. This prevents the local "crashing out" of PVA at the surface directly in contact with the immersion solution. The term "crashing out" as used herein is associated with a phenomenon akin to precipitation because of the Flory interaction parameter. The polymer chains prefer to associate with themselves instead of the solvent as the Flory interaction parameter is above the theta point and thus precipitate or crash out.

In one preferred embodiment, a thetagel may be created by first immersing the contained PVA solution into a solvent which has a Flory interaction parameter that is higher than the theta point for the PVA solvent pair. After a period of time the contained PVA is immersed in another solvent, which has a Flory interaction parameter lower than the theta point for the PVA solvent pair. The process can continue with immersion of the contained PVA in solutions having successive decreases in the Flory interaction parameter until the desired interaction parameter value for the final gel is reached.

A method to form a thetagel in accordance with a preferred embodiment of the present invention includes immersing contained 5-20% PVA in DI, followed by immersion for a range of 1 hour to 1 day in 2.0 M NaCl, followed by immersion for a time period ranging between 1 hour to 1 day in 3.0 M NaCl, followed by immersion for a time period of 1 hour to 1 day in 4.0 M NaCl, and followed by immersion for a time period ranging from 1 hour to 1 day in 5.0 M NaCl.

In another preferred embodiment, the PVA solution may be subjected to a gradually changing solvent quality through a similar range of electrolyte concentrations by the gradual addition of a concentrated NaCl solution to a DI water bath such that the change of the salt concentration is slower, or equal to, the diffusion process into the gel.

A method in accordance with a preferred embodiment includes immersing contained 5-20% PVA in 1 liter of 1.5 M NaCl, and adding 6 M NaCl at a rate of 0.5 ml per minute to raise the electrolyte concentration at a rate of 0.0038 M/min and reaching 5 M NaCl after approximately 12 hours.

In another embodiment, the PVA solution may be subjected to one or many freeze-thaw cycles to fix the gel into a particular shape. It may then be immersed in a series of solutions having successively higher Flory interaction parameters until the final desired Flory parameter is reached.

A method in accordance with a preferred embodiment includes dissolving 5-20% PVA in DI, subjecting the solution to freeze-thaw cycles (approximately 1-8 cycles), and subsequently for a period ranging between 1 hour to 1 day, immersing the resultant gel in 2.0 M NaCl. The method further includes immersing the PVA gel for a time period of 1 hour to 1 day in 3.0 M NaCl, followed by immersion for a time period ranging from 1 hour to 1 day in 4.0 M NaCl and subsequently immersing for a time period of 1 hour to 1 day in 5.0 M NaCl.

In an alternate preferred embodiment, a method to form a gel includes dissolving a 5-20% PVA in DI, adding NaCl to the PVA solution to generate a concentration from 0.01 to 2 M NaCl in the PVA solution and then subjecting the PVA/NaCl solution to between 1 to 8 freeze-thaw cycles.

Nanostructuring

Polyvinyl alcohol gel is an extremely biocompatible material that can be made reasonably stiff without the use of chemical crosslinking or irradiation. However, the material properties of the PVA do not match the requirements of materials for use in load bearing applications such as, for example, artificial articular cartilage or intervertebral disks. A nanostructural enhancement of polymer systems in accordance with a preferred embodiment of the present invention indicates that PVA gels, which are already nearly suitable for use in load bearing orthopedic devices, may become viable candidates for such applications.

Nanostructuring polyvinyl alcohol theta and hydrogels—particles. The addition of particles to polymeric materials can improve the mechanical and thermal properties of the resulting material when compared to formulations of the neat polymer. Recently, it has been shown that the addition of nanoparticles to polymers can generate similar enhancements in the material properties, but with much lower particulate concentrations than those required of micron sized particles. This is particularly true when the material properties are dependent on surface area. In accordance with preferred embodiments, to strengthen polyvinyl alcohol thetagels or hydrogels, the dispersion of uncharged nanoscale particles or charged nanoscale particles with uniform or spatially varying surface charges into the solution prior to gelation enhances the mechanical and thermal properties of the final gel. Nanoscale particles, if dispersed properly, provide regular nucleation sites for physical crosslinking by adsorbing PVA chains to their surfaces in accordance with a preferred embodiment of the present invention. As in rubber toughened plastics, these nanoparticles also act as stress concentrators, thus toughening the gel. Nanoscale particles that may enhance the properties of PVA gels are, for example, clays (for example, but not limited to, Laponite, montmorillonite), fumed silica, titanium dioxide or hydroxyapatite. Surface treatments and modifications, such as end grafting of polymers also adjust the way in which the particles interact with the polymer gel matrix in accordance with a preferred embodiment of the present invention. These particles may also be biologically active, such as, for example, capable of releasing drugs to promote growth, or reduce inflammation. Nanostructuring is not limited to thetagels in accordance with a preferred embodiment of the present invention. However, the thetagels in accordance with the present invention allow the formation of physical crosslinks around charged particles under solution conditions where the debye length is reduced compared to the working solution. Thus when the gel is replaced in the working solution of lower electrolyte concentration the particles interact through electrostatic forces and add compressive strength to PVA thetagels as compared to PVA freeze-thaw gels.

In one embodiment, nanoparticles are dispersed into solutions of PVA. The solvent may be water, DMSO, methanol or any other solution that exhibits a Flory interaction parameter that is lower than the theta point for the PVA solvent pair during solution preparation. The PVA/nanoparticle mixture is then subjected to at least one freeze-thaw cycle. Subsequent to the freeze-thaw cycling, the gelled PVA is immersed in a solvent that has a Flory interaction parameter near or higher than the theta point for the PVA/solvent pair to induce further physical crosslinking of the PVA/nanoparticle mixture.

A method in accordance with a preferred embodiment of the present invention includes mixing: 5-20% PVA in DI with 1-10% fumed silica, freeze-thawing (1-8 cycles) the solution, followed by immersion for a time period ranging from 1 hour to 5 days in 2-5 M NaCl.

In another embodiment, the PVA/nanoparticle mixture is gelled by immersion into a solvent that has a Flory interaction parameter near or higher than the theta point for the PVA/solvent pair to induce physical crosslinking of the PVA/nanoparticle mixture. No freeze-thaw cycling is necessary in this embodiment.

A method in accordance with a preferred embodiment of the present invention includes mixing 5-20% PVA in DI with 1-10% fumed silica, followed by immersion for a time period ranging from 1 hour to 5 days in 2-5 M NaCl.

In another embodiment, the composite gels resulting from the two examples described hereinbefore are subject to further freeze-thaw cycles.

In another embodiment, PVA solutions or gels containing nanoparticles are subject to the dehydration protocol as described hereinbefore. A method in accordance with a preferred embodiment of the present invention includes mixing 5-20% PVA in DI with 1-10% fumed silica, subjecting the solution for 1-8 cycles of freeze-thawing, followed by immersion for a time period ranging from 1 hour to 1 day in 2.0 M NaCl, followed by immersion for a time period ranging from 1 hour to 1 day in 3.0 M NaCl, followed by immersion for a time period ranging from 1 hour to 1 day in 4.0 M NaCl and subsequently followed by immersion for a time period ranging from 1 hour to 1 day in 5.0 M NaCl.

Nanostructuring polyvinyl alcohol thetagels and cryogels—functionalized molecular additives. The addition of particles to the PVA solution prior to gelation can provide enhancement of the thermal and mechanical properties of the gel. However, there is a class of molecular additives that can be functionalized to promote physical crosslinking and can simultaneously act as stress concentrators. Polyhedral oligomeric silsesquioxane (POSS) can enhance mechanical properties of polymeric materials. Since the POSS molecules can be functionalized, they can be tuned to associate with the PVA chains to enhance interchain crosslinking and to act as stress concentrators. Their extremely small size and large number of functionalized groups has the potential to provide better results than nanoparticle seeding.

All of the methods for generating thetagels or cryogels described hereinbefore may be applied to solutions containing dispersed functionalized POSS molecules. In one preferred embodiment, POSS functionalized to display negatively charged oxygen groups can be used to promote hydrogen bonding. The functionalized POSS is dispersed into aqueous PVA solution and subjected to theta or freeze-thaw gelation (ranges 0.01 mM to 1 M OctaTMA POSS (tetramethyl ammonium salt) and 5-20% PVA in solution).

In another preferred embodiment, POSS functionalized to display alcohol groups is dispersed into PVA and subjected to theta or freeze-thaw gelation (ranges 0.01 mM to 1 M Octahydroxypropyldimethylsilyl POSS and 5-20% PVA in solution)

In another embodiment, POSS functionalized to display at least one PVA chain and at least one carboxyl or sulfate group can be used to produce an extremely hydrophilic, tough artificial cartilage. The preferred POSS construct has at least one PVA chain at opposite corners of the POSS with the 6 remaining functional groups expressing sulfate or carboxyl groups. This structure can be "stitched" into the PVA gel network via the thetagel process or freeze-thawing to produce an artificial cartilage with tunable properties.

Figure 12:
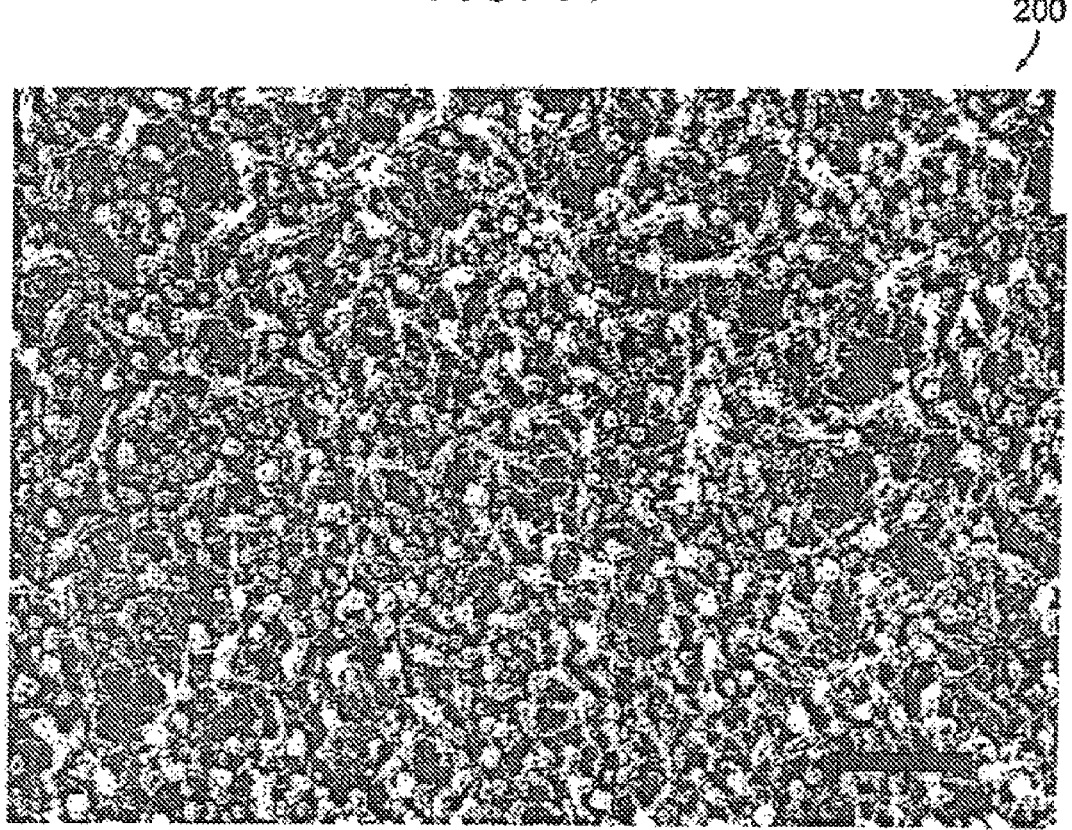
FIG. 12 illustrates a quick freeze deep etch (QFDE) image of PVA gel structure in accordance with a preferred embodiment of the present invention wherein the PVA gel is formed by immersion in 5 M NaCl for 3 days. The bar represents 100 nm.

FIG. 12 illustrates a quick freeze deep etch (QFDE) image of PVA gel structure in accordance with a preferred embodiment of the present invention wherein the PVA gel is formed by immersion in 5 M NaCl for 3 days. The bar represents 100 nm. QFDE preserves the gel structure in its hydrated state.

Figure 13A:
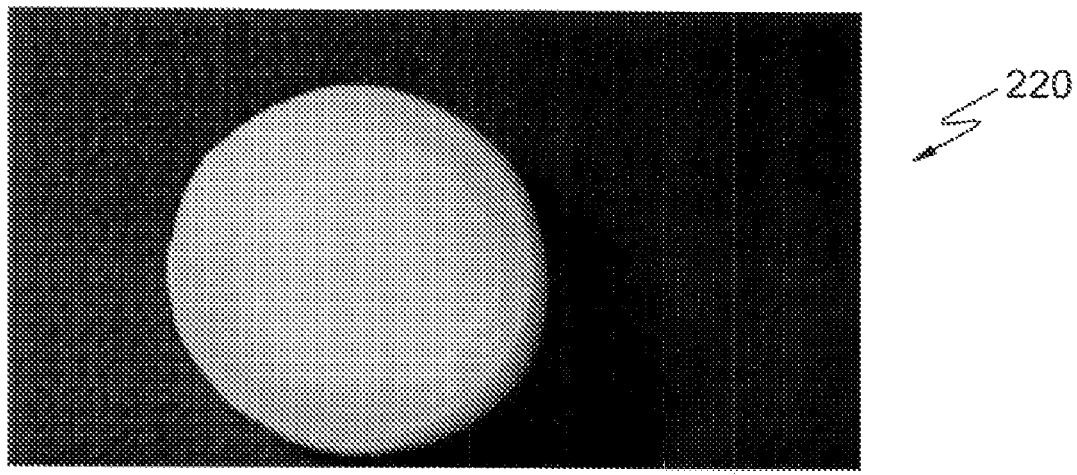
FIGS. 13A and 13B are a cross-sectional and a close-up view of the cross-section of a PVA gradient hydrogel, respectively, prepared by filling Plexiglass tubing with 10% PVA solution, performing one freeze thaw cycle (8 hours at −21° C.; 4 hours at room temperature) then immersing in 3 M NaCl bath for at least 3 days, then dehydrating in air for 60 hours and returning to deionized (DI) water in accordance with a preferred embodiment of the present invention.
Figure 13B:
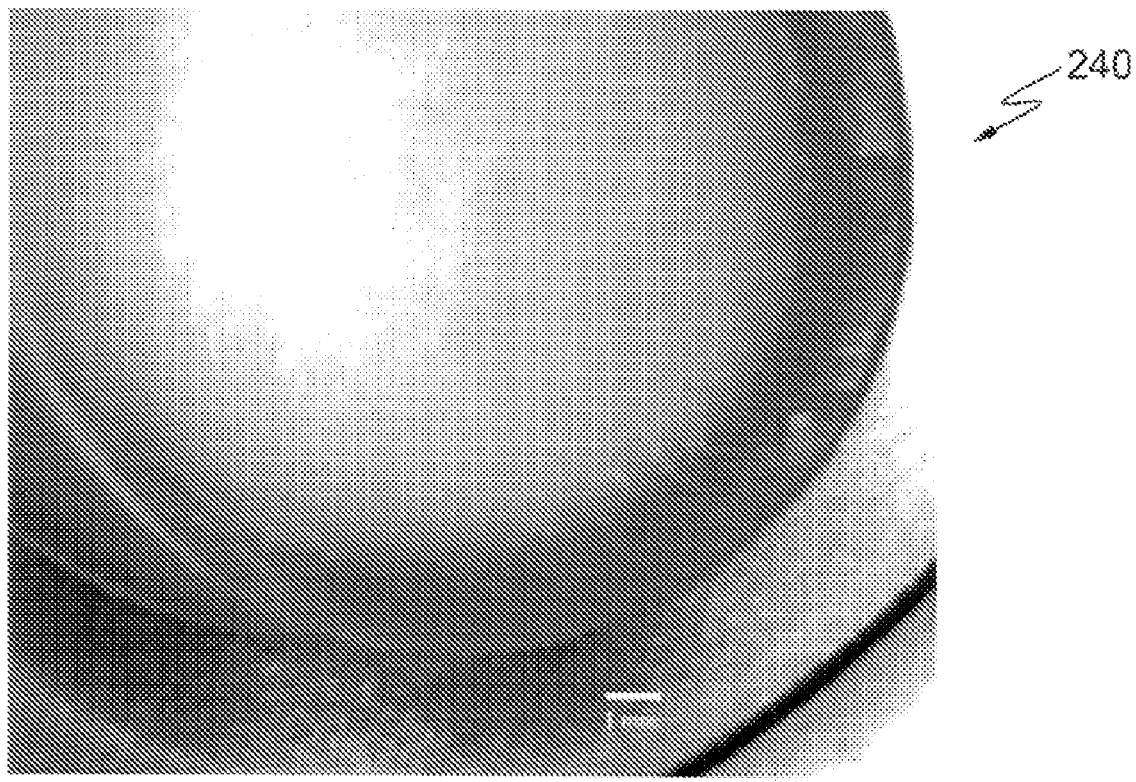

FIGS. 13A and 13B are a cross-sectional and a close-up view of the cross-section of a PVA gradient hydrogel, respectively, prepared by filling Plexiglass tubing with 10% PVA solution, performing one freeze thaw cycle (8 hours at −21° C.; 4 hours at room temperature) then immersing in 3 M NaCl bath for at least 3 days, and subsequently dehydrating in air for 60 hours and returning to deionized (DI) water in accordance with a preferred embodiment of the present invention. FIGS. 13A and 13B illustrate the presence of radial gradients in PVA induced by air dehydration.

Figure 14:
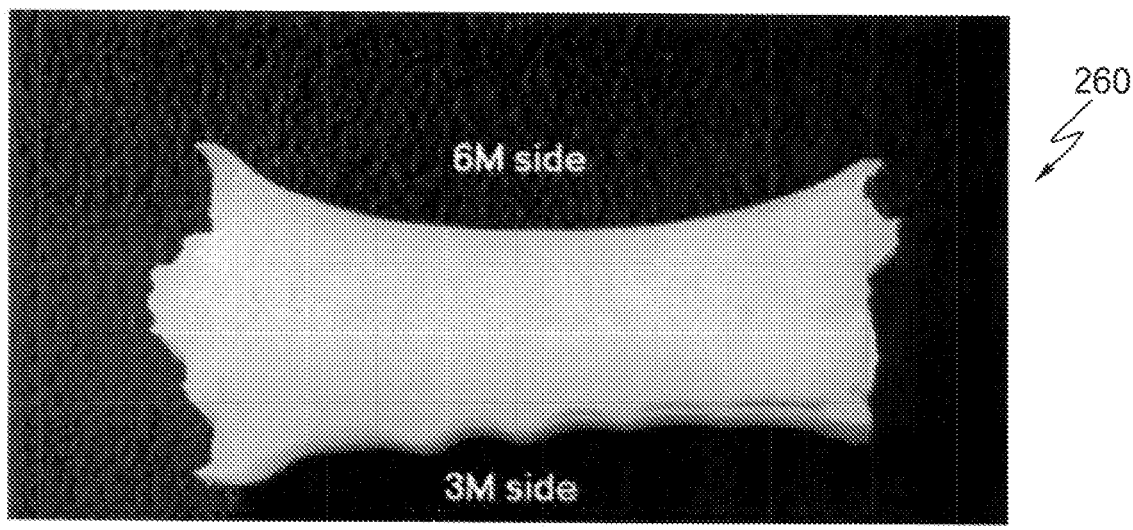
FIG. 14 illustrates a cross-sectional view of a PVA gradient hydrogel prepared by filling dialysis cartridge with 10% PVA solution, then immersing in a chamber having 3 M NaCl on one side and 6 M NaCl on the other side for 3 days in accordance with a preferred embodiment of the present invention.
Figure 15:
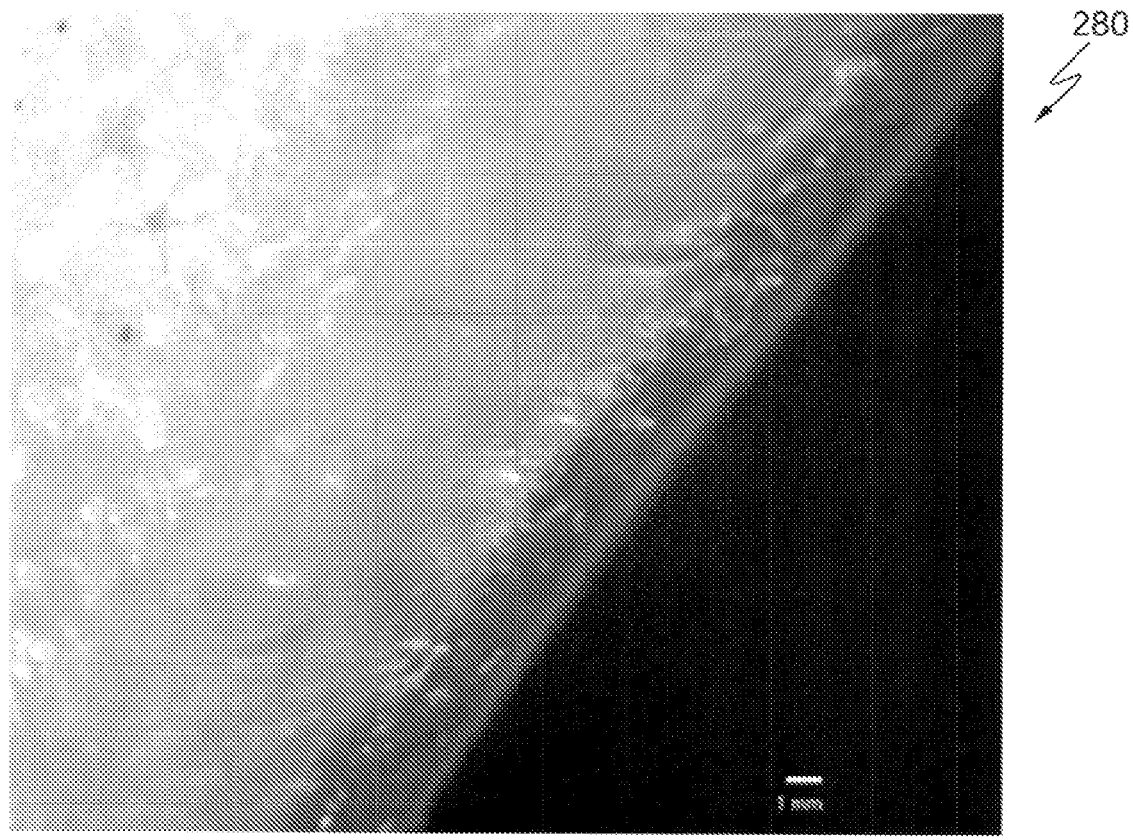
FIG. 15 illustrates a close-up view of the cross-section of the PVA gradient hydrogel of FIG. 14 on the 6 M NaCl side prepared by filling the dialysis cartridge with 10% PVA solution, and then immersing in a chamber with 3 M NaCl on one side and 6 M NaCl on the other for 3 days.

FIG. 14 illustrates a cross-sectional view of a PVA gradient hydrogel prepared by filling dialysis cartridge with 10% PVA solution, then immersing in a chamber having 3 M NaCl on one side and 6 M NaCl on the other side for 3 days in accordance with a preferred embodiment of the present invention. FIG. 15 illustrates a close-up view of the cross-section of the PVA gradient hydrogel of FIG. 14 on the 6 M NaCl side prepared by filling the dialysis cartridge with 10% PVA solution, and then immersing in a chamber with 3 M NaCl on one side and 6 M NaCl on the other for 3 days. FIGS. 14 and 15 illustrate the presence of linear gradients in PVA induced by static NaCl solution gradient.

Figure 16:
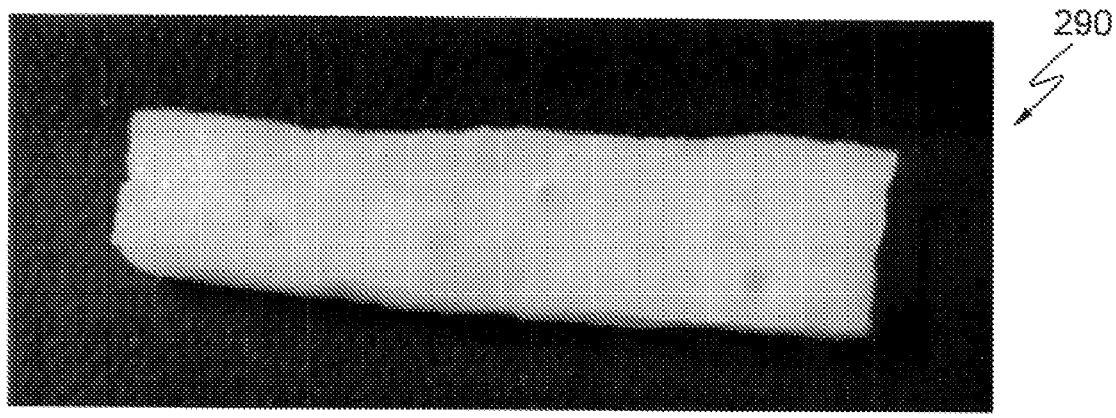
FIG. 16 illustrates a nanostructured PVA hydrogel prepared by mixing a solution of 10% PVA and 2 weight percent Laponite clay, subjecting to a 1 freeze-thaw cycle, then exposing to a 4 M NaCl solution for at least 3 days in accordance with a preferred embodiment of the present invention.

FIGS. 16-19 illustrate nanostructured PVA gels in accordance with preferred embodiments of the present invention. More particularly, FIG. 16 illustrates a nanostructured PVA hydrogel prepared by mixing a solution of 10% PVA and 2 weight percent Laponite clay, subjecting to a 1 freeze-thaw cycle, then exposing the solution to a 4 M NaCl solution for at least 3 days in accordance with a preferred embodiment of the present invention.

Figure 17:
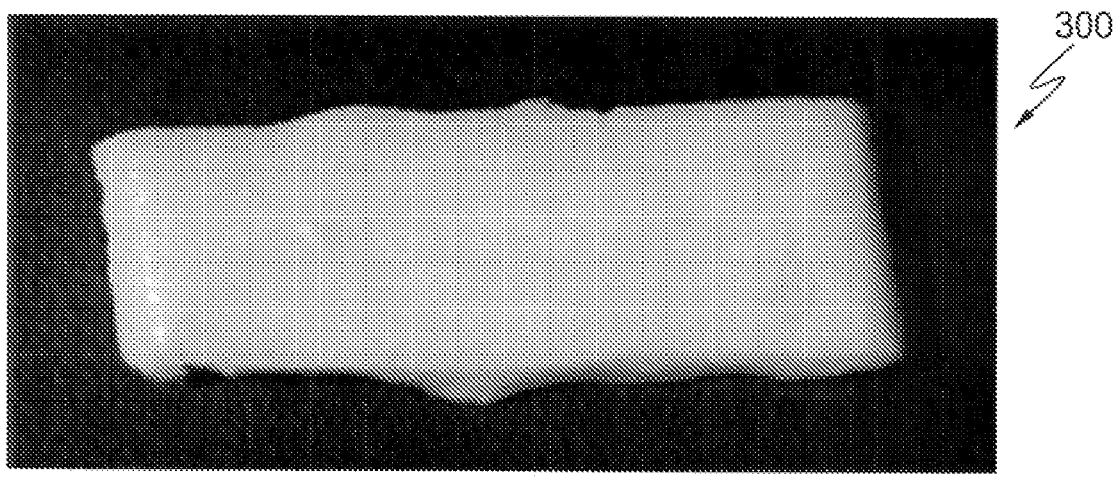
FIG. 17 illustrates a nanostructured PVA hydrogel prepared by mixing a solution of 10% PVA and 4 weight percent of silica, titrating to pH=3, subjecting to a 1 freeze-thaw cycle, then exposing to a 4 M NaCl solution for at least 3 days in accordance with a preferred embodiment of the present invention.

FIG. 17 illustrates a nanostructured PVA hydrogel prepared by mixing a solution of 10%, PVA and 4 weight percent of silica, titrating to pH=3, subjecting to a 1 freeze-thaw cycle, then exposing to a 4 M NaCl solution for at least 3 days in accordance with a preferred embodiment of the present invention.

Figure 18:
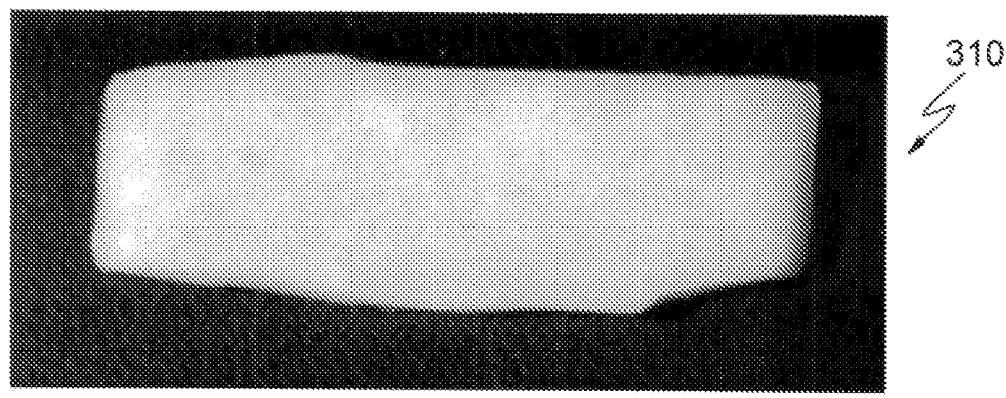
FIG. 18 illustrates a nanostructured PVA hydrogel prepared by mixing a solution of 10% PVA and 4 weight percent silica, titrating to pH=10, subjecting to 1 freeze-thaw cycle, then exposing to 4 M NaCl solution for at least 3 days in accordance with a preferred embodiment of the present invention.

FIG. 18 illustrates a nanostructured PVA hydrogel prepared by mixing a solution of 10% PVA and 4 weight percent silica, titrating to pH=10, subjecting to 1 freeze-thaw cycle, then exposing to 4 M NaCl solution for at least 3 days in accordance with a preferred embodiment of the present invention.

Figure 19:
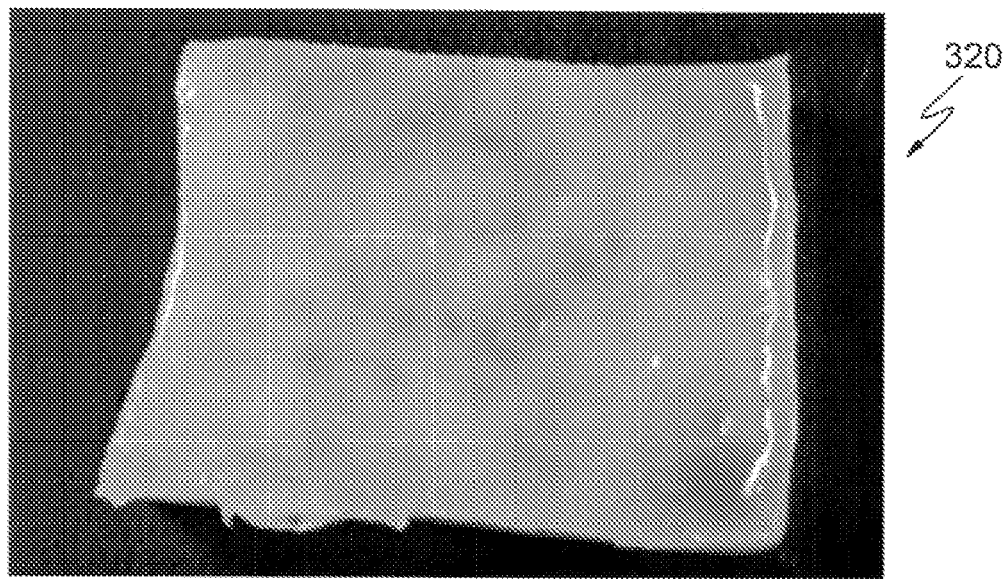
FIG. 19 illustrates a nanostructured PVA hydrogel prepared by mixing a solution of 10% PVA and an octatetramethylammonium polyhedral oligomeric silsesquioxane (OctaTMA POSS) in water, then subjecting to 1 freeze-thaw cycle in accordance with a preferred embodiment of the present invention.

FIG. 19 illustrates a nanostructured PVA hydrogel prepared by mixing a solution of 10% PVA and 0.001 M octaTMA POSS in water, then subjecting to 1 freeze-thaw cycle in accordance with a preferred embodiment of the present invention.

Figure 20:
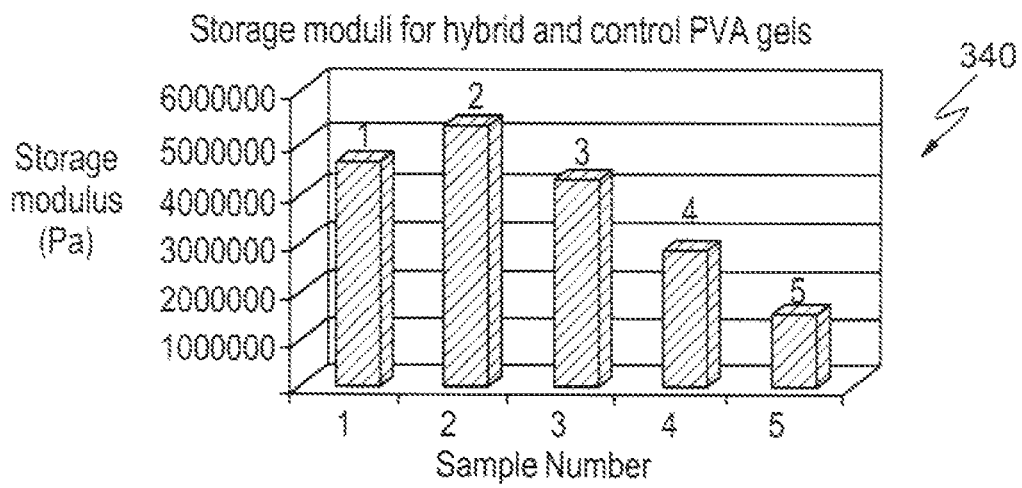
FIG. 20 graphically illustrates the storage modulus for hybrid and control PVA gels in accordance with a preferred embodiment of the present invention.

FIG. 20 graphically illustrates storage moduli for hybrid and control PVA gels in accordance with preferred embodiments of the present invention. The graphs are results of DMA testing on 4% silica/PVA nanostructured gel having a pH=10 (sample number 1), 4% silica/PVA nanostructured gel having a pH=3 (sample number 2), 2% Laponite/PVA nanostructured gel (sample number 3), 0.001 M, 10% PVA+octaTMA POSS (sample number 4), and a control gel (sample number 5). All gels were subjected to 1 freeze-thaw cycle and then immersed in 3 M NaCl for three days. Prior to DMA testing the samples were equilibrated in DI water for at least 24 hours.

The embodiments of the present invention provide methods or the controlled manipulation of the Flory interaction parameter in a solution of vinyl polymer, in particular polyvinyl alcohol, to yield a workable fluid that gels in a controlled manner. The control of the solvent condition allows control of the gelation rate, which results in a time period in which the PVA solution has only partially gelled, thus permitting manipulation or working of the precursor gel prior to final gelation. During this time period the PVA solution is substantially fluid and can be injected, pumped, molded, or undergo any other manipulative processing step. The final properties of the hydrogel, which include, but are not limited to, percentage crystallinity, crystal size, free volume, and mechanical properties, are influenced by the initial vinyl polymer concentration, the gellant concentration, (i.e., the final solvent quality) in the final mixture, the processing temperature, and the mixing procedure.

Figure 21A:
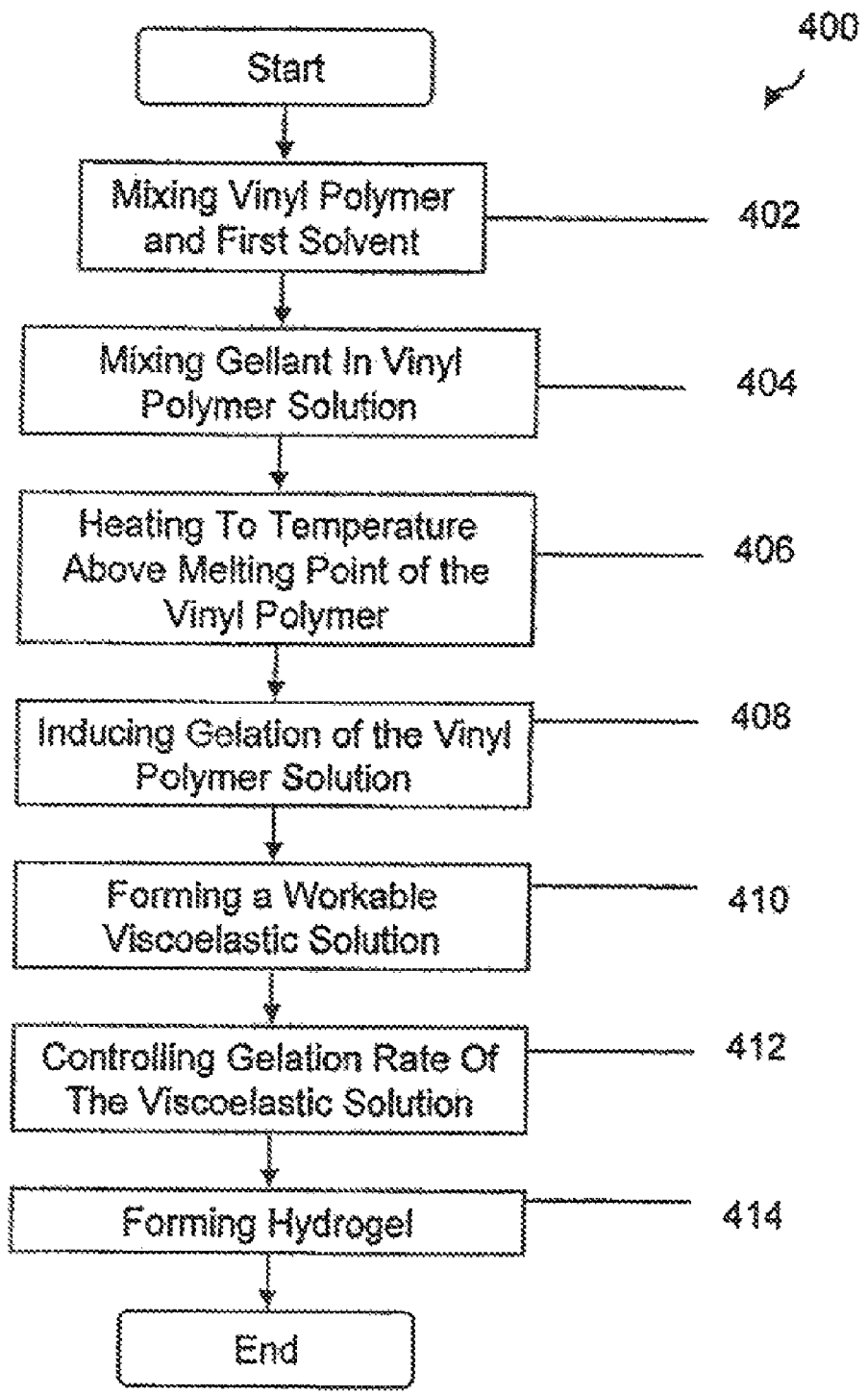
FIG. 21A illustrates a flow chart of a method of forming a PVA hydrogel in accordance with a preferred embodiment of the present invention.

One preferred embodiment of the method is shown in FIG. 21A. FIG. 21A illustrates a flow chart of a method 400 of forming a PVA hydrogel including the step 402 of mixing a vinyl polymer and a first solvent; mixing a gellant in the vinyl polymer solution per step 404; and preventing gelation of the vinyl polymer physical associations by heating the mixture to a temperature above the melting point of the vinyl polymer per step 406. More particularly, this temperature is above the melting point of any physical associations formed in the vinyl polymer. In an alternate embodiment, step 406 precedes step 404. The method 400 further includes the step 408 of inducing gelation of the vinyl polymer solution; forming a transiently workable viscoelastic solution per step 410; controlling or modulating the gelation rate of the viscoelastic solution per step 412, for example, by modulating at least one of the temperature, the pressure and the concentration gradient; and forming the hydrogel per step 414 in accordance with a preferred embodiment of the present invention.

Figure 21B:
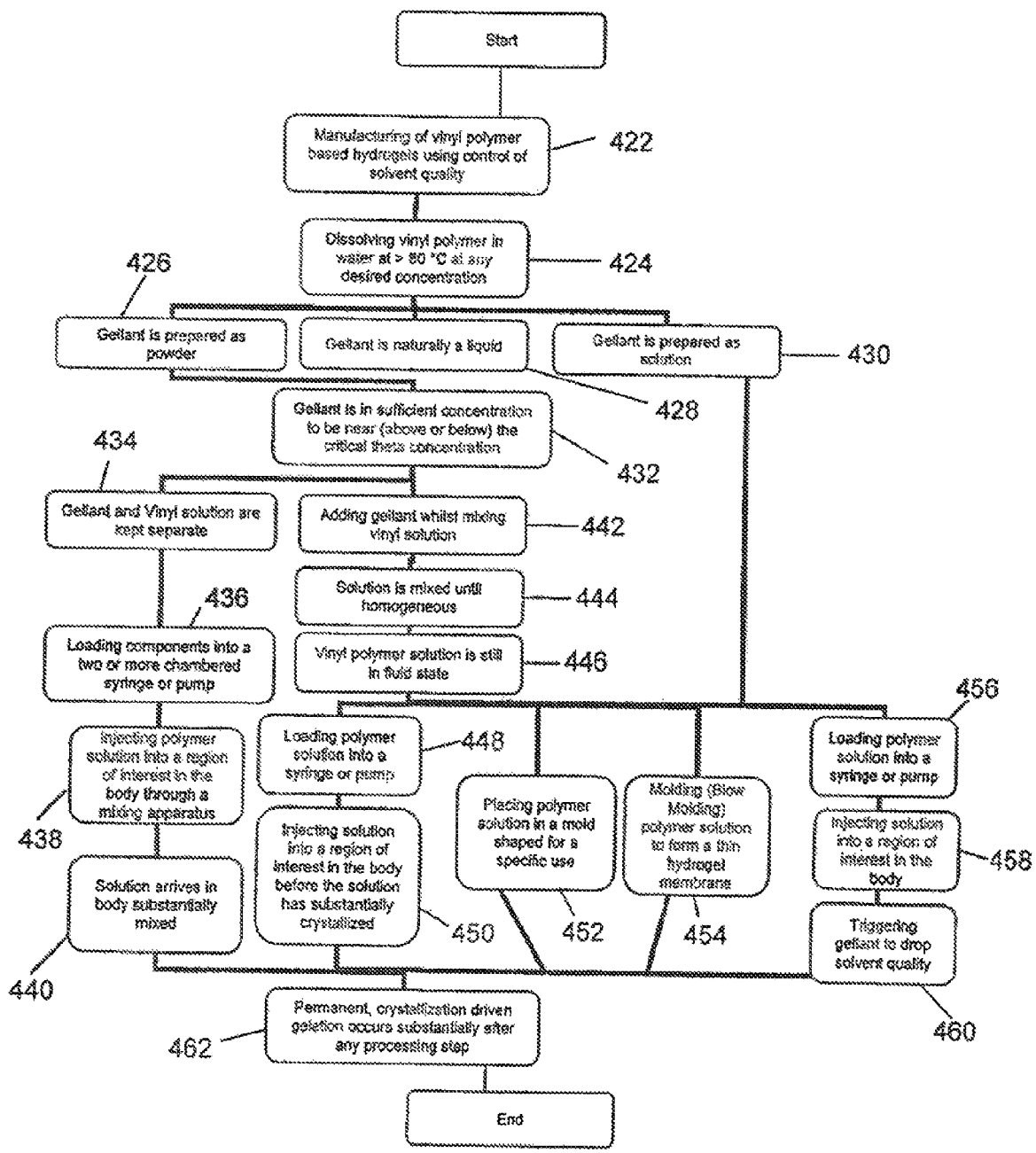
FIG. 21B illustrates a flow chart of methods of forming and providing a vinyl polymer hydrogel in accordance with preferred embodiments of the present invention.

FIG. 21B illustrates a flow chart of methods of forming and providing a vinyl polymer hydrogel in accordance with preferred embodiments of the present invention. Theses methods are directed at manufacturing vinyl polymer based hydrogels by modulating solvent quality. The methods include the step 424 of dissolving vinyl polymer in water at, for example, greater than 80° C. at any desired concentration. The next step includes the preparation of a gellant as a powder per step 426, or as a solution per step 430. The gellant can naturally be a liquid per step 428. The next step 432 includes providing a gellant in sufficient concentration to be near (above or below) the critical theta condition of a subsequent mixture when added to the vinyl polymer solution. The method then includes the step 434 wherein the gellant and vinyl solution are kept separately, the step 436 of loading the components into a two or more chambered device such as a syringe or a pump, and the step 438 of injecting the polymer solution into a region of interest, such as a cavity in the body through a mixing apparatus. The solution arrives in the region of interest substantially mixed per step 410.

The method 400 after step 432 can alternatively include the step 442 of adding the gellant while mixing the vinyl solution, the step 444 wherein the solution is mixed until it is homogenous and step 446 wherein the vinyl polymer solution is still in a fluid and workable state. The method 400 can include the step 448 of loading the polymer solution into a syringe or pump followed by step 450 of injecting the solution into the region of interest in the body before the solution has substantially crystallized. In the alternative, after step 446, the method 400 can include the step 452 of placing the polymer solution in a mold shaped for a specific use or the step 454 of blow molding the polymer solution to form a thin hydrogel membrane or per step 456 of loading the polymer solution into a syringe or pump. Step 458 follows by injecting the solution into the region of interest and per step 460 triggering the gellant to drop solvent quality. Step 462 can follow the processing steps 440, 450, 452, 454 or 460 alternatively and includes the permanent crystallization of the gellant that occurs substantially after the above listed processing steps.

In several embodiments, the vinyl polymer is highly hydrolyzed polyvinyl alcohol of about 50 kg/mol to about 300 kg/mol molecular weight. The vinyl polymer solution is about 1 weight percent (wt %) to about 50 wt % of polyvinyl alcohol based on the weight of the solution. In preferred embodiments, the vinyl polymer solution is about 10 weight percent to about 20 weight percent solution of polyvinyl alcohol based on the weight of the solution.

The first solvent is selected from a group of solvents having a low $\chi$ value that is not sufficient to enable gelation. In several preferred embodiments, the first solvent is selected from the group including, but not limited to, of deionized water, dimethyl sulfoxide, a $C_1$ to $C_6$ alcohol and mixtures thereof.

The second solvent, the gellant, is selected from a group of solvents having the property that raises the $\chi$ value of the resultant mixture of gellant and vinyl solution to $\chi > 0.5$ at a specified temperature. In several embodiments, the gellant is selected from the group including, but not limited to, for example, alkali salts, glycosaminoglycans, proteoglycans, oligomeric length hydrocarbons such as polyethylene glycol, enzyme-cleavable biopolymers, UV-cleavable polymers, chondroitin sulfate, starch, dermatan sulfate, keratan sulfate, hyaluronic acid, heparin, heparin sulfate, biglycan, syndecan, keratocan, decorin, aggrecan, perlecan, fibromodulin, versican, neurocan, brevican, a phototriggerable diplasmalogen liposome, amino acids such as, for example, serine or glycine, glycerol, sugars or collagen. The gellant can be added in the form of a solid or as an aqueous solution.

In one preferred embodiment, the gellant is added by being mixed with a solution of the vinyl polymer held at an elevated temperature, preferably above the melting point of the vinyl polymer. The melting point can be suitably determined by differential scanning calorimetry (DSC). With reference to the dashed curve illustrated in FIG. 6, for PVA, the elevated temperature is at least greater than 57 degrees Celsius, preferably greater than 80 degrees Celsius, more preferably greater than 90 degrees Celsius. In general, with reference to a graphical representation of differential scanning calorimetry results such as FIG. 6, the most preferred elevated temperature is in the linear portion of the curve at temperatures above the melting point.

The resultant mixture begins to undergo a spinodal decomposition as it mixes and cools. The mixture is injected into a body cavity, whereupon it forms a load-bearing gel over a period of time.

In one preferred embodiment the solvent quality of the entire mixture of PVA, water and secondary or tertiary components has a Flory interaction parameter of $0.25 < \chi < 0.8$ and preferably in the range of $0.3 < \chi < 0.5$.

The preferred embodiments of the invention provide an injectable hydrogel that can be used for orthopedic therapies, including nucleus pulposus augmentation or replacement, and augmentation of load bearing surfaces in an articulated joint such as, for example, knee or hip. In the case of knee or hip augmentation, the injectable hydrogel can be used in early interventional therapy for those patients who, although in pain due to partial loss of articular cartilage, are not candidates for total knee or hip replacement.

The injectable hydrogel can also be used for non-load bearing applications for replacement, repair, or enhancement of tissue. It can also be used topically as a protective coating for burns or wounds. The preferred embodiments of the invention are especially suited to minimally invasive applications where small access holes in tissue are required. The access holes can have diameters of approximately 1-10 mm and can be located for example, without limitation, in the annulus fibrosis, bone tissue, cartilage, or other tissues.

In another preferred embodiment, the gellant is added to a mixing solution of the vinyl polymer held at an elevated temperature. The resultant mixture begins to undergo a spinodal decomposition as it mixes and cools. This mixture can then be used to generate a hydrogel device to be manufactured using conventional processing means such as injection or compression molding, blow molding, calendaring, or any other suitable processing step. This device can then be implanted as a load bearing device, or some other non-load bearing device such as a nerve cuff or as part of a drug release system. This device can also be used in non-biological applications as protective hydrogel films, or sealing agents.

Figure 28A:
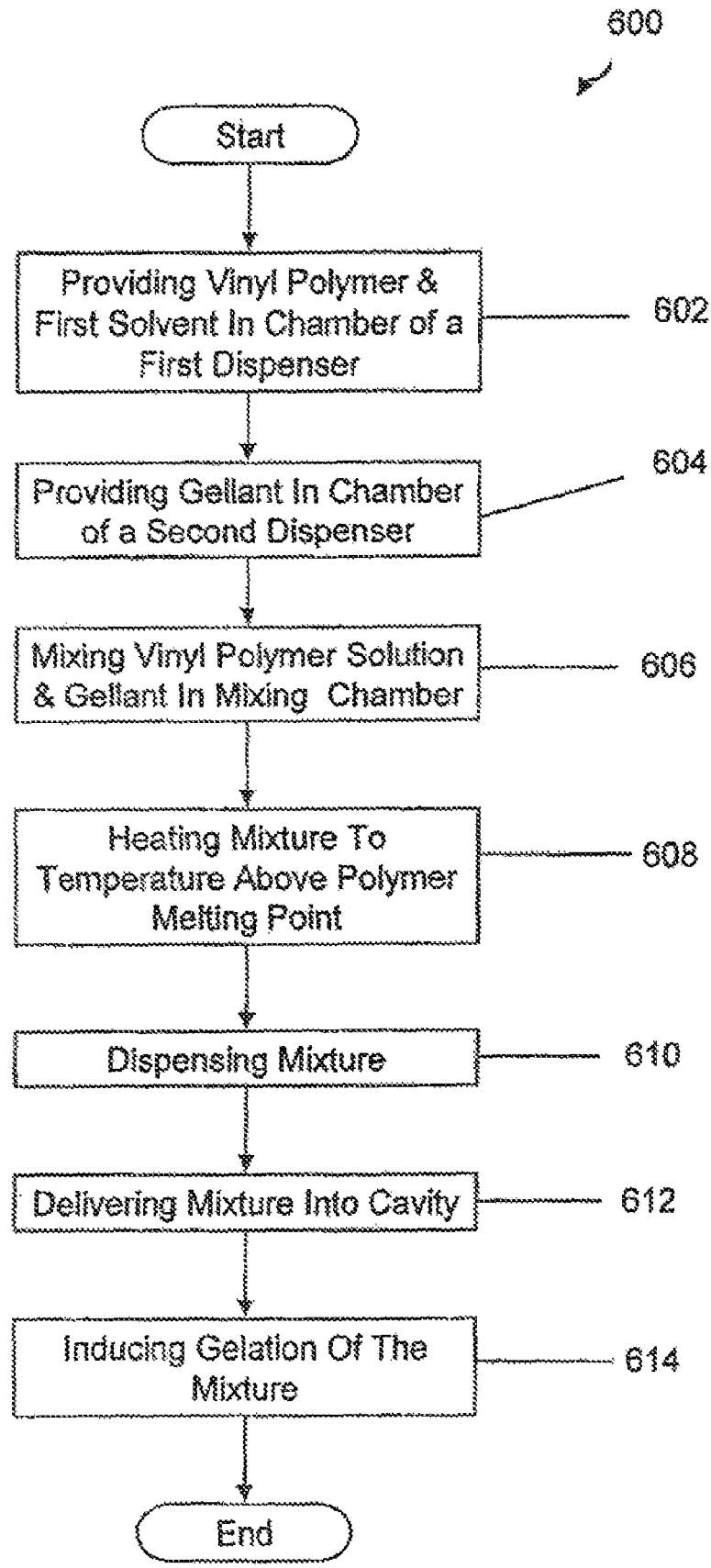
FIGS. 28A-28C illustrate flow charts of methods for forming a PVA hydrogel in accordance with preferred embodiments of the present invention.

In another embodiment, the vinyl solution and gellant are not pre-mixed, but are co-injected through a tube via a mixing, chamber having a tortuous path that facilitates mixing. The pre-cursor hydrogel can be injected using a suitable dispenser directly into the target location. FIG. 28A illustrates a flow chart of method 600 of forming a PVA hydrogel including the steps of providing a vinyl polymer and a first solvent in a chamber of a first dispenser per step 602; placing a gellant in a chamber of a second dispenser per step 604; mixing the vinyl polymer solution and the gellant in a mixing chamber per step 606 and heating the mixture to a temperature above the melting point of the vinyl polymer 608. The method then includes dispensing the mixture per step 610; delivering the mixture into a region of interest, such as a cavity, per step 612; and inducing gelation of the mixture per step 614 to form a PVA hydrogel in accordance with a preferred embodiment of the present invention. In certain embodiments, the step of providing a vinyl polymer and a first solvent includes the step of mixing the vinyl polymer and the first solvent. Similarly, in certain embodiments, the step of placing the gellant in a chamber of the second dispenser chamber includes the step of mixing the gellant and a second solvent.

Figure 28B:
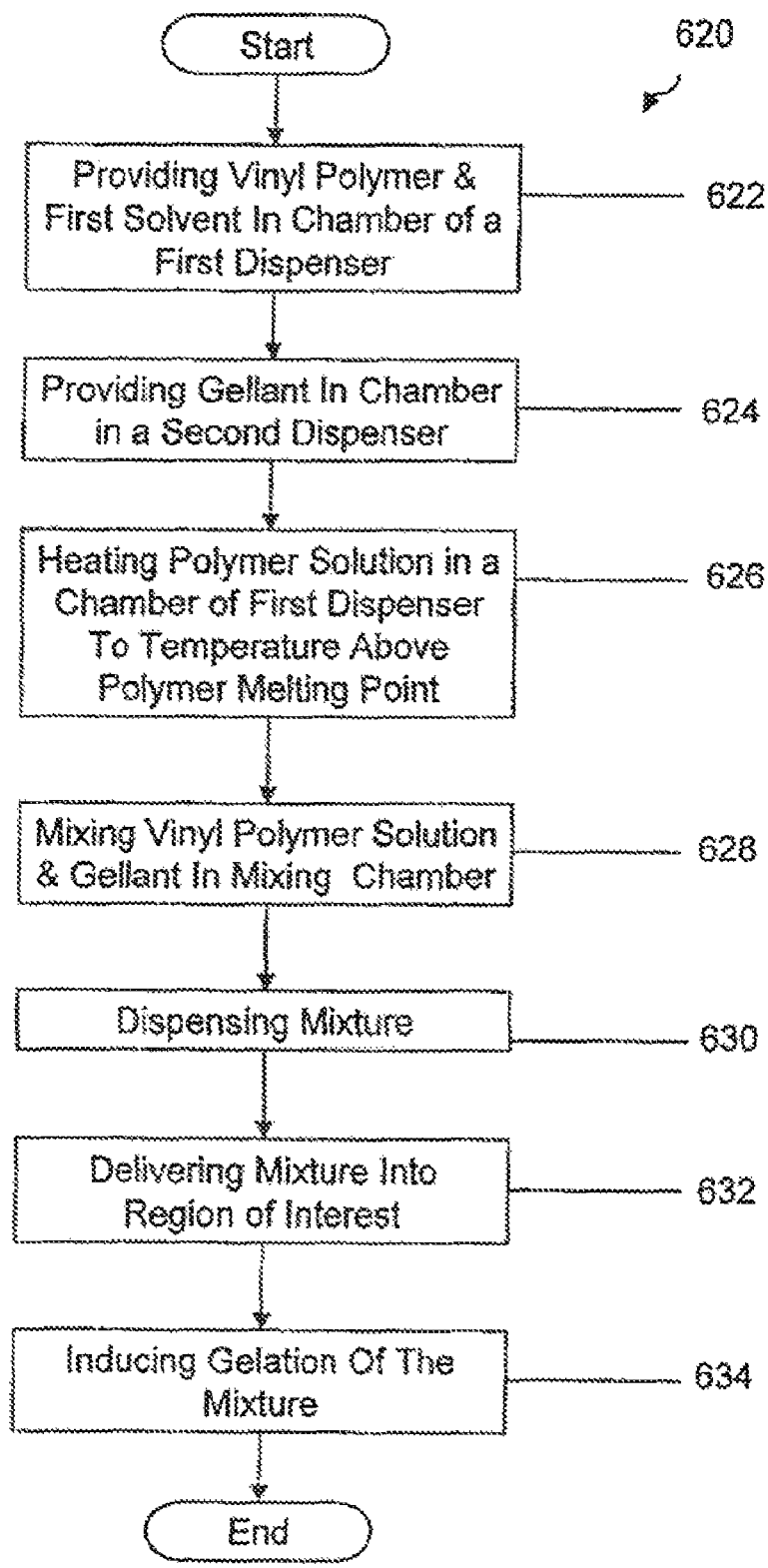

FIG. 28B illustrates a flow chart of a method 620 of forming a PVA hydrogel in accordance with an alternate preferred embodiment. This method 620 is similar to the method 600 illustrated with respect to FIG. 28A however, the step of heating the polymer solution in a chamber of a first dispenser to a temperature above the melting point of physical associations in the polymer (step 626) precedes the step of mixing the vinyl polymer solution and the gellant in the mixing chamber (per step 628).

The step of inducing gelation as discussed with respect to the flow charts in FIGS. 28A and 28B includes the modution of temperation, in particular to lowering the temperature of the mixture of the vinyl polymer solution and the gellant below the crystallization temperature (melting point of the physical association). In alternate preferred embodiments the step of inducing gelation includes the release of active gellants from an inactive gellant complex. The inactive gellant complex includes, without limitation, for example, enzyme cleavable polymers, heat denaturable polymers, thermal/chemical/photo/triggered liposomes or hydrogels; thermally triggered irreversible crystalline materials such as starches, and degradable polymers.

Figure 28C:
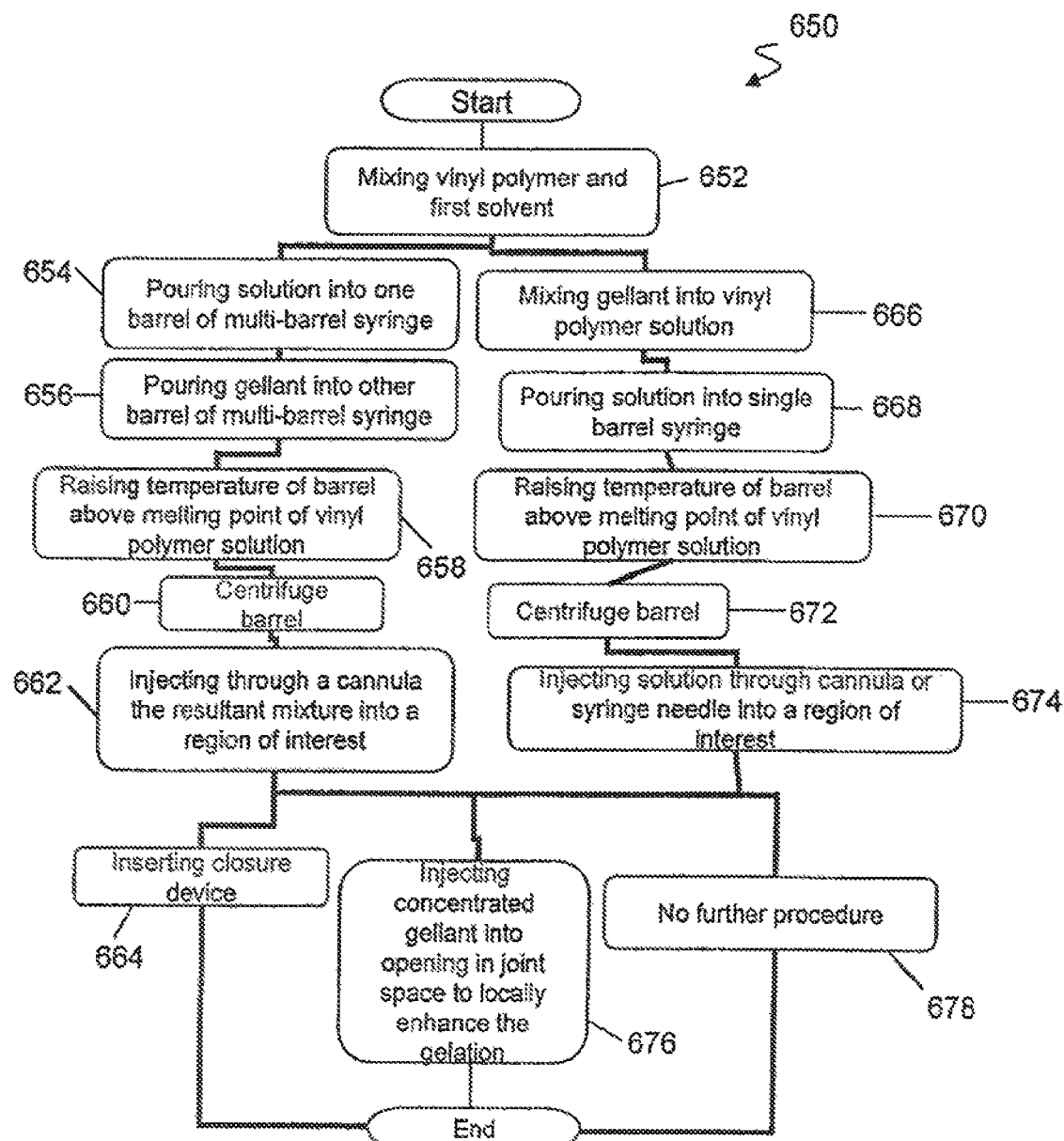

FIG. 28C illustrates a flow chart of a method 650 for forming a vinyl polymer hydrogel in accordance with a preferred embodiment of the present invention. The method 650 includes mixing a vinyl polymer and first solvent per step 652. The method 650 includes the step 654 of pouring the solution into one barrel of a multi-barrel syringe, pouring a gellant into another barrel of the multi-barrel syringe per step 656, raising the temperature of the barrel above the melting point of the physical associations of the vinyl polymer per step 658, centrifuge the barrel per step 660, and injecting through a static mixture such as a cannula having a tortuous path the mixture into a region of interest, for example, into a joint space per step 662.

The method 650 includes in an alternate embodiment the step of 666 of mixing a gellant into a vinyl polymer solution, pouring the solution into a single barrel per step 668, raising the temperature of the barrel above the melting point of the vinyl polymer physical associations per step 670, centrifuging the barrel per step 672, and injecting the solution through a cannula or a syringe needle into the region of interest per step 674. The steps of the method 650 can thus provide material such as nucleus pulposus augmentation for a disk system. This gel in accordance with the preferred embodiments conforms to the joint space or any region of interest.

Further, the method 650 includes for the different embodiments the following steps of inserting a closure device for a disk augmentation per step 664 or injecting concentrated gellant into an opening in the joint space to locally enhance the gelation rate and final mechanical properties per step 676 or per step 678 requiring no further procedure post the injection of the gellant into the region of interest per steps 662, 674. The latter steps 664, 676, provide for the augmentation of, for example, the annulus fibrosis in a disk system.

Figure 29A:
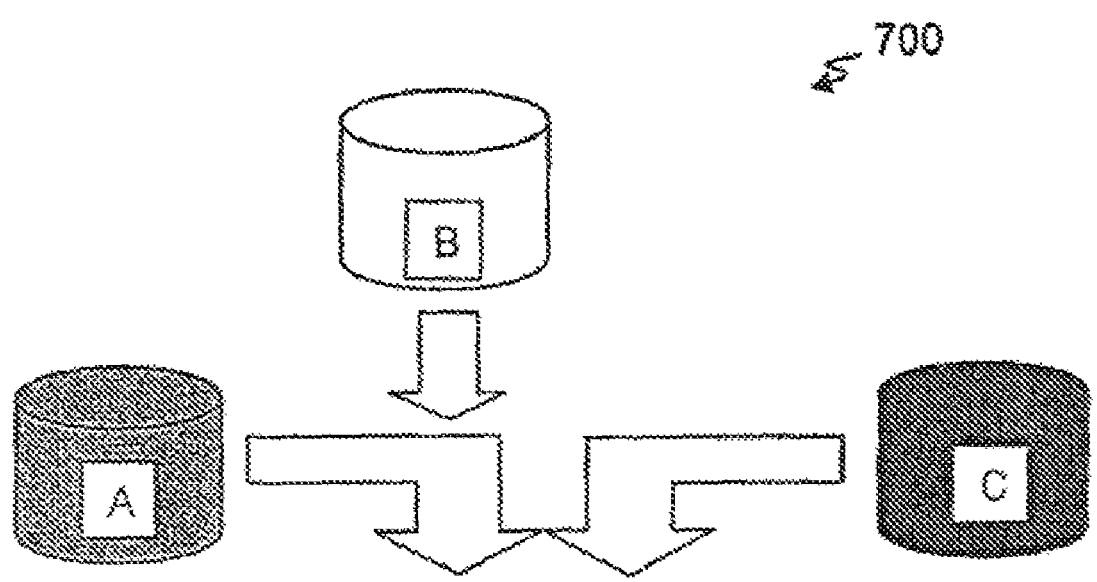
FIGS. 29A-29F schematically illustrate a method for forming and dispensing a vinyl polymer hydrogel in accordance with a preferred embodiment of the present invention.
Figure 29B:
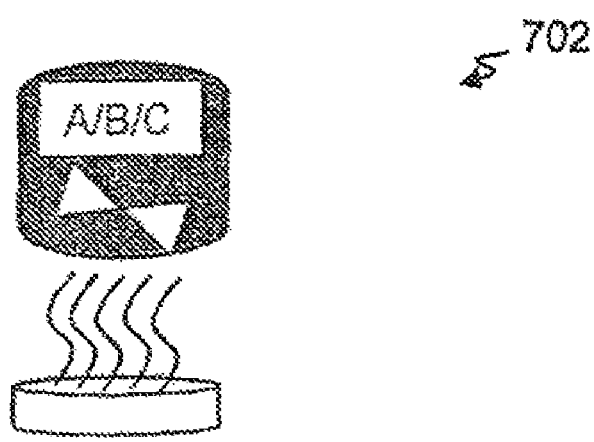
Figure 29C:
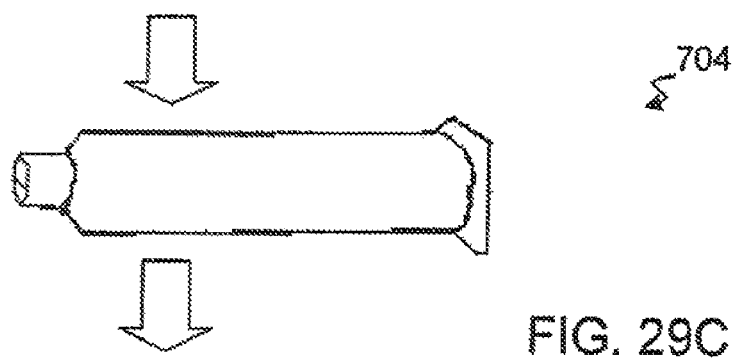
Figure 29D:
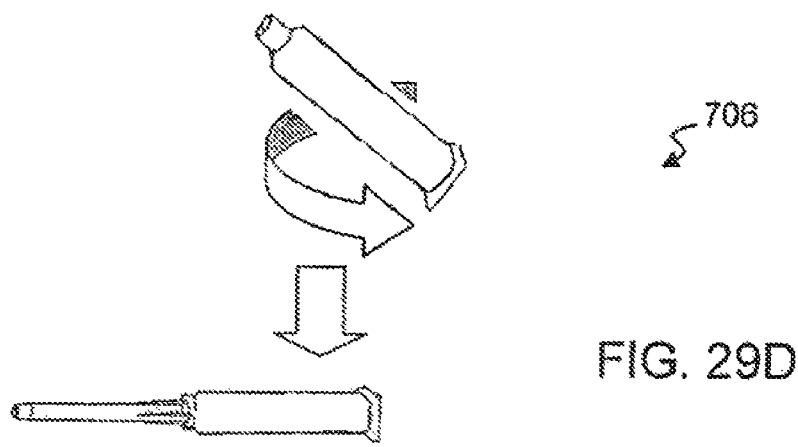
Figure 29E:
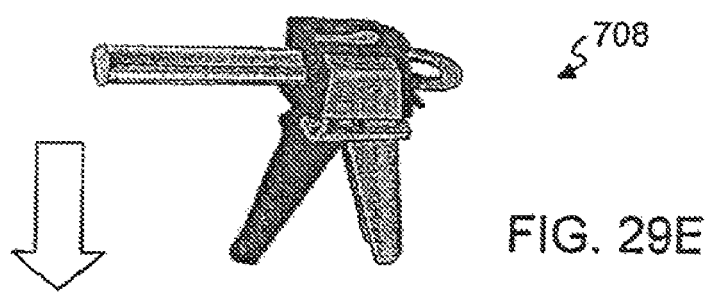
Figure 29F:
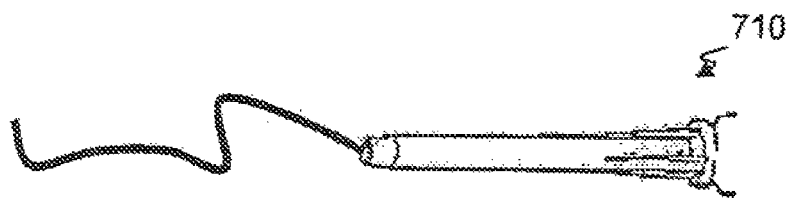

FIGS. 29A-29F schematically illustrate a method 700 for forming and dispensing a vinyl polymer hydrogel in accordance with a preferred embodiment of the present invention. The method, includes per FIG. 29A, a system being supplied in three aseptic containers or two containers wherein the contents of the containers A and B are combined. The aseptic cartridges contain PVA, solvent 1 (water) and gellant, respectively, as illustrated in FIG. 29B. The two components are mixed in a sealed container at a temperature above 80° C. The components are then transferred to a single barreled holder 704 as illustrated in FIG. 29C and centrifuged whilst maintaining temperature to remove bubbles per FIG. 29D. As illustrated in FIG. 29E, a nozzle or syringe needle is attached to the single barreled holder which is then assembled onto a plunger system that can be mechanically or electrically actuated (ratcheted) to deliver the mix solution. As described herein before, the mixed solution flows for a short period of time before becoming unworkable.

Figure 30A:
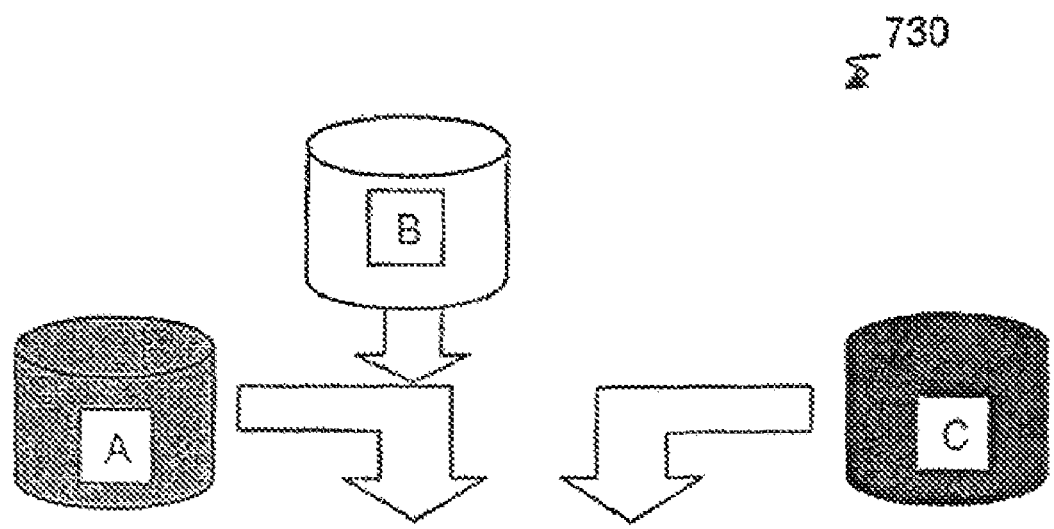
FIGS. 30A-30F schematically illustrate a method for forming and dispensing a vinyl polymer hydrogel in accordance with an alternate preferred embodiment of the present invention.
Figure 30B:
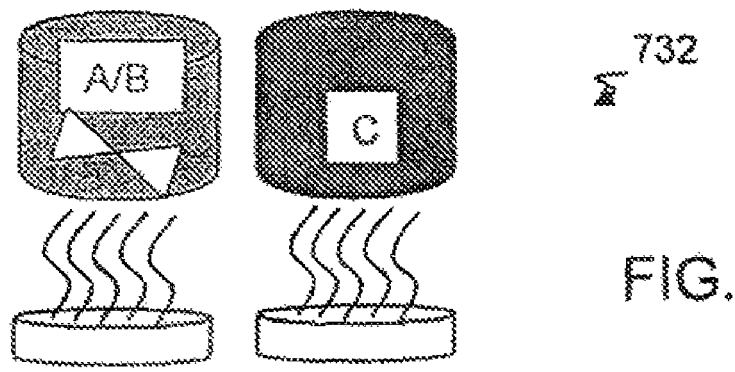
Figure 30C:
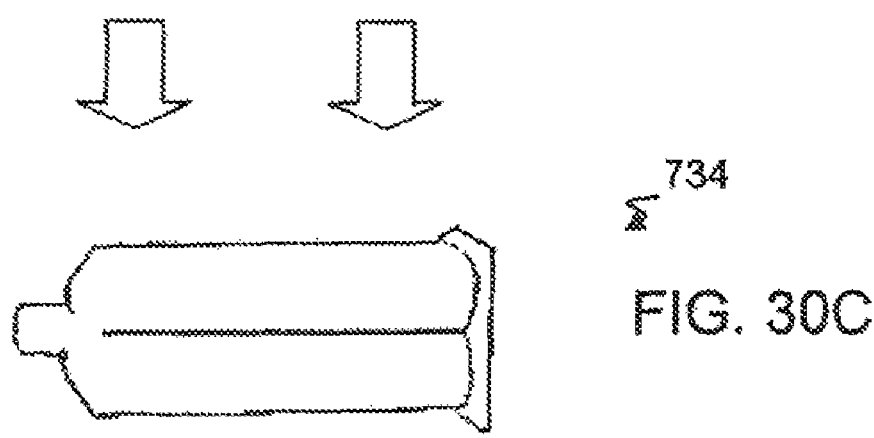
Figure 30D:
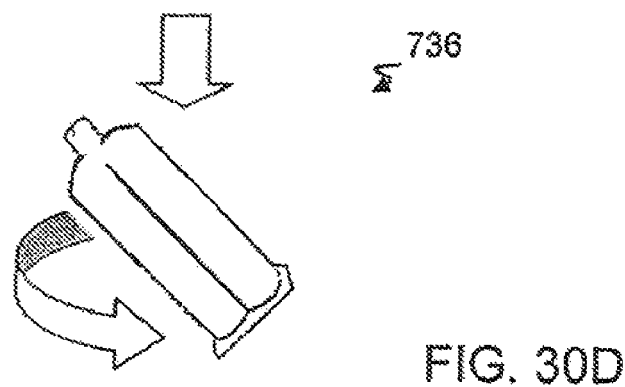
Figure 30E:
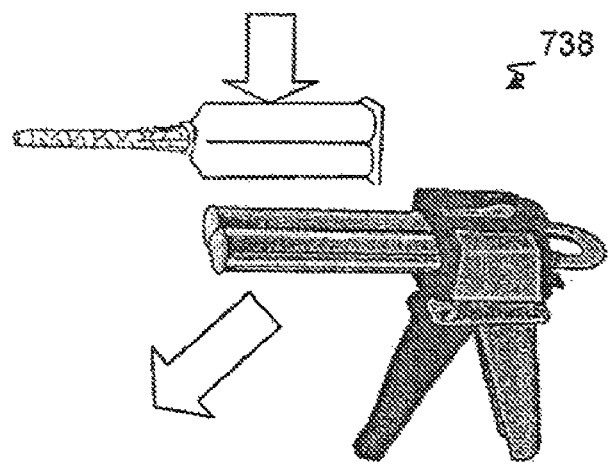
Figure 30F:
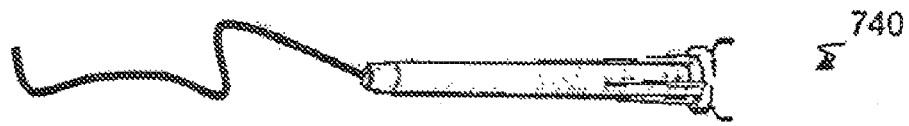

FIGS. 30A-30F schematically illustrate a method for forming and dispensing a vinyl polymer hydrogel in accordance with an alternate preferred embodiment of the present invention. As illustrated in FIG. 30A, the hydrogel system is supplied in three aseptic containers or two containers wherein the contents of containers A and B are combined. The aseptic cartridges contain PVA, solvent 1 and gellant, respectively. As illustrated in FIG. 30B, the PVA solution is mixed and heated and the gellant is also heated in container C. The ingredients are then loaded into separate chambers of a twin barrel system while maintaining the elevated temperature as shown in FIG. 30C. The barrel system is then centrifuged and/or vacuum degassed and injected through a static mixer nozzle. As shown in FIG. 30E, a nozzle or syringe needle is attached and assembled onto a plunger system that can be mechanically or electrically actuated (ratcheted) to deliver mix solution. The mixed solution flows for a short period of time before becoming unworkable.

Figures 31A, 31B, 31C, 31D, 31E:
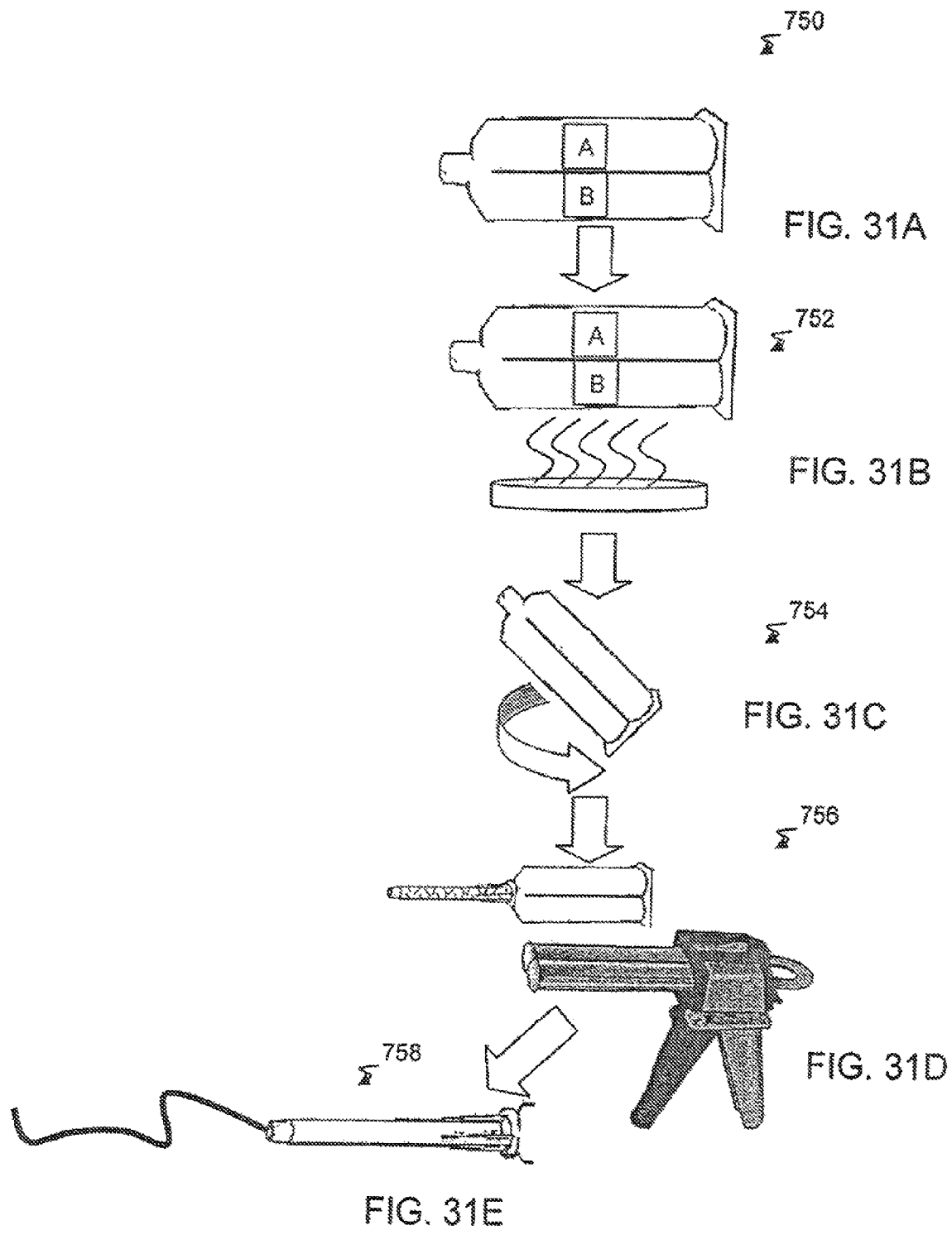
FIGS. 31A-31E schematically illustrate a method for forming and dispensing a vinyl polymer hydrogel in accordance with an alternate preferred embodiment of the present invention.

FIGS. 31A-31E schematically illustrate an alternative preferred method for forming and dispensing a vinyl polymer hydrogel in accordance with an embodiment of the present invention. This embodiment includes a hydrogel system being supplied in a single cartridge. The aseptic double barreled cartridge illustrated in FIG. 31A contains PVA and solvent 1 in one and gellant in the other. The cartridge is heated to remelt the PVA in solution as shown in FIG. 31B. The system is then centrifuged and/or vacuum degassed and injected through a static mixer nozzle as shown in FIG. 31C. As illustrated in FIG. 31D, the nozzle or syringe needle is attached and assembled onto a plunger system that can be mechanically or electrically actuated (ratcheted) to deliver the mixed solution. The mixed solution flows for a short period of time before becoming unworkable.

Figure 32:
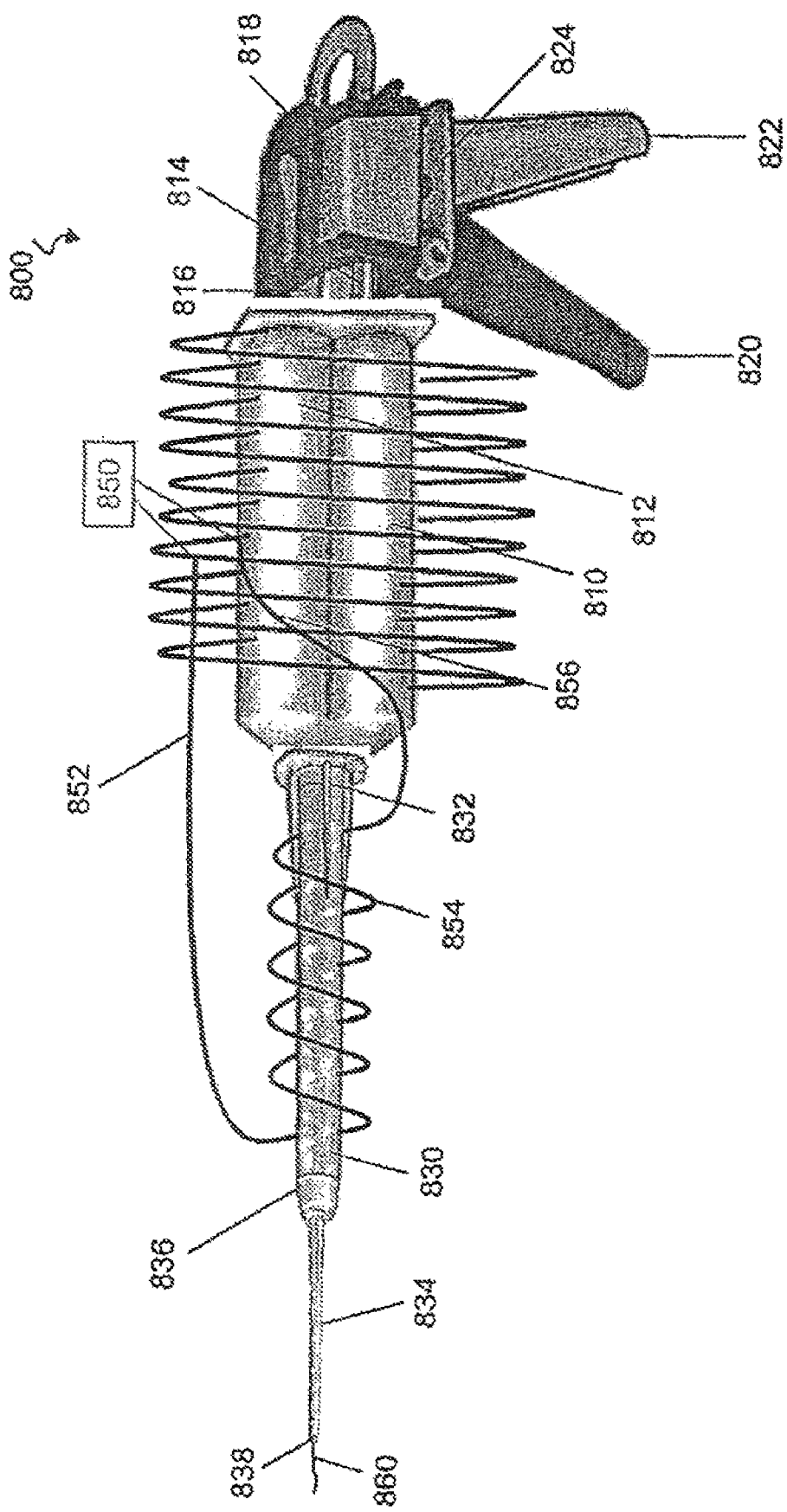
FIG. 32 schematically illustrates a dispenser for providing a vinyl polymer hydrogel in accordance with a preferred embodiment of the present invention.

FIG. 32 schematically illustrates a dispenser 800 for providing a vinyl polymer hydrogel in accordance with a preferred embodiment of the present invention. The dispenser includes a first chamber 810; a second chamber 812; a first chamber piston rod 814; a second chamber piston rod 816; a housing 818; a movable lever 820; a fixed handle 822; a mixing chamber 830; a mixing chamber fitting 832; a dispensing tube 834; a dispensing tube fitting 836; a dispensing tube opening 838; a temperature controller 850; a connector 852; a mixing chamber heater/cooler 854; a chamber heater/cooler 856; and a dispensed mixture 860 in preferred embodiments, vinyl polymer solution and gellant are provided as premixed sterile solutions, preferably pre-packaged in first chamber 810 and second chamber 812, respectively. A heater/cooler 854 and 856 can include resistive heating, inductive heating, water jacket or Peltier effect heating/cooling elements. The temperature controller 850 can be integral with the dispenser 800, or a separate unit, connected by connector 852. The entire dispenser 800 can be sterile, preloaded and intended for a single use.

In another preferred embodiment, drugs can be mixed with either the vinyl polymer solution or the gellant so that the resultant injected gel contains an encapsulated drug that can release over time.

In yet another preferred embodiment, a small amount of free radical scavenger is added to the vinyl polymer solution in a concentration of approximately 1 to 1000 parts per million. The free radical scavenger can be any common free radical scavenger known to those skilled in the art, but can include Vitamin E and hydroquinones. The purpose of the free radical scavenger is to minimize the effects of ionizing radiation, either gamma or electron beam (e-beam), which may be used to sterilize the material prior to use. Radiation can either crosslink or cause scissioning in PVA solutions depending on the concentration of the solution.

In another embodiment, the final mechanical properties of the hydrogel can be tailored by varying the initial starting concentration of the vinyl polymer solution, and the concentration of the gellant in the final mixture.

In another series of embodiments, the generation of conditions conducive to force the gelation of the PVA entail the internal release of active ingredients or sequestered materials which can comprise any combination of or, single gellant listed herein before. To change the theta-point of the solvent relative to the PVA, or to alter the co-nonsolvency of the solvent relative to PVA, there exist potential methods based on the sequestration of "active" molecular species. Such mechanisms serve to rapidly release the sequestered active molecular species to achieve local changes in solvency. If enough of the sequestering moieties are distributed through the system, it is possible to effect a global change in solvency. Such a method would serve to alleviate precipitation problems associated with mixing the PVA with a particularly active gellant. Suitable sequestration systems are available, including liposome sequestration, polymer sequestration, crystalline sequestration, gel encapsulation and degradable encapsulation In a preferred embodiment, liposome sequestration uses lipid vesicles to separate their contents from the external environment. This system has been used successfully to induce rapid gelation of polysaccharide and protein hydrogels. Lipid vesicles can be induced to release their contents by either thermal or phototriggering methods. In preferred embodiments, the gelation of a PVA solution prepared according to the present invention can be accelerated following application of a suitable trigger. A suitable trigger can be the gel/liposome composition heated to body temperature. In a preferred embodiment of the present invention, an aqueous PVA solution is mixed with a suspension of thermally triggerable liposomes containing a concentrated NaCl solution or solid NaCl at a temperature below that necessary to induce release of the NaCl. Upon injection into a region of interest such as a body cavity at or near 37° C., the liposomes release the contained NaCl, changing the Flory parameter of the solution and causing gelation of the PVA. In other embodiments, other suitable gellants can be sequestered in the lipid vesicles to influence the gelation rate of PVA.

In another preferred embodiment, the sequestration system is based on the increase of colligative activity of a polymer by cleavage of the polymer into multiple smaller fragments. In some complex polymer systems, degradation produces fragments that are more soluble than the original molecule, for example, collagen. Such an increase in smaller, more active components shifts the solvency of the overall solution to induce the gelation of PVA. Some examples of suitable polymeric sequestration systems (and their enzymatic cleaving complements) are listed, without limitation, in the table below. The table is not inclusive however the polymer sequestration concepts are intended to include all polymers, in particular, biocompatible polymers or biopolymers, and their particular polymer degradation mechanisms. In a further embodiment, the two above approaches can be combined, using triggered liposomes to sequester the appropriate enzymes to produce triggerable cleavage of the gellant.

In one embodiment, fully formed purified type I collagen fibrils can be mixed with PVA solution at temperatures below the denaturation temperature of the collagen. The solution can be heated to induce the denaturation of the collagen fibrils which would release soluble gelatin molecules into the PVA, changing the relative solubility of the PVA and potentially inducing PVA gelation.

TABLE 2

Specific Cleavage Methods for Selected Gellants

| Polymer | Degradation mechanism | Degradation specifics Or enzyme complement |
| --- | --- | --- |
| Collegen Type I | Heat denaturation | Temperature 40-90° C. |
| Collegen Type I | Enzyme cleavage | Collagenase (MMP I) |
| All remaining collagens | Heat denaturation | Temperature 40-90° C. |
| All remaining collagens | Enzyme cleavage | All MMP complements (MMPs 3-20) |
| Hyaluronic Acid | Enzyme cleavage | Testicular Hyaluronidase Hyaluron lyase |
| Chondroitin Sulfate | Enzyme cleavage | Chondroitinase family |
| Heparin | Enzyme cleavage | Heparinase I/III |
| All remaining glycosaminoglycans | Enzyme cleavage | GAG enzyme complements |
| Aggrecan | Enzyme cleavage | Agrecanase |
| All remaining Progeoglycans | Enzyme cleavage | PG enzyme complements |

In another preferred embodiment, the sequestration method entails the confinement of active moieties in crystals that can be melted irreversibly, producing a large change in the activity of the crystalline component. In one referred embodiment the crystalline component is a starch, comprising amylase molecules, amylopectin molecules or mixtures thereof that are linear and branched multimers of glucose. Starch particles normally comprise crystalline and amorphous regions. Upon heating in solution, starch particles absorb water readily and, upon gelatinization, the starch particles become highly osmotically active. When returning to room temperature, starches gelatinize, but not recrystallize. Thus, PVA can be mixed effectively with crystalline starch granules to make a solution where the PVA is soluble. However, upon heating above the gelatinization point of the starch and recooling, the PVA would be forced to gel because of the competition for solvent with the gelatinized starch which is more hygroscopic.

In another embodiment, the sequestration method involves the use of gel-based capsules, which upon a suitable trigger (for example, without limitation, pH, ionic concentration, temperature, radiation) release their encapsulated contents. In a further embodiment, the sequestration method involves the trapping of the active molecules in a degradable matrix. In preferred embodiments, a suitable biodegradable polymer can be selected from the group including, but not limited to, a poly(L-lactide), a poly(D,L-lactide), a poly(lactide-co-glycolide), a poly(ϵ-caprolactone), a polyanhydride, a poly(beta-hydroxy butyrate), a poly(ortho ester) and a polyphosphazene.

In general, a suitable gellant in accordance with the preferred embodiments is a solute that is water soluble, has a higher affinity for water than PVA. In preferred embodiments, a solid gellant or an aqueous solution of gellant is added to an aqueous PVA solution. Typically PVA solutions in the range of from about 1 weight % to about 50 weight % PVA are prepared by adding the desired amount of PVA to warm deionized water while mixing. For example, a 20% PVA solution by weight is prepared by dissolving 20 g of PVA (100 kg/mole; 99.3+% hydrolyzed; JT Baker) in 80 g of deionized water heated in a water bath to a temperature of greater than 90 degrees Celsius with continuous stirring for a minimum of 15 minutes using a vortex mixer (VWR BRAND). The PVA solution obtained was substantially clear when fully dissolved and melted. The solution was placed in a covered container to avoid evaporation, optionally under a mineral oil protective layer.

Figure 22A:
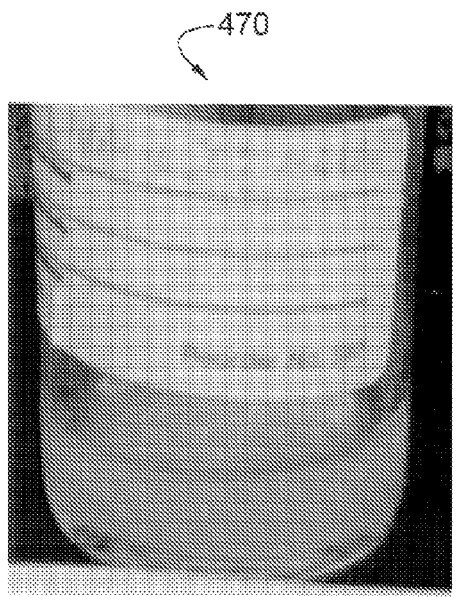
FIGS. 22A-22D illustrate a PVA hydrogel prepared by adding 1.4 g of 400 molecular weight poly(ethylene glycol) (PEG 400, Sigma Aldrich) to 6 g of an aqueous 10 wt % PVA solution while mixing, in accordance with a preferred embodiment of the present invention, showing the product at four time durations after the end of mixing.
Figure 22B:
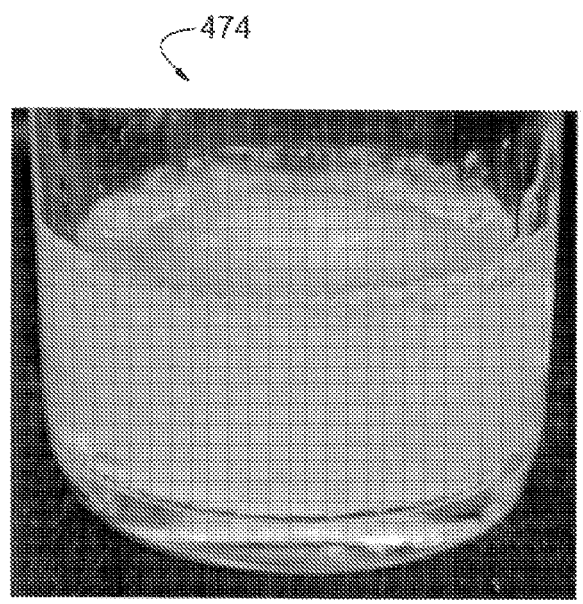
Figure 22C:
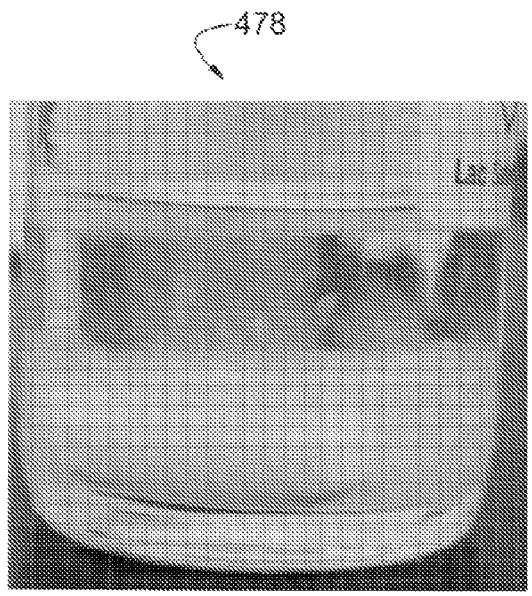
Figure 22D:
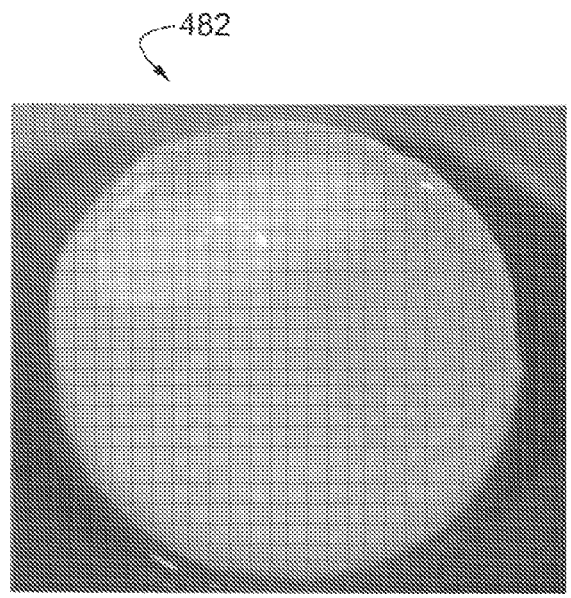

In one preferred embodiment, 1.4 g of 400 molecular weight poly(ethylene glycol) (PEG400, Sigma Aldrich) was added gradually to 6.0 g of 10% by weight PVA solution was stirred while stirring on a hot plate at 50 degrees Celsius and then the jar was shaken. After initially producing an inhomogeneous solution whilst adding the material became homogeneous and rapidly opaque. The final get was (by weight) 8% PVA, 19% PEG 400 and 73% water. FIGS. 22A-22D show the product at four time durations after the end of mixing; FIG. 22A, zero minutes; FIG. 22B, 15 minutes; FIG. 22C, 2 hours, under a mineral oil protective layer; and FIG. 22D, one day, out of the jar.

Figure 1B:
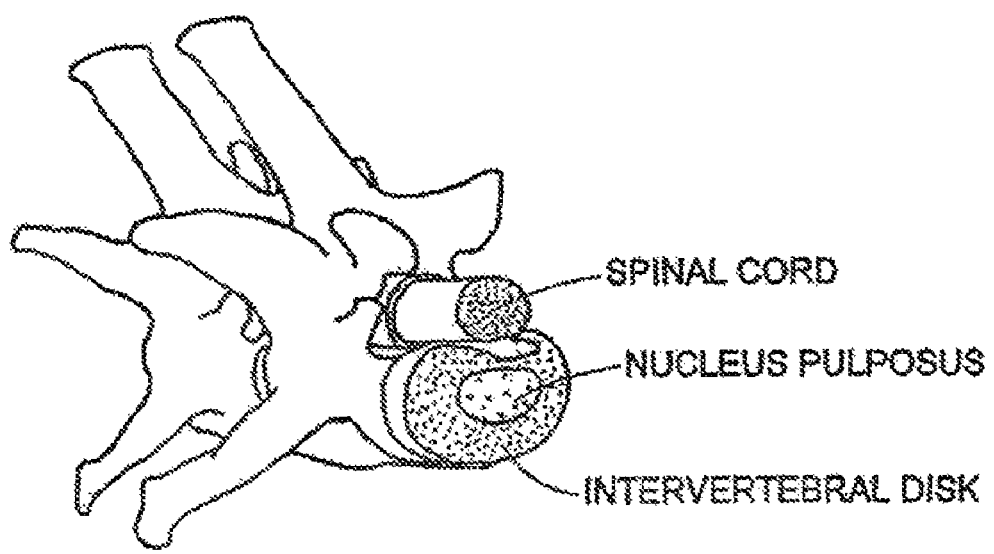
Figure 23A:
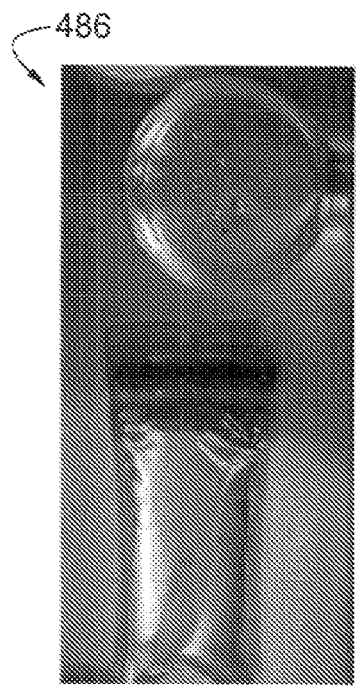
FIGS. 23A-23E illustrate a PVA hydrogel prepared by adding 35.6 g of aqueous 10 wt % PVA solution to 18.7 g of aqueous 5.1 M NaCl while mixing, and the resulting mixture aggressively shaken, in accordance with a preferred embodiment of the present invention, showing the product at five time durations after pouring into a covered dish and a flexible bag.
Figure 23B:
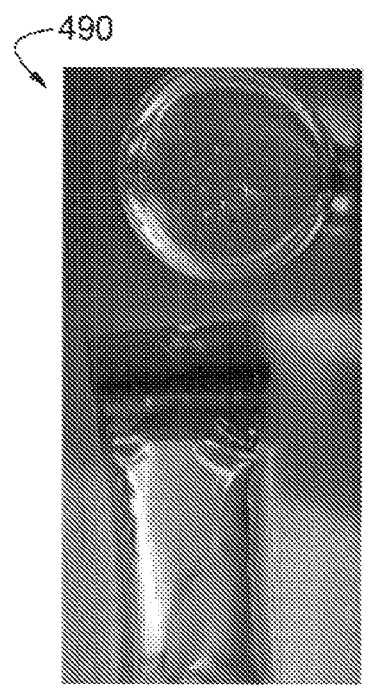
Figure 23C:
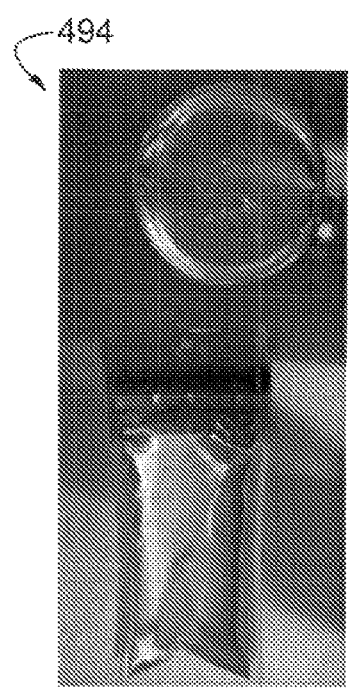
Figure 23D:
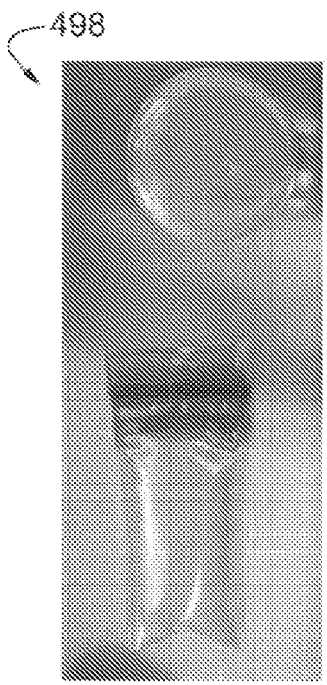
Figure 23E:
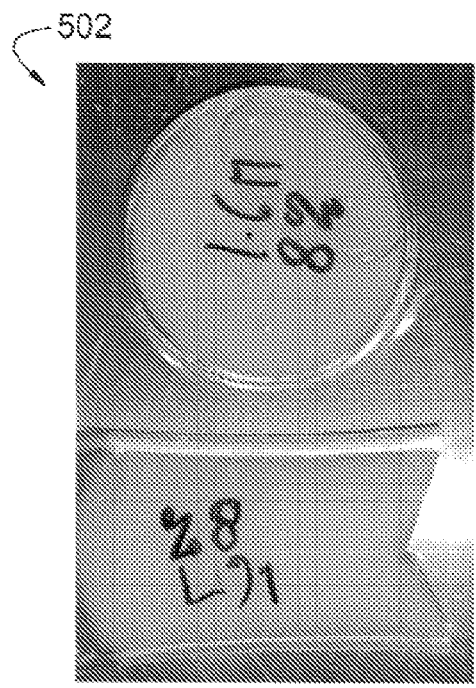

In one preferred embodiment, a PVA hydrogel was prepared by adding 35.6 g of aqueous 10 wt % PVA solution to 18.7 g of aqueous 5.1 M NaCl while mixing, and the resulting mixture aggressively shaken. The solution was briefly inhomogeneous before becoming smooth and transparent. Over the period of 16 hours the solution became gradually more opaque and gelled. The final gel was 7 wt % PVA, 8 wt % NaCl and 85 wt % water. FIGS. 23A-23E illustrate the PVA hydrogel prepared, showing the product at five time durations after pouring into a covered dish and a flexible bag. FIG. 23A, zero minutes; FIG. 23B, 20 minutes; FIG. 23C, 1 hour; FIG. 23D, 2 hours; and FIG. 23E, 17 hours. Note that the solution was fluid for long enough that a circular shape was easily formed. The solution was also cast in a flexible bag to demonstrate its abilities for space filling applications in deformable environments.

In another embodiment, an aqueous 10 wt % PVA solution was placed in the larger barrel of a 4:1 ratio epoxy adhesive gun (3M). Poly(ethylene) glycol with a molecular weight of 400 g/mol was placed in the smaller barrel. The resulting blend was delivered through a 3 inch static mixing nozzle (3M) into a mold held at room temperature. The resulting mix had 8 wt % PVA, 20 wt % PEG 400 and 72 wt % water. The resulting mixture was observed to gel inhomogeneously on delivery, but with time resulted in a homogeneous opaque gel.

Figure 24A:
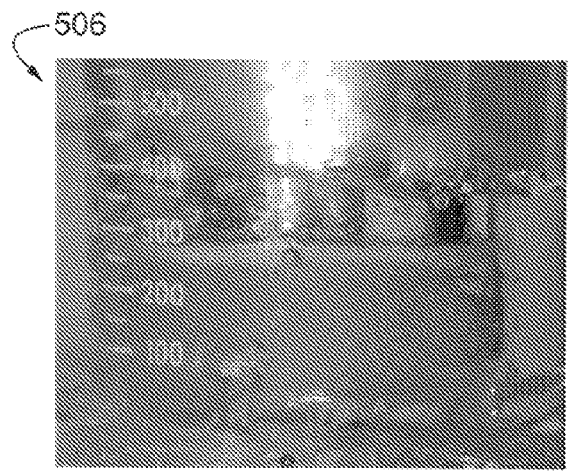
FIGS. 24A-24F illustrate a PVA hydrogel prepared by adding NaCl to aqueous 10 wt % PVA solution at about 95 degrees Celsius (FIG. 24A) while mixing to make a final concentration of 2M NaCl (FIG. 24B), in accordance with a preferred embodiment of the present invention. After mixing for 15 minutes, aliquots of the resulting mixture were poured into two containers that were cooled at room temperature (FIG. 24C, 15 minutes.
Figure 24B:
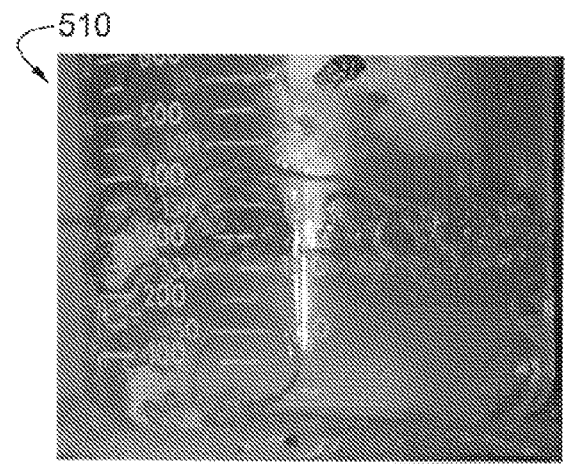
Figure 24C:
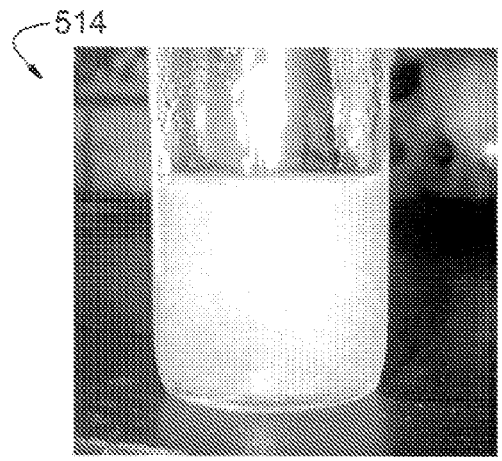
Figure 24D:
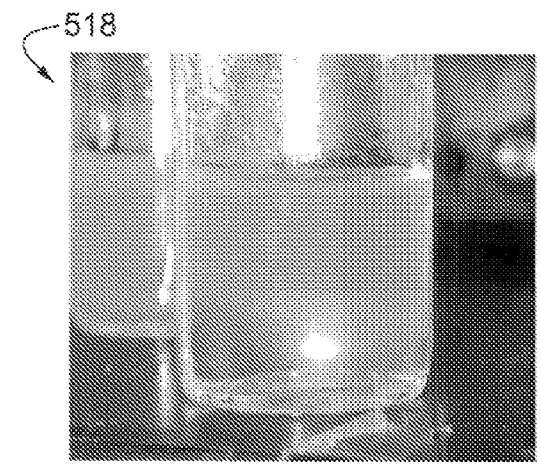
Figure 24E:
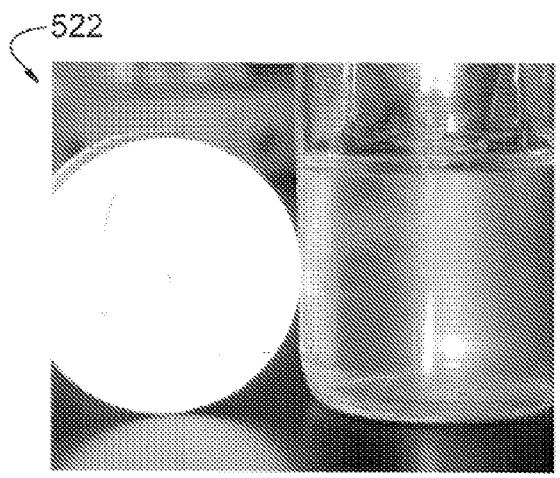
Figure 24F:
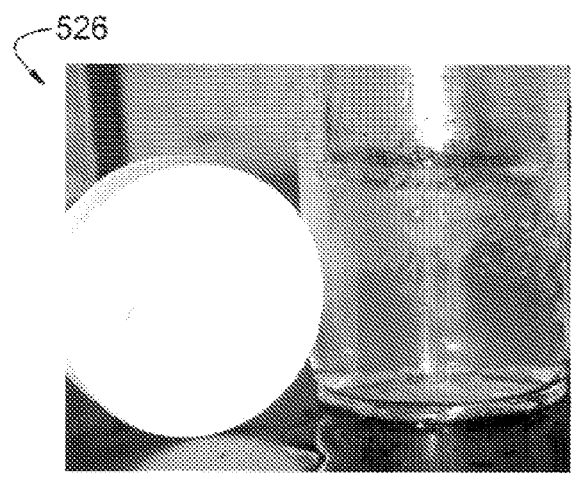

In a further preferred embodiment, a PVA hydrogel was prepared by adding NaCl to an aqueous 10 wt % PVA solution at about 95 degrees Celsius (FIG. 24A) while mixing to make a final concentration of 2M NaCl. After approximately 15 minutes, the resulting solution was smooth and homogeneous (FIG. 24B). The PVA solution obtained was poured into two jars, one of which was equilibrated at room temperature (FIG. 24C, 15 minutes; FIG. 24E, one hour), the other of which was placed on shaved ice (FIG. 24D, 15 minutes; FIG. 24F, one hour). The solution was initially cloudy, but homogeneous. After 1 hour, the gel cooled at room temperature was slightly cloudy, whereas the ice-cooled gel was predominantly transparent.

The two samples were then stored at room temperature. The final resulting gels after one month exhibited significant syneresis and visually looked identical, but the rapidly cooled material appeared to turn opaque much faster.

Figure 25A:
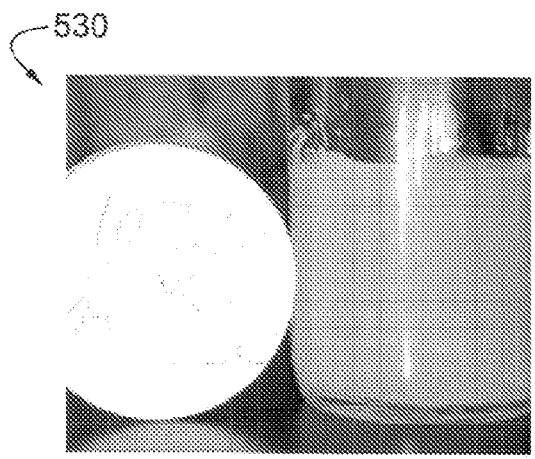
FIGS. 25A-25F illustrate the PVA hydrogels of FIGS. 24A-24F after storage.
Figure 25B:
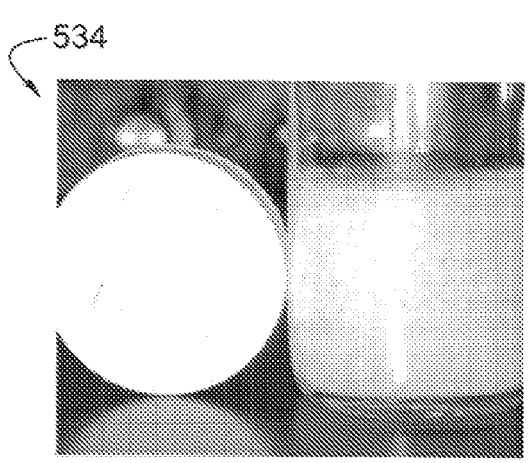
Figure 25C:
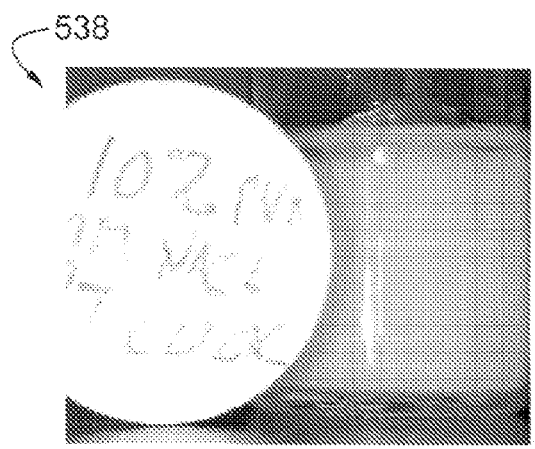
Figure 25D:
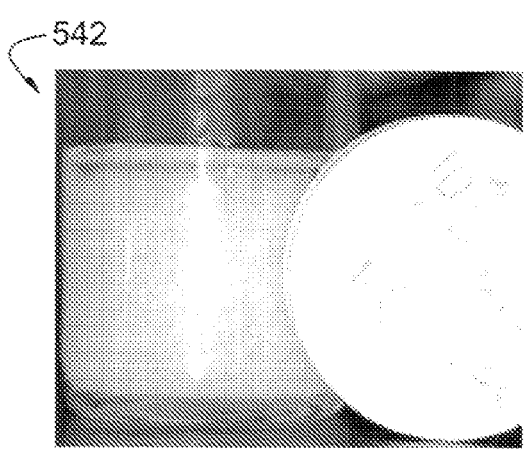
Figure 25E:
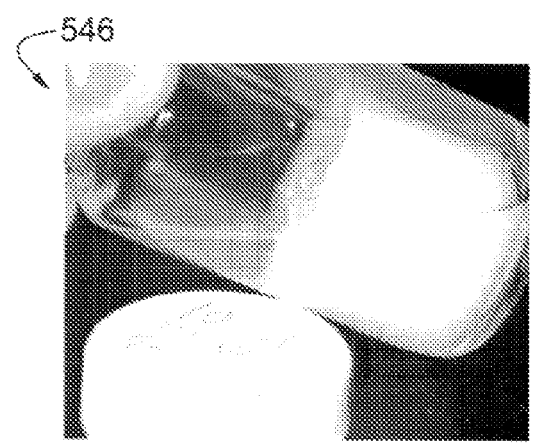
Figure 25F:
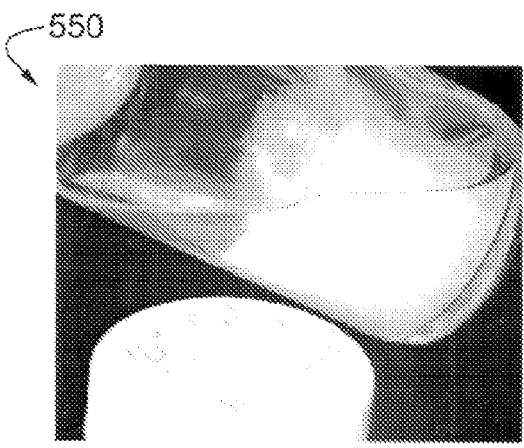

FIGS. 25A-25F illustrate the PVA hydrogels of FIGS. 24A-24F after storage. FIG. 25A, cooled one hour at room temperature and stored 12 hours at room temperature; FIG. 25B, cooled one hour on ice and stored 12 hours at room temperature; FIG. 25C, cooled one hour at room temperature and stored one month at room temperature; FIG. 25D, cooled one hour on ice and stored one month at room temperature; FIG. 25E, the PVA gel of FIG. 25C, oriented to show water released due to syneresis; and FIG. 25F, the PVA gel of FIG. 25D, oriented to show water released due to syneresis.

Figure 26A:
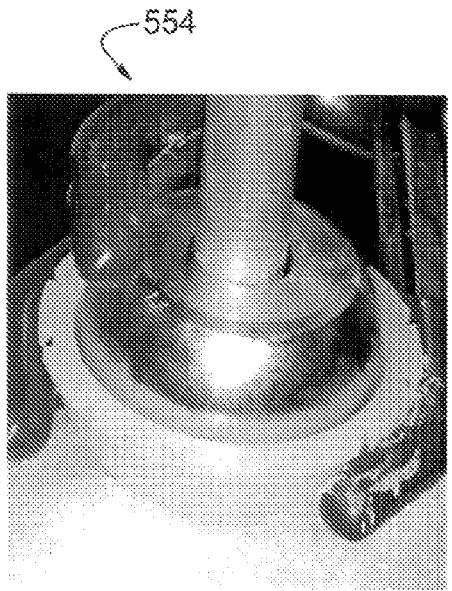
Figure 26B:
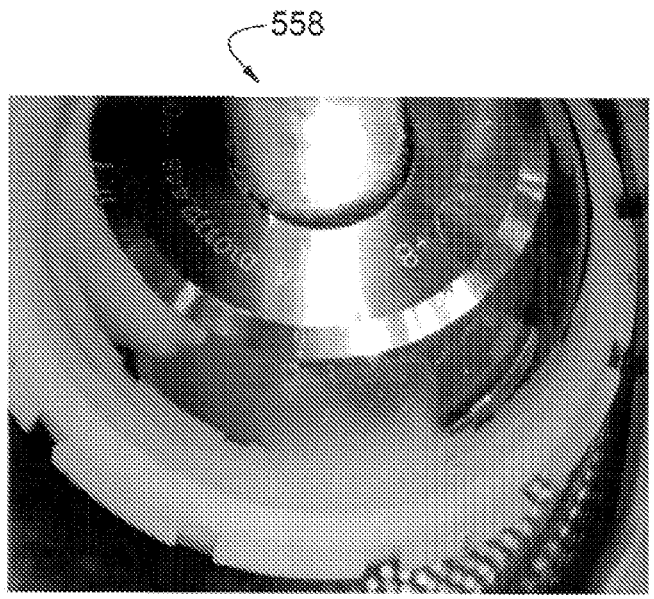

In preferred embodiments, the present invention provides a method for early treatment of joint disease by providing a polymer cushion formed in situ between load-bearing surfaces in the joint. In one preferred embodiment, a PVA cushion is formed in situ within the hip joint by dislocating the head of the femur, filling the exposed cavity within the joint with a fluid solution of PVA and gellant, replacing the head of the femur and allowing the PVA solution to gel in situ. In an example, illustrated in FIGS. 26A-26D, dry NaCl was added at a moderate rate to a 20 wt % aqueous PVA solution warmed in a water bath at about 95 degrees Celsius with continuous stirring to make a 2.1 M NaCl solution. After 1 minute the resulting solution was smooth and malleable, resembling taffy. Resulting solution was removed from the mixer and placed in a chilled polyethylene liner from a Total Hip Replacement (THR) system. The matching cobalt-chrome ball from the THR joint inserted into the liner socket and allowed to stand for 1 hour at room temperature. The mold was then placed in deionized water for a further 1 hour, whereupon the ball was removed from the poly(ethylene) liner. At this point a thin, homogeneous and substantially blemish-free hemisphere of PVA was obtained. FIG. 26A shows the mold formed by the chilled polyethylene liner and the matching ball from a total hip replacement joint. FIG. 26B shows the mold after filling the chilled polyethylene liner with the PVA solution and putting the matching ball in place.

Figure 26C:
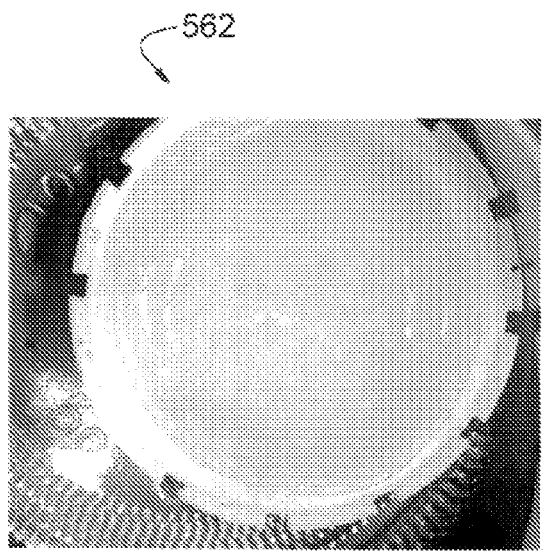
Figure 26D:
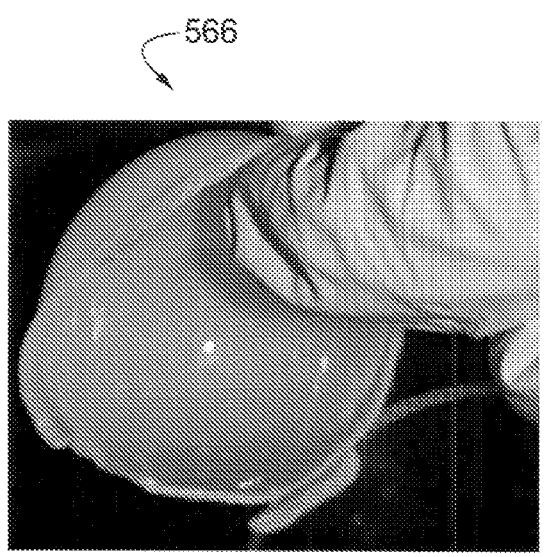

FIG. 26C shows the molded PVA in the polyethylene liner after one hour in air at room temperature followed by one hour in deionized water at room temperature. FIG. 26D shows the molded PVA product removed from the polyethylene liner.

Figure 27A:
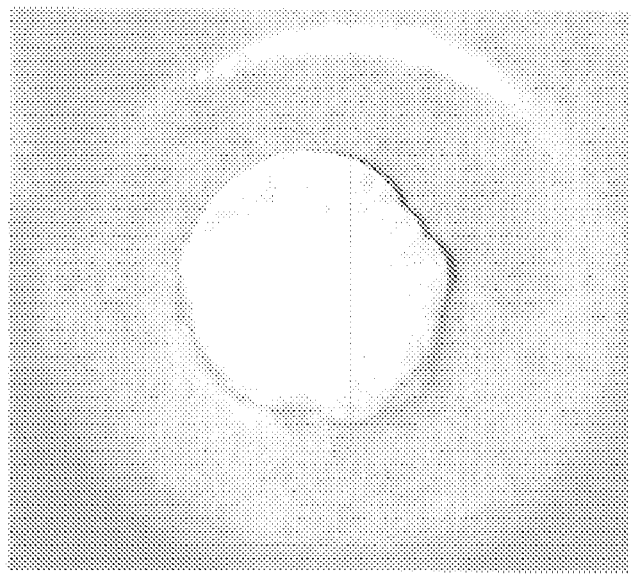
FIGS. 27A-27B illustrate PVA hydrogels incorporating chondroitin sulfate (CS) prepared in accordance with preferred embodiments of the present invention, where
Figure 27B:
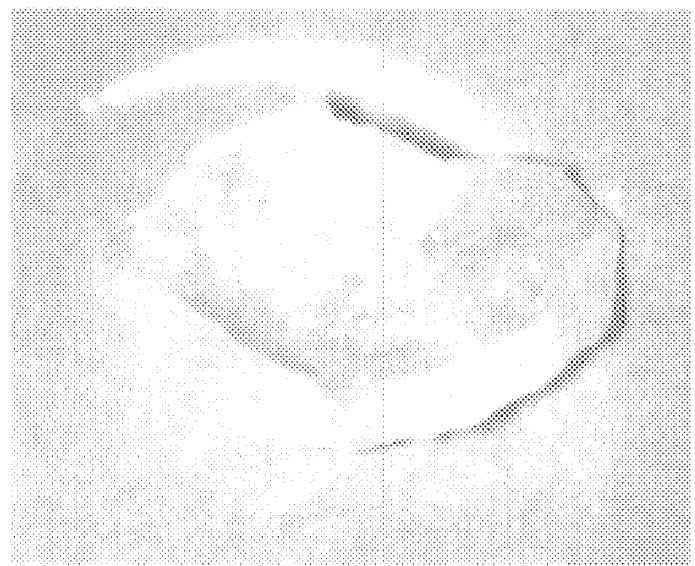

Since the mechanism of gelation is chemically non-specific, it is possible to use virtually any solute that has sufficient osmotic activity to force PVA self-association. In a further preferred embodiment, the co-nonsolvency was exploited by using a naturally-occurring biocompatible material as a gellant to form a PVA gel. Chondroitin sulfate (CS, Now Foods Bloomingdale, Ind.) was used to induce the gelation of polyvinyl alcohol. Aqueous 10 wt % PVA solution was prepared and stored at 60° C. until use. In a first example, warm chondroitin sulfate solution (~80° C.) was added to the warm PVA solution to generate a 5 wt % PVA, 7 wt % CS mixture. Upon cooling to room temperature, the mixture formed a weak gel over a period of two days that remained stable (FIG. 27A). In the second example 600 mg CS was added directly with continuous stirring to 10 ml of 10 wt % PVA solution at 60 degrees Celsius. Compared to the previous example, the mixture formed a much stiffer gel within minutes and remained stable (FIG. 27B). The success of inducing the gelation of PVA using a biocompatible material that is typically present in the joint space suggests the possibility of in situ joint repair or augmentation.

In a further example, serine, a common amino acid in the blood stream of humans was dissolved in deionized water to produce a 30 wt % aqueous solution. The PVA solution and serine solution were then combined in equal parts by volume at less than 90 degrees Celsius and mixed thoroughly, resulting in a solution of 10% PVA, 15% serine and 75% water. The solution stayed fluid while at the higher temperature but as it cooled it gradually gelled, producing a gel after about 1 hour.

In a preferred embodiment, the vinyl polymer solution may include, without limitation, mixtures of vinyl polymers such as polyvinyl alcohol and polyvinyl pyrollidone (PVP) or copolymers of PVP, as described in the European Patent specification EP 1229 873 B1, the entire teachings of which are incorporated herein by reference.

In a preferred embodiment, the vinyl polymer solution may include any mixture of components that form physical associations through manipulation of relative solvent quality.

In a preferred embodiment, the vinyl polymer solution may include a nano or microstructuring agent which can include nano and microparticulates such as clay or silica, charged or uncharged, and/or nanostructuring functionalized molecules such as POSS as described herein before. These nano or microparticulates provide nucleation sites that accelerate or augment the gelation process. Preferred embodiments of the present invention benefit from this recognition that nucleation sites provided by any particles of the appropriate size in the vinyl polymer solution augment gelation to result in a gel of the desired mechanical properties.

Repair of Damaged Intervertebral Disks

Figure 33:
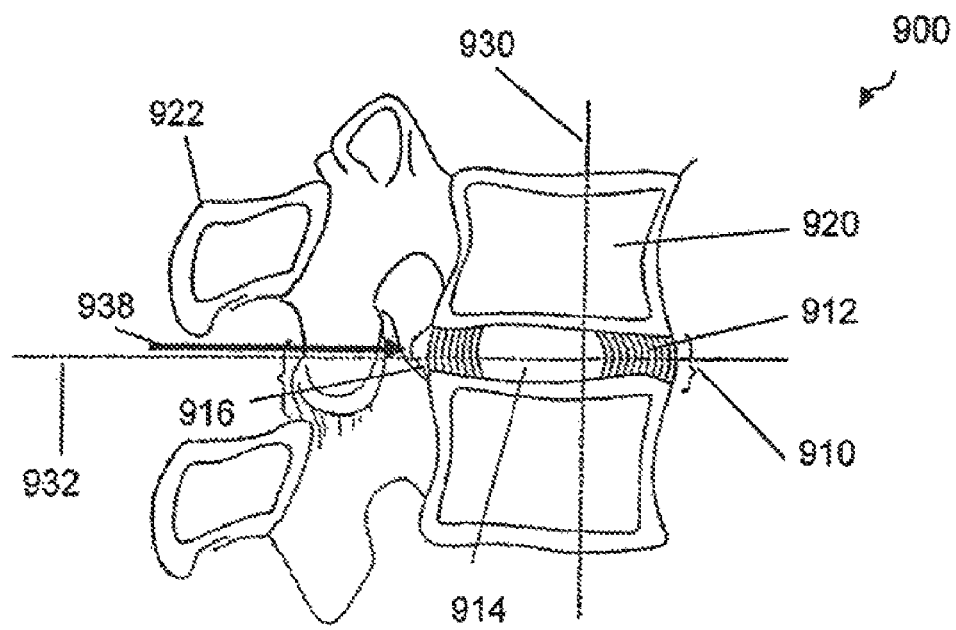
FIG. 33 illustrates a midsagittal cross-section of a portion of a functional spine unit in which two vertebrae and the intervertebral disk are visible.
Figure 34:
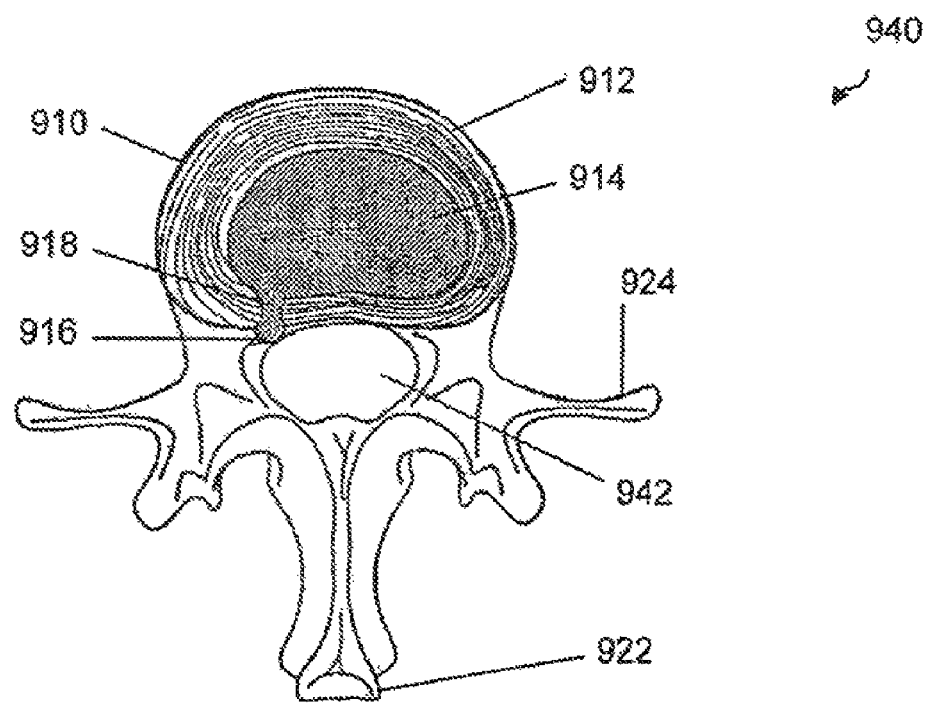
FIG. 34 illustrates a transverse section through a damaged intervertebral disk, showing a spinous process and transverse process of an adjacent vertebra, annulus fibrosis and, nucleus pulposus.

In preferred embodiments, the method and dispenser of the present invention are used in the repair of a damaged intervertebral disk. FIG. 33 is a schematic illustration of a midsagittal cross-section 900 through two vertebrae, each vertebra having vertebral body 920 and spinous process 922; the two vertebral bodies enclosing an intervertebral disk 910 comprising annulus fibrosis 912, nucleus pulposus 914 and herniation 916; provided for orientation are vertical axis 930, anterior-posterior axis 932 and arrow 938 indicating posterior access path to the herniation 916. FIG. 34 is a schematic illustration of a transverse section 940 through a damaged intervertebral disk 910, showing spinous process 922 and transverse process 924 of an adjacent vertebra, annulus fibrosis 912, nucleus pulposus 914, the outline of the spinal cord 942 and herniation 916 protruding through defect 918.

Briefly, the damaged intervertebral disk is repaired by respecting the herniated region, injecting a viscoelastic solution of the vinyl polymer hydrogel of the present invention to replace part or substantially all of the nucleolus pulposus material, controlling the rate of gelation of the vinyl polymer hydrogel by methods described herein before, and closing the injection site. The viscoelastic solution of the vinyl polymer hydrogel can be injected through a defect in the annulus fibrosus at the site of the herniation, and/or through another point of the annulus fibrosus. The injection site and the defect can be closed by modifying the local physical properties of the hydrogel by a further application of gellant in situ, as described herein before. Alternatively, the injection site and the defect can be sealed and reinforced by the use of known medical devices to seal, reinforce or close the injection site or other defect of the body cavity. Suitable such devices are disclosed in published International Patent Applications WO 01/12107 and WO 02/054978, which are hereby incorporated by reference in their entirety.

Figure 35:
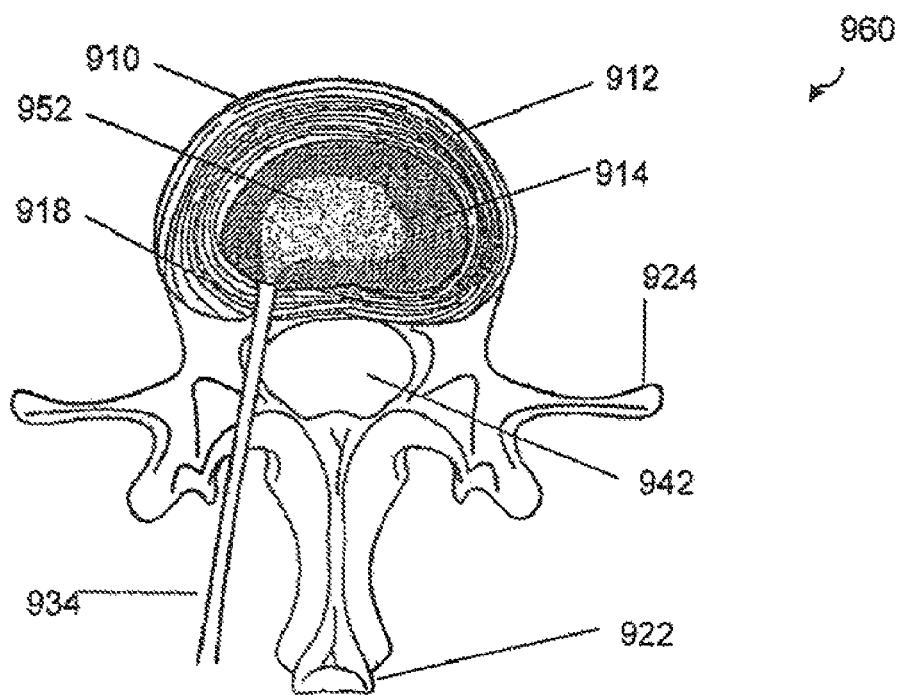
FIG. 35 illustrates a step of dispensing a mixture of gellant and vinyl polymer in a method for repairing a damaged intervertebral disk in accordance with a preferred embodiment of the present invention.

FIG. 35 is an illustration of a step in a method for the repair of a damaged intervertebral disk 910 in accordance with a preferred embodiment of the present invention, showing in transverse section 960 a spinous process 922 and a transverse process 924 of an adjacent vertebra, annulus fibrosis 912, nucleus pulposus 914, the outline of the spinal cord 942 and dispensing tube 934 introduced through defect 918, dispensing the viscoelastic mixture of gellant and vinyl polymer 952. In preferred embodiments, the local physical properties of the hydrogel are adjusted by an addition of a gellant through the same dispensing tube 934 following the dispensing of the desired amount of viscoelastic mixture of gellant and vinyl polymer. The additional gellant can be the same or different from the gellant initially mixed with the vinyl polymer solution.

Figure 36:
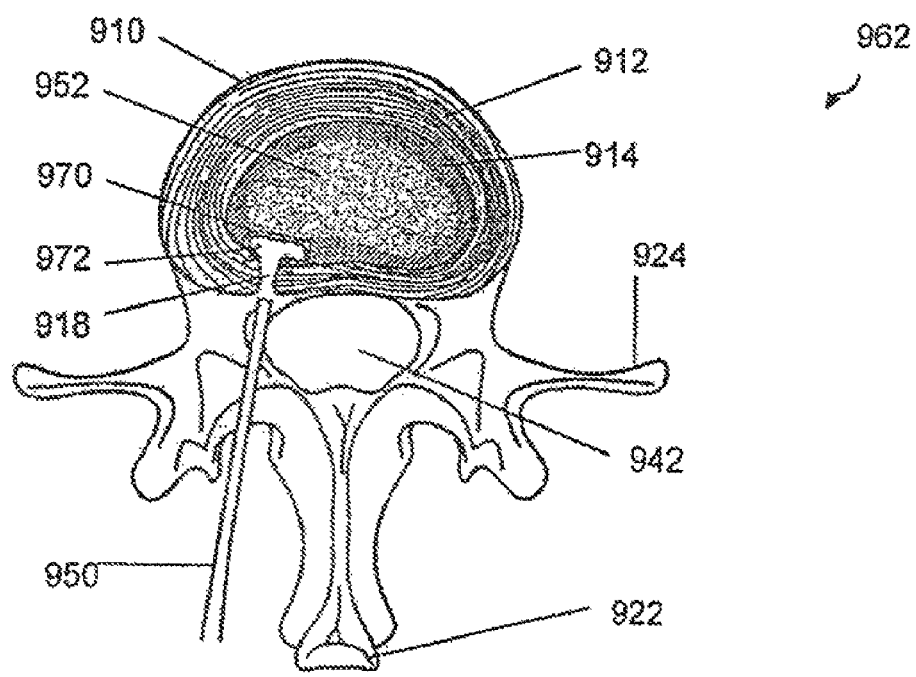
FIG. 36 illustrates a step in a method for repairing a damaged intervertebral disk in accordance with a preferred embodiment of the present invention showing, in particular, a mixture of gellant and vinyl polymer, a sealant, a fixative, and the fixative delivery instrument.

In alternative embodiments, a sealer can be used to supplement or instead of modifying the local physical properties of the hydrogel by an addition of a gellant. FIG. 36 is a schematic illustration of a step in the repair in accordance with a preferred embodiment of the present invention of a damaged intervertebral disk 910, showing in transverse section 962 a spinous process 922 and a transverse process 924 of an adjacent vertebra, annulus fibrosis 912, nucleus pulposus 914, the outline of the spinal cord 942, defect 918, mixture of gellant and vinyl polymer 952, sealant 970, fixative 918, a fixative delivery instrument 950. The sealant 970 is constructed from a material and is formed in such a manner as to resist the passage of fluids and other materials around the sealant 970 and through the defect 918. The sealant 970 can be constructed from one or any number of a variety of materials including, but not limited to, polytetrafluoroethylene (PTFE), expanded polytetrafluoroethylene (e-PTFE), NYLON™, MARLEX™, high density polyethylene, and/or collagen. See WO 02/054978, incorporated herein by reference. After placement of the sealant 970, fixative 918, such as sutures or soft tissue anchors, are placed using fixative delivery instrument 950.

Figure 37:
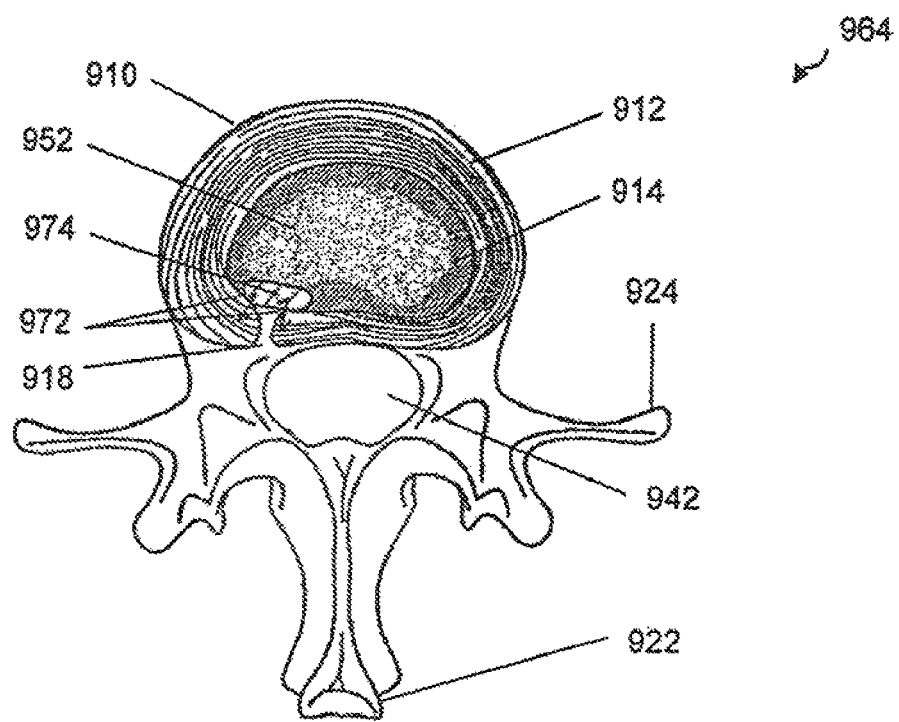
FIG. 37 illustrates a step in a method for repairing a damaged intervertebral disk in accordance with a preferred embodiment of the present invention showing, in particular, a mixture of gellant and vinyl polymer, barrier, a fixative, and a fixative delivery instrument.

In alternative embodiments, a barrier can be used. FIG. 37 is a schematic illustration of a stop in the repair in accordance with a preferred embodiment of the present invention of a damaged intervertebral disk 910, showing in transverse section 964 a spinous process 922 and a transverse process 924 of an adjacent vertebra, annulus fibrosis 912, nucleus pulposus 914, the outline of the spinal cord 942, defect 918, mixture of gellant and vinyl polymer 952, barrier 974, fixative 972, and fixation delivery instrument 950. The barrier 974 is preferably flexible in nature, and can be constructed from a woven material such as DACRON™ or NYLON™, a synthetic polyamide, polyester, polyethylene, and may be an expanded material such as e-PTFE. Alternatively, the barrier 974 can be a biologic material such as collagen. The barrier 974 can be expandable such as, for example, a balloon or a hydrophilic material. See WO 02/054978.

Figure 38:
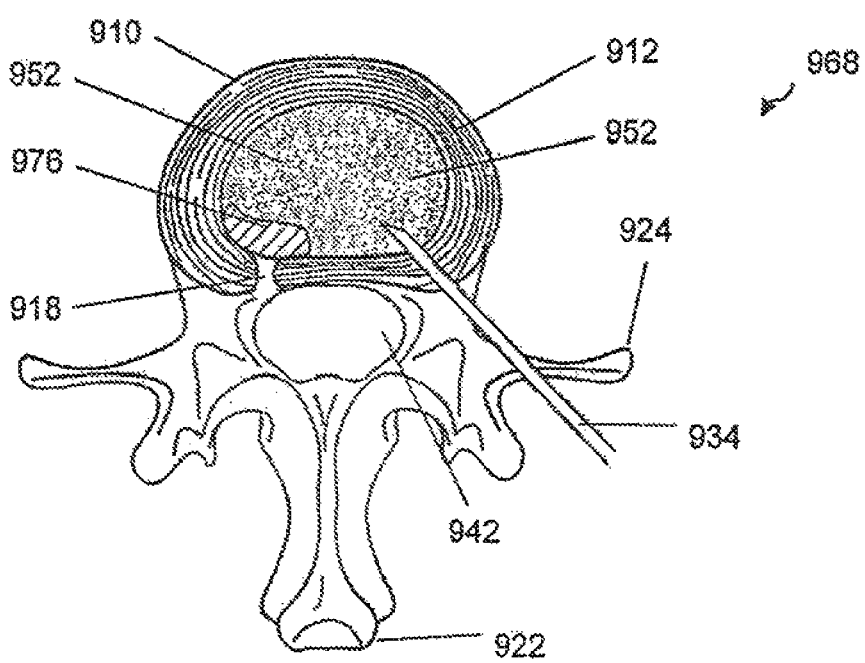
FIG. 38 illustrates a step in a method for repairing a damaged intervertebral disk in accordance with a preferred embodiment of the present invention showing, in particular, the mixture of gellant and vinyl polymer substantially filling the space previously occupied by the nucleus pulposus, a barrier, and a dispensing tube.

If appropriate the viscoelastic solution of the present invention is introduced at a site other than the defect. FIG. 38 is a schematic illustration of a step in the repair in accordance with a preferred embodiment of the present invention of a damaged intervertebral disk 910, showing in transverse section 968 a spinous process 922 and a transverse process 924 of an adjacent vertebra, annulus fibrosis 912, the outline of the spinal cord 942, defect 918, mixture of gellant and vinyl polymer 952 substantially filling the space previously occupied by the nucleus pulposus, barrier 976, and dispensing tube 934.

The claims should not be read as limited to the described order or elements unless stated to that effect. Therefore, all embodiments that come within the scope and spirit of the following claims and equivalents thereto are claimed as the invention.

We claim:

1. A kit for providing a vinyl polymer hydrogel to a region of interest via injection of an injectable thetagel solution, wherein the kit comprises:
    (A) a delivery device comprising
        (i) a first chamber that can contain a first solution comprising polyvinyl alcohol (PVA), wherein the first solution has a Flory interaction parameter (chi value) that is not sufficient for gelation, and
        (ii) a second chamber that can contain a second solution to be combined with the first solution, wherein combining the first and second solutions will result in an injectable thetagel solution that has a Flory interaction parameter (chi value) that is sufficient for gelation;
    (B) the first solution;
    (C) PVA; and
    (D) the second solution, wherein the delivery device when filled with the first solution and the second solution provides after injection of the injectable thetagel solution using the delivery device, a polymer hydrogel forms that has physical crosslinks between PVA molecules, wherein the polymer hydrogel is formed without chemical crosslinkers, irradiation or thermal cycling, and wherein the polymer hydrogel can fill the region.

2. The kit according to claim 1, wherein the first solution comprises one or more selected from the group consisting of deionized water, and dimethylsulfoxide.

3. The kit according to claim 1, wherein the second solution comprises one or more selected from the group consisting of salts, alcohols, polyols, amino acids, sugars, proteins, and polysaccharides.

4. The kit according to claim 1, wherein the hydrogel is anisotropic in one or more properties.

5. The kit of claim 1, wherein the injectable thetagel solution comprises about 1.0 to about 50.0 weight percent polyvinyl alcohol.

6. The kit of claim 1, wherein after the mixing the Flory interaction parameter is 0.25 to 1.0.

7. The kit of claim 1, wherein the PVA solution contains one or more non-gelling components.

8. The kit of claim 1 further comprising hyaluronic acid.

9. The kit of claim 1 further comprising polyacrylic acid.

10. The kit of claim 1 further comprising a therapeutic agent.

11. The kit of claim 1, wherein the region is a body space selected from the group consisting of a joint space or space within a vertebral disk.

12. The kit of claim 1, wherein the first solution comprises PVA.

13. The kit of claim 1, wherein the PVA is stored separate from the first solution, and is combined with the first solution prior to placement in the delivery device.

14. A kit for providing a vinyl polymer hydrogel to a region of interest via injection of a thetagel, wherein the kit comprises:
    (A) a delivery device comprising
        (i) a first chamber that can contain a first solution comprising polyvinyl alcohol (PVA), wherein the first solution has a Flory interaction parameter (chi value) that is not sufficient for gelation,
        (ii) a second chamber that can contain a second solution to be combined with the first solution, and
        (iii) a mixing chamber for combining in a controlled manner the first solution from the first chamber and the second solution from the second chamber,
    wherein combining the first and second solutions will result in an injectable thetagel solution that has a Flory interaction parameter (chi value) that is sufficient for gelation;
    (B) the first solution;
    (C) PVA; and
    (D) the second solution, wherein the delivery device when filled with the first solution and the second solution provides after injection of the injectable thetagel solution using the delivery device, a polymer hydrogel forms that has physical crosslinks between PVA molecules, wherein the polymer hydrogel is formed without chemical crosslinkers, irradiation or thermal cycling, and wherein the polymer hydrogel can fill the region.

15. The kit of claim 14, wherein the delivery device further comprises a dispensing tube.

16. The kit according to claim 14, wherein the first solution comprises one or more selected from the group consisting of deionized water, and dimethylsulfoxide.

17. The kit according to claim 14, wherein the second solution comprises one or more selected from the group consisting of salts, alcohols, polyols, amino acids, sugars, proteins, and polysaccharides.

18. The kit according to claim 14 wherein the hydrogel is anisotropic in one or more properties.

19. The kit of claim 14 wherein the injectable thetagel solution comprises about 1.0 to about 50.0 weight percent polyvinyl alcohol.

20. The kit of claim 14, wherein after the contacting the Flory interaction parameter is 0.25 to 1.0.

21. The kit of claim 14, wherein the PVA solution contains one or more non-gelling components.

22. The kit of claim 14 further comprising hyaluronic acid.

23. The kit of claim 14 further comprising polyacrylic acid.

24. The kit of claim 14 further comprising a therapeutic agent.

25. The kit of claim 14, wherein the region is a body space selected from the group consisting of a joint space or space within a vertebral disk.

26. The kit of claim 14, wherein the first solution comprises PVA.

27. The kit of claim 14, wherein the PVA is stored separate from the first solution, and is combined with the first solution prior to placement in the delivery device.

* * * * *